(12) United States Patent
Stoloff et al.

(10) Patent No.: US 8,986,703 B2
(45) Date of Patent: Mar. 24, 2015

(54) PEPTIDE SEQUENCES AND COMPOSITIONS

(75) Inventors: Gregory Alan Stoloff, London (GB); Wilson Romero Caparros-Wanderley, Aylesbury Buckinghamshire (GB)

(73) Assignee: PepTcell, Ltd. (GB)

( * ) Notice: Subject to any disclaimer, the term of this patent is extended or adjusted under 35 U.S.C. 154(b) by 628 days.

(21) Appl. No.: 12/677,682

(22) PCT Filed: Sep. 5, 2008

(86) PCT No.: PCT/EP2008/061824
§ 371 (c)(1),
(2), (4) Date: May 5, 2010

(87) PCT Pub. No.: WO2009/034041
PCT Pub. Date: Mar. 19, 2009

(65) Prior Publication Data
US 2010/0297187 A1    Nov. 25, 2010

(30) Foreign Application Priority Data

Sep. 13, 2007    (GB) .................................. 0717864.3

(51) Int. Cl.
*A61K 39/002*    (2006.01)
*C07K 14/445*    (2006.01)
(Continued)

(52) U.S. Cl.
CPC ......... *C07K 14/43577* (2013.01); *A61K 39/005* (2013.01); *A61K 38/00* (2013.01); *A61K 2039/53* (2013.01); *Y10S 530/806* (2013.01); *Y10S 530/855* (2013.01); *Y10S 530/858* (2013.01)
USPC .................. 424/185.1; 424/184.1; 424/158.1; 424/204.1; 424/265.1; 435/7.1; 435/5; 435/4; 435/243; 530/300; 530/806; 530/855; 530/858

(58) Field of Classification Search
CPC ................ A61K 2039/55516; A61K 2039/57; A61K 39/002; A61K 2039/00; C07K 14/445; C07K 2317/24; C12N 2310/3513; G01N 2333/43591; G01N 2333/44
See application file for complete search history.

(56) References Cited

FOREIGN PATENT DOCUMENTS

WO    2004/039958 A    5/2004

OTHER PUBLICATIONS

Francischetti, I. M. B; J. G. Valenzuela; V. M. Pham; M. K. garfield; J.M.C Ribeiro. (2002) Toward a catalog for the transcripts and proteins (sialome) from the salivary gland of the malaria vector *Anopheles gambiae*. Journal of Experimental Biology. 205: 2429-2451.*

(Continued)

*Primary Examiner* — Ja'Na Hines
*Assistant Examiner* — Mary Lyons
(74) *Attorney, Agent, or Firm* — One3 IP Management, P.C.; Dean G. Stathakis; Peter D. Weinstein

(57) ABSTRACT

Provided is a polypeptide composition comprising one or more polypeptides, which polypeptides are immunogenic in a vertebrate such that they cause the vertebrate to produce immune system cells capable of recognizing at least one epitope from an arthropod saliva protein fraction, wherein the arthropod saliva protein fraction has a mass of 40 kDA or less, and wherein the polypeptides are selected independently from:
the polypeptide sequences of SEQ ID 1-44 or sub-sequences from these sequences, the sub-sequences having 7 amino acids or more; or
from polypeptide sequences having 85% homology or more with one or more of the above sequences and contained in one or more of the following databases: GenBank, Protein Data Bank (PDB), SwissProt, Protein Information Resource (PIR), Protein Research Foundation (PRF), or CDS translations of these.

19 Claims, 10 Drawing Sheets

(51) Int. Cl.
*C07K 14/435* (2006.01)
*A61K 39/005* (2006.01)
*A61K 38/00* (2006.01)
*A61K 39/00* (2006.01)

(56) References Cited

OTHER PUBLICATIONS

Holt et al. 2002 (The genome sequence of the malaria mosquito *Anopheles gambiae*; Science 298:129-149).*
Lanfrancotti et al. 2002 (Novel cDNAs encoding salivary proteins from the malaria vector *Anopheles gambiae*; FEBS Letters 517: 67-71).*
Francischetti et al. (Toward a catalog for the transcripts and proteins (sialome) from the salivary gland of the malaria vector *Anopheles gambiae*; The Journal of Experimental Biology 205: 2429-2451).*
Titus et al. 2006 (The immunomodulatory factors of arthropod saliva and the potential for these factors to serve as vaccine targets to prevent pathogen transmission; Parasite Immunology 28:131-141).*
Brown et al. (J. Immunol. May 1996;156(9):3285-91 at 3290 and Tables 1 and 2).*
Arca Bruno et al., "Trapping cDNAs encoding secreted proteins from the salivary glands of the malaria vector *Anopheles gambiae*," Proceeding of the National Academy of Science, 1999, pp. 1516-1521, vol. 96, No. 4.
Donovan Michael et al., "Uninfected mosquito bites confer protection against infection with malaria parasites," Infection and Immunity, 2007, pp. 2523-2530, vol. 75, No. 5.
Francischetti Ivo MB et al., "Toward a catalog for the transcripts and proteins (sialome) from the salivary gland of the malaria vector *Anopheles gambiae*," J. of Experimental Biology, 2002 pp. 2429-2451, vol. 205, No. 16.

Holt RA et al., "The Genome Sequence of the Malaria Mosquito *Anopheles gambiae*," Science, American Association for the Advancement of Science, 2003, pp. 129-149, vol. 298.
Lanfrancotti A et al., "Novel cDNAs encoding salivary proteins from the malaria vector *Anopheles gambiae*," FEBS Letters, 2002, pp. 67-71, vol. 517, No. 1-3.
Montero-Solis C et al., "Identification and characterization of gp65, a salivary-gland-specific molecule expressed in the malaria vector *Anopheles albimanus*," Insect Molecular Biology, 2004, pp. 155-164, vol. 13, No. 2.
Valenzuela JG et al., "The D7 family of salivary proteins in blood sucking diptera," Insect Molecular Biology, 2002, pp. 149-155, vol. 11, No. 2.
Waitayakul et al., "Natural human humoral response to salivary gland proteins of *Anopheles* mosquitoes in Thailand," Acta Tropica, 2006, pp. 66-73, vol. 98, No. 1.
Durand-Fleith, Odette, "International Search Report," European Patent Office, PCT/EP2008/061824, Sep. 5, 2008.
NCBI Accession AAL68793.1; hypothetical protein 16 [*Anopheles gambiae*]; First seen Jan. 2002; Francischetti, et al., http://www.ncbi.nlm.nig.gov/entrez/viewer.fcgi?db=protein&id=18389913.
NCBI Accession EAU77336.1; [*Anopheles gambiae* str. PEST]; First seen Oct. 2006; http://www.ncbi.nlm.nig.gov/entrez/viewer.fcgi?116130825:WGS:25288218.
Kaye, Jeremy, "Search Report under Sectio 17(5)," UK Intellectual Property Office, Jan. 22, 2008.
Cornelie, et al., An insight into immunogenic salivary proteins of *Anopheles gambiae* in African children, Malaria J. 6: 75-81.
Orlandi-Pradines, et al., Antibody response against saliva antigens of *Anopheles gambiae* and *Aedes aegypti* in travellers in tropical Africa, Microbes Infect. 9(12-13) 1454-1462 (2007).
Immunologists' Toolbox, In Immunobiology: The Immune System in Health and Disease, Appendix I (5th ed; Janeway CA Jr, Travers P, Walport M, et al. New York: Garland Science; 2001).

* cited by examiner

SEQUENCE LISTING

```
<160> NUMBER OF SEQ ID NOS: 134

<210> SEQ ID NO 1
<211> LENGTH: 32
<212> TYPE: PRT
<213> ORGANISM: Artificial Sequence
<220> FEATURE:
<223> OTHER INFORMATION: Immunogenic polypeptide

<400> SEQUENCE: 1

His Leu Thr Leu Phe Thr Val Ala Val Leu Leu Leu Ala Ala Ala Ala
1               5                   10                  15

Leu Leu Leu Leu Leu Pro Pro Ala Tyr Ser Thr Thr Leu Thr Pro Pro
            20                  25                  30

<210> SEQ ID NO 2
<211> LENGTH: 25
<212> TYPE: PRT
<213> ORGANISM: Artificial Sequence
<220> FEATURE:
<223> OTHER INFORMATION: Immunogenic polypeptide

<400> SEQUENCE: 2

Pro Leu Ser Tyr Cys His Leu Phe Leu Thr His Thr Leu Ala Arg Ala
1               5                   10                  15

Leu Ser Phe Ser Arg Ser Asp Cys Leu
```

```
                        20                  25

<210> SEQ ID NO 3
<211> LENGTH: 24
<212> TYPE: PRT
<213> ORGANISM: Artificial Sequence
<220> FEATURE:
<223> OTHER INFORMATION: Immunogenic polypeptide

<400> SEQUENCE: 3

Lys Asn Val Phe Phe Ala Leu Leu Leu Val Val Leu Val Cys Cys Leu
1               5                   10                  15

Val Ser Val Gln Gly Asn Glu Ile
            20

<210> SEQ ID NO 4
<211> LENGTH: 27
<212> TYPE: PRT
<213> ORGANISM: Artificial Sequence
<220> FEATURE:
<223> OTHER INFORMATION: Immunogenic polypeptide

<400> SEQUENCE: 4

Lys Leu Leu Val Leu Leu Ile Cys Leu Phe Phe Tyr His Thr His Cys
1               5                   10                  15

Thr Thr Ala Tyr Leu Trp Leu Ala Met Gly Val
            20                  25

<210> SEQ ID NO 5
<211> LENGTH: 25
<212> TYPE: PRT
<213> ORGANISM: Artificial Sequence
<220> FEATURE:
<223> OTHER INFORMATION: Immunogenic polypeptide

<400> SEQUENCE: 5

Phe Leu Lys Gly Ser Phe Pro Arg Phe Gln Met Cys Val Met Leu Ile
1               5                   10                  15

Gly Phe Phe Ser Ser Ala Lys Cys Leu
            20                  25

<210> SEQ ID NO 6
<211> LENGTH: 29
<212> TYPE: PRT
<213> ORGANISM: Artificial Sequence
<220> FEATURE:
<223> OTHER INFORMATION: Immunogenic polypeptide

<400> SEQUENCE: 6

Asn Asp Tyr Gln Ala Leu Leu Gly Leu Cys Cys Pro Trp Ile Asp Leu
1               5                   10                  15

Ala Ala Ala Asp Leu Pro Met Arg Arg His Ala Lys Ala
            20                  25

<210> SEQ ID NO 7
<211> LENGTH: 31
<212> TYPE: PRT
<213> ORGANISM: Artificial Sequence
<220> FEATURE:
<223> OTHER INFORMATION: Immunogenic polypeptide

<400> SEQUENCE: 7

Phe Tyr Ser Val Gly Lys Leu Val Lys Val Leu Leu Val Met Ala Val
1               5                   10                  15
```

Cys Cys Leu Leu Leu Cys Thr Ala Pro Thr Gly Ala Asp Pro Leu
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Immunogenic polypeptide

<400> SEQUENCE: 8

Met Lys Phe Ala Phe Ala Phe Val Leu Ile Ala Leu Phe Ala Val Phe
1               5                   10                  15

Ala Val Ser Gln Ala Leu Pro Gln Pro Glu Gln Ala Ala Ala
            20                  25                  30

<210> SEQ ID NO 9
<211> LENGTH: 21
<212> TYPE: PRT
<213> ORGANISM: Artificial Sequence
<220> FEATURE:
<223> OTHER INFORMATION: Immunogenic polypeptide

<400> SEQUENCE: 9

Asp Gly Ala Ser Ala Ile Thr Lys Ile Val Leu Glu Leu Thr Pro Glu
1               5                   10                  15

Gln Ala Ala Ala Val
            20

<210> SEQ ID NO 10
<211> LENGTH: 33
<212> TYPE: PRT
<213> ORGANISM: Artificial Sequence
<220> FEATURE:
<223> OTHER INFORMATION: Immunogenic polypeptide

<400> SEQUENCE: 10

Thr Leu Phe Ile Phe Leu Val Cys Cys Gln Ile Pro Leu Phe Gly Ile
1               5                   10                  15

Met Ser Ser Asp Ser Ala Asp Pro Phe Tyr Trp Ile Arg Val Ile Leu
            20                  25                  30

Ala

<210> SEQ ID NO 11
<211> LENGTH: 22
<212> TYPE: PRT
<213> ORGANISM: Artificial Sequence
<220> FEATURE:
<223> OTHER INFORMATION: Immunogenic polypeptide

<400> SEQUENCE: 11

Gly Arg Val Met Cys Leu Leu Arg Leu Met Ser Thr Leu Leu Val Val
1               5                   10                  15

Leu Ser Ile Val Gly Lys
            20

<210> SEQ ID NO 12
<211> LENGTH: 38
<212> TYPE: PRT
<213> ORGANISM: Artificial Sequence
<220> FEATURE:
<223> OTHER INFORMATION: Immunogenic polypeptide

<400> SEQUENCE: 12

```
Leu Tyr Ser Gly Tyr Arg Leu Leu Val Leu Val Met Thr Val Cys
1               5                   10                  15

Cys Leu Leu Leu Phe Ile Ala Pro Thr Gly Ala Asp Pro Leu Pro Gly
                20                  25                  30

Gln Thr Gln Arg Thr Leu
            35
```

<210> SEQ ID NO 13
<211> LENGTH: 37
<212> TYPE: PRT
<213> ORGANISM: Artificial Sequence
<220> FEATURE:
<223> OTHER INFORMATION: Immunogenic polypeptide

<400> SEQUENCE: 13

```
Met Tyr Cys Val Ile Lys Gly Lys Thr Gly Gly Tyr Cys Asn Ser Glu
1               5                   10                  15

Gly Leu Cys Thr Cys Arg Ala Glu Asp Leu His Phe Leu Leu Lys Pro
                20                  25                  30

Ile Ile Asn Lys Asp
            35
```

<210> SEQ ID NO 14
<211> LENGTH: 36
<212> TYPE: PRT
<213> ORGANISM: Artificial Sequence
<220> FEATURE:
<223> OTHER INFORMATION: Immunogenic polypeptide

<400> SEQUENCE: 14

```
Asn Ala Glu Asp Pro Arg Thr Glu Leu Ile Gly Cys Gly Ser Val Leu
1               5                   10                  15

Phe His Leu Ala Ala Asn Arg Leu Ser Leu Gln Leu Glu Glu Phe Ala
                20                  25                  30

Val Cys Lys Arg
            35
```

<210> SEQ ID NO 15
<211> LENGTH: 37
<212> TYPE: PRT
<213> ORGANISM: Artificial Sequence
<220> FEATURE:
<223> OTHER INFORMATION: Immunogenic polypeptide

<400> SEQUENCE: 15

```
Ala Leu Ile Gly Leu Leu Leu Cys Ser Val Gln Ser Val Thr Ala Asn
1               5                   10                  15

Asp Pro Val Asp Ala Leu Gly Ala Cys Ser Gly Asn Leu Phe Gly Leu
                20                  25                  30

Leu Met Thr Arg Leu
            35
```

<210> SEQ ID NO 16
<211> LENGTH: 30
<212> TYPE: PRT
<213> ORGANISM: Artificial Sequence
<220> FEATURE:
<223> OTHER INFORMATION: Immunogenic polypeptide

<400> SEQUENCE: 16

```
Ser Lys Leu Phe Val Leu Ala Phe Leu Cys Leu Ala Leu Val Val Val
1               5                   10                  15
```

Val Gln Ser Ala Pro Gln Tyr Ala Arg Gly Asp Val Pro Thr
                20                  25                  30

<210> SEQ ID NO 17
<211> LENGTH: 38
<212> TYPE: PRT
<213> ORGANISM: Artificial Sequence
<220> FEATURE:
<223> OTHER INFORMATION: Immunogenic polypeptide

<400> SEQUENCE: 17

Ser Met Leu Val Ala Phe Ala Thr Leu Ser Val Ala Leu Val Val
1               5                   10                  15

Val Ala Ile Pro Ala Asn Phe Asn Tyr Gly Gly Gly Gly Tyr Phe
                20                  25                  30

Ile Asn Gly Thr Gly Gln
        35

<210> SEQ ID NO 18
<211> LENGTH: 31
<212> TYPE: PRT
<213> ORGANISM: Artificial Sequence
<220> FEATURE:
<223> OTHER INFORMATION: Immunogenic polypeptide

<400> SEQUENCE: 18

Ile Tyr Glu Lys Leu Pro Ala Tyr Leu Ser Glu Val Ser Ala Arg Val
1               5                   10                  15

Asn Val Leu Gln Val Ser Leu Gln His Asp Leu Pro Asn Leu Gln
                20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Immunogenic polypeptide

<400> SEQUENCE: 19

Glu Met Lys Leu Ala Lys Val Ala Leu Val Thr Ile Ser Leu Trp Phe
1               5                   10                  15

Met Ala Trp Thr Pro Tyr Leu Val Ile Asn Phe Thr Gly Ile
                20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Immunogenic polypeptide

<400> SEQUENCE: 20

Leu Leu Pro Ala Lys Val Ile Pro Asp Lys Thr Ala Ala Tyr Val Ala
1               5                   10                  15

Tyr Gly Gly Gln Glu Thr Leu Val Glu His Val Glu Val Leu Val
                20                  25                  30

<210> SEQ ID NO 21
<211> LENGTH: 27
<212> TYPE: PRT
<213> ORGANISM: Artificial Sequence
<220> FEATURE:
<223> OTHER INFORMATION: Immunogenic polypeptide

<400> SEQUENCE: 21

```
Phe Tyr Thr Cys Phe Leu Gly Thr Ser Ser Leu Ala Gly Phe Lys Asn
1               5                   10                  15

Ala Val Asp Tyr Asp Glu Leu Leu Lys Ala Gly
            20                  25
```

```
<210> SEQ ID NO 22
<211> LENGTH: 31
<212> TYPE: PRT
<213> ORGANISM: Artificial Sequence
<220> FEATURE:
<223> OTHER INFORMATION: Immunogenic polypeptide

<400> SEQUENCE: 22
```

```
Val Leu Glu Val Leu Gly Phe Val Glu Asp Asn Gly Glu Leu Val Phe
1               5                   10                  15

Gln Glu Leu Leu Gly Val Leu Lys Met Val Asp Pro Asp Gly Asp
            20                  25                  30
```

```
<210> SEQ ID NO 23
<211> LENGTH: 45
<212> TYPE: PRT
<213> ORGANISM: Artificial Sequence
<220> FEATURE:
<223> OTHER INFORMATION: Immunogenic polypeptide

<400> SEQUENCE: 23
```

```
Lys Leu Thr Pro Thr Val Val Val Leu Leu Cys Leu Thr Phe Val
1               5                   10                  15

Ala Asp Ala Leu Thr Ile Gln Glu Leu Arg Ala Gln Ile Ala Gln Gln
            20                  25                  30

Arg Ile Gln Gln Arg Tyr Gly Val Thr Val Ala Thr Thr
        35                  40                  45
```

```
<210> SEQ ID NO 24
<211> LENGTH: 38
<212> TYPE: PRT
<213> ORGANISM: Artificial Sequence
<220> FEATURE:
<223> OTHER INFORMATION: Immunogenic polypeptide

<400> SEQUENCE: 24
```

```
Ser Leu Ser Asp Tyr Gly Leu Ile Glu Leu Lys Glu His Cys Leu Glu
1               5                   10                  15

Cys Cys Gln Lys Asp Thr Glu Ala Asp Ser Lys Leu Lys Val Tyr Pro
            20                  25                  30

Ala Ala Val Leu Glu Val
        35
```

```
<210> SEQ ID NO 25
<211> LENGTH: 37
<212> TYPE: PRT
<213> ORGANISM: Artificial Sequence
<220> FEATURE:
<223> OTHER INFORMATION: Immunogenic polypeptide

<400> SEQUENCE: 25
```

```
Thr Tyr Ile Cys Phe Ile Leu His Gly Val Ser Glu Ile Ile Pro Gln
1               5                   10                  15

Gln Gln Lys Lys Thr Met Lys Phe Leu Leu Leu Val Ala Ser Val Leu
            20                  25                  30

Cys Leu Val Leu Ile
        35
```

```
<210> SEQ ID NO 26
<211> LENGTH: 20
<212> TYPE: PRT
<213> ORGANISM: Artificial Sequence
<220> FEATURE:
<223> OTHER INFORMATION: Immunogenic polypeptide

<400> SEQUENCE: 26

Arg Tyr Phe Val Val Ile Ala Leu Ile Cys Pro Leu Ile Ile Val Glu
1               5                   10                  15

Thr Leu Ala Val
            20

<210> SEQ ID NO 27
<211> LENGTH: 36
<212> TYPE: PRT
<213> ORGANISM: Artificial Sequence
<220> FEATURE:
<223> OTHER INFORMATION: Immunogenic polypeptide

<400> SEQUENCE: 27

Leu Leu Leu Tyr Leu Asp Ala Ala Asp Leu Arg Arg Ala Leu His Gln
1               5                   10                  15

Tyr Gln Leu Leu Ala Ala Gln Gly Asp Arg His Leu Pro Gln Gln Ile
            20                  25                  30

Val Lys Phe Val
        35

<210> SEQ ID NO 28
<211> LENGTH: 37
<212> TYPE: PRT
<213> ORGANISM: Artificial Sequence
<220> FEATURE:
<223> OTHER INFORMATION: Immunogenic polypeptide

<400> SEQUENCE: 28

Val Leu Leu Thr Pro Ala Leu Gln Ala Tyr Ile Met Asp Glu His Asn
1               5                   10                  15

Leu Asn Arg Ser Asn Ile Ala Leu Gly Arg Ile Arg Pro Tyr Pro Ser
            20                  25                  30

Ala Val Lys Met Pro
        35

<210> SEQ ID NO 29
<211> LENGTH: 27
<212> TYPE: PRT
<213> ORGANISM: Artificial Sequence
<220> FEATURE:
<223> OTHER INFORMATION: Immunogenic polypeptide

<400> SEQUENCE: 29

Val Leu Lys Gly Glu Thr His Lys Ala Leu Lys Leu Lys Asp Gly Gly
1               5                   10                  15

His Tyr Leu Val Glu Phe Lys Ser Ile Tyr Met
            20                  25

<210> SEQ ID NO 30
<211> LENGTH: 40
<212> TYPE: PRT
<213> ORGANISM: Artificial Sequence
<220> FEATURE:
<223> OTHER INFORMATION: Immunogenic polypeptide

<400> SEQUENCE: 30
```

```
Val Leu His Ser Met Leu Val Asn Ala Ser Leu Ala Glu Met Val Lys
1               5                   10                  15

Glu Ser Tyr Gln Thr His Gly Ala Asp Gly Arg Met Val Val Arg Met
                20                  25                  30

Leu Lys Phe Val Arg Leu Leu Pro
            35                  40
```

<210> SEQ ID NO 31
<211> LENGTH: 32
<212> TYPE: PRT
<213> ORGANISM: Artificial Sequence
<220> FEATURE:
<223> OTHER INFORMATION: Immunogenic polypeptide

<400> SEQUENCE: 31

```
Arg Val Arg Ala Leu Arg Ala Leu Leu Glu Thr Leu Leu Gln His Gln
1               5                   10                  15

Gly Glu Gln Asn Asn Asp Val Tyr Leu Ile Arg Leu Ala His Glu Thr
                20                  25                  30
```

<210> SEQ ID NO 32
<211> LENGTH: 37
<212> TYPE: PRT
<213> ORGANISM: Artificial Sequence
<220> FEATURE:
<223> OTHER INFORMATION: Immunogenic polypeptide

<400> SEQUENCE: 32

```
Glu Leu Gln Gln Ala Leu Ser Ser Leu Asn Ala Gly Ser Gly Ser Cys
1               5                   10                  15

Ala Glu Val Phe Asn Ala Tyr Leu Pro Val His Asn Lys Tyr Ile Gly
                20                  25                  30

Val Ser Arg Lys Ile
            35
```

<210> SEQ ID NO 33
<211> LENGTH: 33
<212> TYPE: PRT
<213> ORGANISM: Artificial Sequence
<220> FEATURE:
<223> OTHER INFORMATION: Immunogenic polypeptide

<400> SEQUENCE: 33

```
Lys Phe Tyr Arg Leu Ile Ser Thr Leu Leu Val Val Val Ile Ala
1               5                   10                  15

Pro Arg His Gln Cys Ser Pro Phe Phe Gln Tyr Asn Arg Pro Tyr
                20                  25                  30

Leu
```

<210> SEQ ID NO 34
<211> LENGTH: 36
<212> TYPE: PRT
<213> ORGANISM: Artificial Sequence
<220> FEATURE:
<223> OTHER INFORMATION: Immunogenic polypeptide

<400> SEQUENCE: 34

```
Asn Tyr Val Pro Asp Val Ser Ala Leu Glu Gln Asp Ile Ile Glu Val
1               5                   10                  15

Asp Pro Glu Thr Lys Glu Met Leu Lys His Leu Asp Phe Asn Asn Ile
                20                  25                  30
```

Val Val Gln Leu
        35

<210> SEQ ID NO 35
<211> LENGTH: 28
<212> TYPE: PRT
<213> ORGANISM: Artificial Sequence
<220> FEATURE:
<223> OTHER INFORMATION: Immnogenic polypeptide

<400> SEQUENCE: 35

Gln Tyr Ser Met Glu Cys Leu Glu Ala Ala Glu Pro Lys Tyr Leu Asp
1               5                   10                  15

Gly Leu Lys Thr Leu Ala Asp Glu Thr Ala Gln Cys
            20                  25

<210> SEQ ID NO 36
<211> LENGTH: 32
<212> TYPE: PRT
<213> ORGANISM: Artificial Sequence
<220> FEATURE:
<223> OTHER INFORMATION: Immunogenic polypeptide

<400> SEQUENCE: 36

Glu Tyr Ala Gln Val Thr Lys Met Leu Gly Asn Gly Arg Leu Glu Ala
1               5                   10                  15

Met Cys Phe Asp Gly Val Lys Arg Leu Cys His Ile Arg Gly Lys Leu
            20                  25                  30

<210> SEQ ID NO 37
<211> LENGTH: 26
<212> TYPE: PRT
<213> ORGANISM: Artificial Sequence
<220> FEATURE:
<223> OTHER INFORMATION: Immunogenic polypeptide

<400> SEQUENCE: 37

Lys Leu Phe Leu Thr Leu Leu Ser Thr Leu Ser Val Ala Met Val Phe
1               5                   10                  15

Ala Leu Pro Ala His His His Ser Arg Gly
            20                  25

<210> SEQ ID NO 38
<211> LENGTH: 33
<212> TYPE: PRT
<213> ORGANISM: Artificial Sequence
<220> FEATURE:
<223> OTHER INFORMATION: Immunogenic polypeptide

<400> SEQUENCE: 38

Glu Leu Glu Glu Ala Arg Leu Val Ala Glu Glu Leu Glu Glu Arg Gln
1               5                   10                  15

Gln Glu Leu Asp Tyr Leu Lys Arg Tyr Leu Val Gly Arg Leu Gln Ala
            20                  25                  30

Val

<210> SEQ ID NO 39
<211> LENGTH: 19
<212> TYPE: PRT
<213> ORGANISM: Artificial Sequence
<220> FEATURE:
<223> OTHER INFORMATION: Immunogenic polypeptide

<400> SEQUENCE: 39

```
Ser Tyr Phe Leu Thr Val Cys Leu Leu Ala Leu Val Gln Ser Glu Thr
1               5                   10                  15

Val Gln Asp

<210> SEQ ID NO 40
<211> LENGTH: 31
<212> TYPE: PRT
<213> ORGANISM: Artificial Sequence
<220> FEATURE:
<223> OTHER INFORMATION: Immunogenic polypeptide

<400> SEQUENCE: 40

Ala Met Thr Asn Ala Asn Leu Val Gly Leu Thr Ile Ser Leu Ala Tyr
1               5                   10                  15

Ala Ile Phe Phe Leu Leu Tyr Thr Pro Pro Thr Gly Arg Ser Ser
            20                  25                  30

<210> SEQ ID NO 41
<211> LENGTH: 36
<212> TYPE: PRT
<213> ORGANISM: Artificial Sequence
<220> FEATURE:
<223> OTHER INFORMATION: Immunogenic polypeptide

<400> SEQUENCE: 41

Ser Phe Ala Trp Leu Leu Tyr Gly Ile Ile Leu Arg Ser Asn Phe Leu
1               5                   10                  15

Val Val Gln Asn Leu Met Ala Leu Ala Leu Ser Ala Val Gln Leu Ser
            20                  25                  30

Leu Phe Ile Ile
            35

<210> SEQ ID NO 42
<211> LENGTH: 36
<212> TYPE: PRT
<213> ORGANISM: Artificial Sequence
<220> FEATURE:
<223> OTHER INFORMATION: Immunogenic polypeptide

<400> SEQUENCE: 42

Ala Phe Pro Phe Ile Ser Gly Phe Leu Ser Cys Phe Met Trp Leu Lys
1               5                   10                  15

Tyr Gly Val Leu Thr Glu Glu Ser Thr Leu Ile Leu Val Asn Phe Ile
            20                  25                  30

Gly Ser Ala Leu
            35

<210> SEQ ID NO 43
<211> LENGTH: 24
<212> TYPE: PRT
<213> ORGANISM: Artificial Sequence
<220> FEATURE:
<223> OTHER INFORMATION: Immunogenic polypeptide

<400> SEQUENCE: 43

Gly Leu Leu Cys Cys Cys Leu Ala Val Leu Phe Phe Ala Ser Pro Leu
1               5                   10                  15

Thr Met Leu Ala His Val Ile Arg
            20

<210> SEQ ID NO 44
<211> LENGTH: 26
<212> TYPE: PRT
```

<213> ORGANISM: Artificial Sequence
<220> FEATURE:
<223> OTHER INFORMATION: Immunogenic polypeptide

<400> SEQUENCE: 44

Leu Leu Leu Ala Met Val Leu Leu Pro Leu Leu Leu Glu Ser Val
1               5                   10                  15

Val Pro Tyr Ala Ala Ala Glu Lys Val Trp
            20                  25

<210> SEQ ID NO 45
<211> LENGTH: 48
<212> TYPE: PRT
<213> ORGANISM: Anopheles gambiae

<400> SEQUENCE: 45

Met His Leu Thr Leu Phe Thr Val Ala Val Leu Leu Ala Ala Ala
1               5                   10                  15

Ala Leu Leu Leu Leu Pro Pro Ala Tyr Ser Thr Thr Leu Thr Pro
            20                  25                  30

Pro Ala Pro Pro Arg Leu Ser His Leu Gly Ile Thr Ile Gly Arg Ile
        35                  40                  45

<210> SEQ ID NO 46
<211> LENGTH: 46
<212> TYPE: PRT
<213> ORGANISM: Anopheles gambiae

<400> SEQUENCE: 46

Met Pro Leu Ser Tyr Cys His Leu Phe Leu Thr His Thr Leu Ala Arg
1               5                   10                  15

Ala Leu Ser Phe Ser Arg Ser Asp Cys Leu Lys Phe Ser Glu Lys Arg
            20                  25                  30

Leu Leu Phe Ser Gly Ser Lys Thr Phe Pro Thr Thr Leu Leu
        35                  40                  45

<210> SEQ ID NO 47
<211> LENGTH: 56
<212> TYPE: PRT
<213> ORGANISM: Anopheles gambiae

<400> SEQUENCE: 47

Met Lys Asn Val Phe Phe Ala Leu Leu Leu Val Val Leu Val Cys Cys
1               5                   10                  15

Leu Val Ser Val Gln Gly Asn Glu Ile Ile Gln Asn Val Lys Arg
            20                  25                  30

Ser Ile Pro Leu Arg Gln Leu Ile Leu Gln His Asn Ala Leu Asp Asp
        35                  40                  45

Ser Asn Ser Asp Ser Gly Ser Gln
    50                  55

<210> SEQ ID NO 48
<211> LENGTH: 56
<212> TYPE: PRT
<213> ORGANISM: Anopheles gambiae

<400> SEQUENCE: 48

Met Cys Ile Phe Phe Gln Ala Gly Ile Lys Leu Leu Val Leu Leu Ile
1               5                   10                  15

Cys Leu Phe Phe Tyr His Thr His Cys Thr Thr Ala Tyr Leu Trp Leu
            20                  25                  30

```
Ala Met Gly Val Glu Ala Lys Ser Ile Lys Ala Arg Gly Thr Ala His
        35                  40                  45

Ser Lys Ser Arg Thr Ser Thr Asn
    50                  55

<210> SEQ ID NO 49
<211> LENGTH: 57
<212> TYPE: PRT
<213> ORGANISM: Anopheles gambiae

<400> SEQUENCE: 49

Met Phe Leu Lys Gly Ser Phe Pro Arg Phe Gln Met Cys Val Met Leu
1               5                   10                  15

Ile Gly Phe Phe Ser Ser Ala Lys Cys Leu Met Cys Phe Ala Asp Trp
            20                  25                  30

Glu Gly Met Leu Leu Met Thr Met Glu Val Phe Asp Phe Gln Leu Ile
        35                  40                  45

Val Phe Thr Pro Val Leu Lys Arg Ser
    50                  55

<210> SEQ ID NO 50
<211> LENGTH: 65
<212> TYPE: PRT
<213> ORGANISM: Anopheles gambiae

<400> SEQUENCE: 50

Met Ala Gly Glu Ser Gln Lys Asn Ala Arg Ser Lys Gln Asn Asp Tyr
1               5                   10                  15

Gln Ala Leu Leu Gly Leu Cys Cys Pro Trp Ile Asp Leu Ala Ala Ala
            20                  25                  30

Asp Leu Pro Met Arg Arg His Ala Lys Ala Arg Glu Ala Ile Asn Phe
        35                  40                  45

Leu Leu Gln Ala His Glu Ala Gly Pro Asn Glu Glu Pro Ser Leu Pro
    50                  55                  60

Ala
65

<210> SEQ ID NO 51
<211> LENGTH: 78
<212> TYPE: PRT
<213> ORGANISM: Anopheles gambiae

<400> SEQUENCE: 51

Met Lys Phe Tyr Ser Val Gly Lys Leu Val Lys Val Leu Leu Val Met
1               5                   10                  15

Ala Val Cys Cys Leu Leu Leu Cys Thr Ala Pro Thr Gly Ala Asp Pro
            20                  25                  30

Leu Pro Gly Arg Asp Arg Asn Thr Ile Ala Asn Lys Ser Lys Asp Lys
        35                  40                  45

Lys Ala Ser Ala Pro Lys His Ser Leu Gly Thr Gly Ala Arg Met Ala
    50                  55                  60

Leu Thr Gly Gly Gly Val Leu Gly Gly Val Leu Thr Asn Met
65                  70                  75

<210> SEQ ID NO 52
<211> LENGTH: 83
<212> TYPE: PRT
<213> ORGANISM: Anopheles gambiae
```

```
<400> SEQUENCE: 52

Met Lys Phe Ala Phe Ala Phe Val Leu Ile Ala Leu Phe Ala Val Phe
1               5                   10                  15

Ala Val Ser Gln Ala Leu Pro Gln Pro Glu Gln Ala Ala Ser Ser
            20                  25                  30

Asn Asp Gly Ala Ser Ala Ile Thr Lys Ile Val Leu Glu Leu Thr Pro
            35                  40                  45

Glu Gln Ala Ala Val Gln Lys Met Gly Gly Arg Gly Phe Trp Pro
50                  55                  60

Ile Met Met Lys Ser Val Lys Lys Ile Met Ala Ile Gly Cys Asp Leu
65                  70                  75                  80

Ile Asp Cys

<210> SEQ ID NO 53
<211> LENGTH: 77
<212> TYPE: PRT
<213> ORGANISM: Anopheles gambiae

<400> SEQUENCE: 53

Met Gly Ile Lys Phe Leu Glu Ile Ile Lys Pro Phe Cys Gly Ile Leu
1               5                   10                  15

Pro Glu Ile Ala Lys Pro Glu Arg Lys Ile Gln Phe Arg Glu Lys Val
            20                  25                  30

Leu Trp Thr Ala Ile Thr Leu Phe Ile Phe Leu Val Cys Cys Gln Ile
            35                  40                  45

Pro Leu Phe Gly Ile Met Ser Ser Asp Ser Ala Asp Pro Phe Tyr Trp
50                  55                  60

Ile Arg Val Ile Leu Ala Ser Asn Arg Gly Thr Leu Met
65                  70                  75

<210> SEQ ID NO 54
<211> LENGTH: 85
<212> TYPE: PRT
<213> ORGANISM: Anopheles gambiae

<400> SEQUENCE: 54

Met Gly Arg Val Met Cys Leu Leu Arg Leu Met Ser Thr Leu Leu Val
1               5                   10                  15

Val Leu Ser Ile Val Gly Lys Lys Thr Asn Ala Ala Pro Gln Val Thr
            20                  25                  30

Glu Ala Pro Gly Asn Val Gly Ser Thr Tyr Ser Pro Met Ala Asp Ile
            35                  40                  45

Gly Arg Leu Ala Thr Gly Ala Thr Lys Leu Phe Gly Gln Phe Trp Asn
50                  55                  60

Thr Gly Thr Arg Phe Gly Thr Glu Leu Ser Arg Arg Thr Phe Asp Phe
65                  70                  75                  80

Leu Arg Val Lys Lys
            85

<210> SEQ ID NO 55
<211> LENGTH: 91
<212> TYPE: PRT
<213> ORGANISM: Anopheles gambiae

<400> SEQUENCE: 55

Met Ala Gly Asp Ile Gln Leu Phe Ser Thr Arg Glu Thr Thr Met Lys
1               5                   10                  15
```

-continued

```
Leu Tyr Ser Gly Tyr Arg Leu Leu Val Leu Val Met Thr Val Cys
            20                  25                  30

Cys Leu Leu Leu Phe Ile Ala Pro Thr Gly Ala Asp Pro Leu Pro Gly
            35                  40                  45

Gln Thr Gln Arg Thr Leu Gly Tyr Arg Gly Asn Asp Lys Arg Ala Thr
50                  55                  60

Pro Pro Met His Ser Leu Gly Ser Gly Ala Arg Met Ala Met Thr Gly
65                  70                  75                  80

Gly Gly Ile Leu Gly Gly Ile Phe Ser Ala Leu
                85                  90
```

<210> SEQ ID NO 56
<211> LENGTH: 93
<212> TYPE: PRT
<213> ORGANISM: Anopheles gambiae

<400> SEQUENCE: 56

```
Met Asp Gln Cys Ser Val Pro Arg Leu Cys Ile Ile Ile Met Lys Ser
1               5                   10                  15

Phe Ile Ala Ala Ala Val Ile Ala Leu Ile Cys Ala Ile Ala Val Ser
            20                  25                  30

Gly Thr Thr Val Thr Leu Gln Ser Thr Cys Lys Leu Phe Thr Ala Asp
            35                  40                  45

Val Val Ser Ser Ile Thr Cys Lys Met Tyr Cys Val Ile Lys Gly Lys
50                  55                  60

Thr Gly Gly Tyr Cys Asn Ser Glu Gly Leu Cys Thr Cys Arg Ala Glu
65                  70                  75                  80

Asp Leu His Phe Leu Leu Lys Pro Ile Ile Asn Lys Asp
                85                  90
```

<210> SEQ ID NO 57
<211> LENGTH: 90
<212> TYPE: PRT
<213> ORGANISM: Anopheles gambiae

<400> SEQUENCE: 57

```
Met Arg Phe Leu Ser Val Leu Thr Val Gly Leu Leu Val Trp Val Gly
1               5                   10                  15

Val Phe Ala Thr Val Asn Ala Glu Asp Pro Arg Thr Glu Leu Ile Gly
            20                  25                  30

Cys Gly Ser Val Leu Phe His Leu Ala Ala Asn Arg Leu Ser Leu Gln
            35                  40                  45

Leu Glu Glu Phe Ala Val Cys Lys Arg Ser Asn Pro Gly Tyr Asp Cys
50                  55                  60

Ser Asp Ser Ile His Arg Ala Ile Ser Asp Leu Gln Gln Gly Leu Phe
65                  70                  75                  80

Asp Leu Asn His Cys Thr Lys Asp Ile Arg
                85                  90
```

<210> SEQ ID NO 58
<211> LENGTH: 92
<212> TYPE: PRT
<213> ORGANISM: Anopheles gambiae

<400> SEQUENCE: 58

```
Met Arg Phe Cys Cys Val Ala Leu Ile Gly Leu Leu Leu Cys Ser Val
1               5                   10                  15

Gln Ser Val Thr Ala Asn Asp Pro Val Asp Ala Leu Gly Ala Cys Ser
```

```
                    20                  25                  30
Gly Asn Leu Phe Gly Leu Leu Met Thr Arg Leu Gln Gln Met Val Glu
            35                  40                  45

Asp Phe Thr Ala Cys Arg Gln Glu Ala Thr Ala Asn Asp Pro Gln His
        50                  55                  60

Asp Arg Ser Asp Ser Ile Gln Arg Ala Lys Val Asp Leu Gln Gln Gln
65                  70                  75                  80

Leu Val Asn Tyr Ser Tyr Cys Thr Lys Asn Ile Gln
                85                  90

<210> SEQ ID NO 59
<211> LENGTH: 101
<212> TYPE: PRT
<213> ORGANISM: Anopheles gambiae

<400> SEQUENCE: 59

Met Ala Ser Lys Leu Phe Val Leu Ala Phe Leu Cys Leu Ala Leu Val
1               5                   10                  15

Val Val Val Gln Ser Ala Pro Gln Tyr Ala Arg Gly Asp Val Pro Thr
                20                  25                  30

Tyr Asp Glu Glu Asp Phe Asp Glu Glu Ser Leu Lys Pro His Ser Ser
            35                  40                  45

Ser Pro Ser Asp Asp Gly Glu Glu Phe Asp Pro Ser Leu Leu Glu
        50                  55                  60

Glu His Ala Asp Ala Pro Thr Ala Arg Asp Pro Gly Arg Asn Pro Glu
65                  70                  75                  80

Phe Leu Arg Asn Ser Asn Thr Asp Glu Gln Ala Ser Ala Pro Ala Ala
                85                  90                  95

Ser Ser Ser Asp Ser
            100

<210> SEQ ID NO 60
<211> LENGTH: 114
<212> TYPE: PRT
<213> ORGANISM: Anopheles gambiae

<400> SEQUENCE: 60

Met Lys Ser Met Leu Val Ala Phe Ala Thr Leu Ser Val Ala Leu Val
1               5                   10                  15

Val Val Val Ala Ile Pro Ala Asn Phe Asn Tyr Gly Gly Gly Gly Gly
                20                  25                  30

Tyr Phe Ile Asn Gly Thr Gly Gln Ser Phe Asn Phe Ser Gly Glu Ser
            35                  40                  45

Asn Gly Thr Ser Ile Pro Gly Leu Pro Asp Phe Gly Ser Phe Leu Pro
        50                  55                  60

Asn Leu Gly Asn Leu Thr Gln Gln Phe Gly Gly Ser Ser Gly Ala Phe
65                  70                  75                  80

Pro Gln Phe Ser Ile Pro Ser Trp Thr Asn Phe Thr Asp Ala Phe Thr
                85                  90                  95

Ser Ile Leu Pro Phe Phe Gly Asn Gly Gln Gly Gly Phe Pro Phe
            100                 105                 110

Phe Gly

<210> SEQ ID NO 61
<211> LENGTH: 122
<212> TYPE: PRT
<213> ORGANISM: Anopheles gambiae
```

```
<220> FEATURE:
<221> NAME/KEY: misc_feature
<222> LOCATION: (39)..(39)
<223> OTHER INFORMATION: Xaa can be any naturally occurring amino acid

<400> SEQUENCE: 61

Met Thr Pro Leu Ile Ala Thr Leu Ala Ala Cys Ala Leu Thr Leu Ser
1               5                   10                  15

Ile Val His Ser Arg Gly Leu Pro Glu Ser Ser Asp Lys Leu Glu Ala
            20                  25                  30

Cys Gly Gln His Tyr Gly Xaa Leu Leu Lys Ala Ser Thr Thr Trp Asn
        35                  40                  45

Glu Lys Glu Cys Asn Gly Ser Thr Lys Leu Ala Ala Cys Val Val Ser
50                  55                  60

Glu His Glu Gln Ala Tyr Arg Glu Leu Lys Gln Arg Cys Gln Glu Ala
65                  70                  75                  80

His Asp Glu Arg Thr Ala Lys Val Asn Ala Ile Tyr Glu Lys Leu Pro
                85                  90                  95

Ala Tyr Leu Ser Glu Val Ser Ala Arg Val Asn Val Leu Gln Val Ser
            100                 105                 110

Leu Gln His Asp Leu Pro Asn Leu Gln Glu
        115                 120

<210> SEQ ID NO 62
<211> LENGTH: 124
<212> TYPE: PRT
<213> ORGANISM: Anopheles gambiae

<400> SEQUENCE: 62

Pro Asp Val Ala Glu Pro Leu Val His His Leu Arg His Leu Arg
1               5                   10                  15

Val Leu Ala Ala Ala Ala Asp His His Leu Leu Val His Leu His Pro
            20                  25                  30

Glu Gly Cys Val Arg Ser Arg Glu Glu His Ala Arg Ala Gly Gln Glu
        35                  40                  45

Gly Asn Val Ala Ser Leu Arg Thr Gln Glu Ala Gln Asn Thr Ser Thr
50                  55                  60

Glu Met Lys Leu Ala Lys Val Ala Leu Val Thr Ile Ser Leu Trp Phe
65                  70                  75                  80

Met Ala Trp Thr Pro Tyr Leu Val Ile Asn Phe Thr Gly Ile Phe Lys
                85                  90                  95

Ala Ala Pro Ile Ser Pro Leu Ala Thr Ile Arg Gly Ser Leu Phe Ala
            100                 105                 110

Lys Ala Asn Ala Val Tyr Asn Pro Ile Val Tyr Gly
        115                 120

<210> SEQ ID NO 63
<211> LENGTH: 144
<212> TYPE: PRT
<213> ORGANISM: Anopheles gambiae

<400> SEQUENCE: 63

Met Ala Thr Thr Trp Ile Pro Thr Ser Val His Gly Pro Tyr Pro Pro
1               5                   10                  15

His Met Val Pro Gly Gly Val Asp Ser Asp Gly Ala Gln Ile Phe Val
            20                  25                  30

Gly Arg Ala His His Ala Gly Asp Leu Leu Pro Ala Lys Val Ile Pro
        35                  40                  45
```

Asp Lys Thr Ala Ala Tyr Val Ala Tyr Gly Gly Gln Glu Thr Leu Val
        50                  55                  60

Glu His Val Glu Val Leu Val His Lys Gln Leu Ile Trp Asp Thr Ala
 65                  70                  75                  80

Ser Ala Gly Gln Val Pro Leu Gly Ala Val Gly Gly His Thr Ser
                85                  90                  95

Asp Gly Glu Ile Leu Tyr Val Gly Arg Ala Tyr His Glu Gly Ser Gln
                100                 105                 110

Thr Ile Gly Lys Val Gln Cys Ser His Asn Cys Ile Tyr Ile Pro Tyr
            115                 120                 125

Gly Gly Ala Glu Val Ser Val Pro Thr Tyr Glu Val Leu Cys Glu Arg
        130                 135                 140

<210> SEQ ID NO 64
<211> LENGTH: 150
<212> TYPE: PRT
<213> ORGANISM: Anopheles gambiae

<400> SEQUENCE: 64

Met Phe Lys Lys Leu Leu Leu Ser Val Gly Leu Val Trp Cys Leu Ile
 1               5                  10                  15

Ser Leu Gly Gln Ala Arg Lys Glu Ser Thr Val Glu Glu Cys Glu Lys
                20                  25                  30

Asn Ile Gly Asp Ser Leu Lys Asp Arg Val Cys Glu Leu Arg Gln Tyr
            35                  40                  45

Thr Pro Val Ser Ser Asp Asp Met Asp Lys His Met Gln Cys Val Leu
 50                  55                  60

Glu Val Val Gly Phe Val Asp Gly Asn Gly Glu Val Lys Glu Ser Val
 65                  70                  75                  80

Leu Leu Glu Leu Leu Gln Arg Val Asp Ser Gly Val Asn His Ala Ala
                85                  90                  95

Asn Met Lys Lys Cys Val Thr Glu Ala Ser Thr Ser Gly Ser Asp Lys
                100                 105                 110

Lys Ala Asn Thr Phe Tyr Thr Cys Phe Leu Gly Thr Ser Ser Leu Ala
            115                 120                 125

Gly Phe Lys Asn Ala Val Asp Tyr Asp Glu Leu Leu Lys Ala Gly Lys
        130                 135                 140

Met Gln Thr Ser Asp Pro
145                 150

<210> SEQ ID NO 65
<211> LENGTH: 156
<212> TYPE: PRT
<213> ORGANISM: Anopheles gambiae
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid

<400> SEQUENCE: 65

Met Phe Gly Lys Leu Leu Pro Cys Ala Ile Leu Leu Trp Cys Leu Phe
 1               5                  10                  15

Ser Leu Gly Gln Ala Arg Gln Glu Glu Thr Val Glu Glu Cys Glu Arg
                20                  25                  30

-continued

Asn Ile Pro Ala Ser Leu Lys Glu Arg Val Cys Glu Leu Arg Gln Tyr
               35                  40                  45

Thr Pro Val Gln Gly Lys Asp Met Asp Ser His Met Gln Cys Val Leu
 50                  55                  60

Glu Val Leu Gly Phe Val Glu Asp Asn Gly Glu Leu Val Phe Gln Glu
 65                  70                  75                  80

Leu Leu Gly Val Leu Lys Met Val Asp Pro Asp Gly Asp His Ala Gly
                 85                  90                  95

Ser Met Lys Lys Cys Asn Gly Glu Glu Lys Val Asp Thr Ser Ser
                100                 105                 110

Lys Ala Asn Thr Phe Tyr Thr Cys Phe Leu Gly Thr Ser Ser Ala Gln
                115                 120                 125

Ala Phe Lys Tyr Ala Val Asp Tyr Val Xaa Ala Xaa Arg Ala Gly Lys
                130                 135                 140

Leu Asp Met Gly Thr Thr Phe Asn Ala Gly Gln Val
145                 150                 155

<210> SEQ ID NO 66
<211> LENGTH: 178
<212> TYPE: PRT
<213> ORGANISM: Anopheles gambiae

<400> SEQUENCE: 66

Ala Gly Gly Phe Ser Leu Phe Glu Ala Leu Lys Gln Thr Thr Thr Arg
 1               5                  10                  15

Gly Glu Met Phe Arg Arg Lys Leu Thr Pro Thr Val Val Val Leu
                 20                  25                  30

Leu Cys Leu Thr Phe Val Ala Asp Ala Leu Thr Ile Gln Glu Leu Arg
                 35                  40                  45

Ala Gln Ile Ala Gln Gln Arg Ile Gln Gln Arg Tyr Gly Val Thr Val
     50                  55                  60

Ala Thr Thr Ser Ala Ala Thr Thr Thr Ala Thr Thr Ser Ala Ala
 65                  70                  75                  80

Thr Thr Ser Glu Ala Thr Thr Thr Ala Ala Ser Thr Thr Gln Ala
                 85                  90                  95

Ser Asp Ser Asp Asn Thr Thr Thr Thr Ala Glu Ala Thr Thr Thr Thr
                100                 105                 110

Glu Ala Gln Thr Thr Ser Ser Ser Asp Asn Ser Thr Thr Thr Glu Ala
                115                 120                 125

Ala Ala Thr Thr Thr Ala Ala Ser Glu Thr Thr Ala Asp Ser Ser Ser
                130                 135                 140

Thr Gly Thr Thr Ser Val Glu Ala Gly Leu Arg Ala Gln Tyr Arg Asp
145                 150                 155                 160

Gln Val Arg Gln Gln Ala Ile Glu Arg Ala Leu Ala Arg Ala Ala Ala
                165                 170                 175

Phe Gly

<210> SEQ ID NO 67
<211> LENGTH: 163
<212> TYPE: PRT
<213> ORGANISM: Anopheles gambiae

<400> SEQUENCE: 67

Met Arg Leu Phe Ala Ile Thr Cys Leu Leu Phe Ser Ile Val Thr Val
 1               5                  10                  15

Ile Gly Ala Glu Phe Ser Ala Glu Asp Cys Arg Glu Leu Gly Leu Ile

```
                    20                  25                  30
Lys Ser Gln Leu Phe Cys Ser Ala Cys Ser Ser Leu Ser Asp Tyr Gly
            35                  40                  45

Leu Ile Glu Leu Lys Glu His Cys Leu Glu Cys Cys Gln Lys Asp Thr
        50                  55                  60

Glu Ala Asp Ser Lys Leu Lys Val Tyr Pro Ala Val Leu Glu Val
65                  70                  75                  80

Cys Thr Cys Lys Phe Gly Ala Tyr Pro Gln Ile Gln Ala Phe Ile Lys
                85                  90                  95

Ser Asp Arg Pro Ala Lys Phe Pro Asn Leu Thr Ile Lys Tyr Val Arg
            100                 105                 110

Gly Leu Asp Pro Ile Val Lys Leu Met Asp Glu Gln Gly Thr Val Lys
            115                 120                 125

Glu Thr Leu Ser Ile Asn Lys Trp Asn Thr Asp Thr Val Gln Glu Phe
        130                 135                 140

Phe Glu Thr Arg Leu Ala Lys Val Glu Asp Asp Tyr Ile Lys Thr
145                 150                 155                 160

Asn Arg Val
```

```
<210> SEQ ID NO 68
<211> LENGTH: 182
<212> TYPE: PRT
<213> ORGANISM: Anopheles gambiae

<400> SEQUENCE: 68
```

```
Met Ala Gly Ala Ile Thr Tyr Ile Cys Phe Ile Leu His Gly Val Ser
1               5                   10                  15

Glu Ile Ile Pro Gln Gln Gln Lys Lys Thr Met Lys Phe Leu Leu Leu
            20                  25                  30

Val Ala Ser Val Leu Cys Leu Val Leu Ile Val Ser Ala Arg Pro Ala
        35                  40                  45

Asp Asp Thr Ser Asp Gln Glu Ser Ser Thr Glu Leu Ser Asp Asp Ala
    50                  55                  60

Gly Ala Glu Glu Gly Ala Glu Asp Ala Gly Ser Asp Ala Glu Ala Asp
65                  70                  75                  80

Ala Gly Ala Ala Asp Gly Glu Gly Ala Thr Asp Thr Glu Ser Gly
                85                  90                  95

Ala Glu Gly Asp Asp Ser Glu Met Asp Ser Ala Met Lys Glu Gly Glu
            100                 105                 110

Glu Gly Ala Gly Ser Asp Asp Ala Val Ser Gly Ala Asp Asp Glu Thr
        115                 120                 125

Glu Glu Ser Lys Asp Asp Ala Glu Glu Asp Ser Glu Glu Gly Gly Glu
    130                 135                 140

Glu Gly Gly Asp Ser Ala Ser Gly Gly Glu Gly Gly Glu Lys Glu Ser
145                 150                 155                 160

Pro Arg Asn Thr Tyr Arg Gln Val His Lys Leu Leu Lys Ile Met
                165                 170                 175

Lys Val Asp Thr Lys Asp
            180
```

```
<210> SEQ ID NO 69
<211> LENGTH: 166
<212> TYPE: PRT
<213> ORGANISM: Anopheles gambiae

<400> SEQUENCE: 69
```

```
Met Glu Trp Arg Tyr Phe Val Val Ile Ala Leu Ile Cys Pro Leu Ile
1               5                   10                  15

Ile Val Glu Thr Leu Ala Val Ser Asp Cys Val Arg His Val Ser Glu
            20                  25                  30

Ser Ala Arg Asn Thr Val Cys Asp Val Arg Gln Tyr Arg Val Thr Lys
        35                  40                  45

Gly Val Glu Ala Asp Arg Tyr Val Gln Cys Phe Met Thr Ala Leu Gly
    50                  55                  60

Phe Ala Asp Glu Ser Gly Ser Ile Gln Arg Ser Asn Val Leu Thr Ala
65                  70                  75                  80

Leu Asp Ala Val Glu Thr His Asp Gly Val Tyr Thr Asp Ala Val Asp
                85                  90                  95

Val Cys Leu Ser Lys Ala Lys Lys Leu Pro Gly Thr Glu Arg Ser Gly
            100                 105                 110

Tyr Phe Phe Ser Cys Met Leu Arg Thr Glu Ser Ala Leu Asn Phe Arg
        115                 120                 125

Asp Ala Val Glu Leu Gln Glu Leu Arg Val Ala Ser Lys Trp Pro Glu
    130                 135                 140

Gly Glu Arg Phe Asp Arg Ser Lys Val Gln Gln Met Met Arg Glu Leu
145                 150                 155                 160

Asn Ser Gln Leu Arg Cys
                165

<210> SEQ ID NO 70
<211> LENGTH: 161
<212> TYPE: PRT
<213> ORGANISM: Anopheles gambiae

<400> SEQUENCE: 70

Gly Arg Glu Ala Ile Glu Thr Met Arg Thr Glu Gln Arg Asn His Arg
1               5                   10                  15

Gln Gln Leu Leu Leu Leu Tyr Leu Asp Ala Ala Asp Leu Arg Arg Ala
            20                  25                  30

Leu His Gln Tyr Gln Leu Leu Ala Ala Gln Gly Asp Arg His Leu Pro
        35                  40                  45

Gln Gln Ile Val Lys Phe Val Tyr Ala Ala Pro Arg His Glu Asn Arg
    50                  55                  60

Arg Leu Glu Asn Leu Leu Asp Leu Val Arg Gln Leu Pro Ala Arg Gln
65                  70                  75                  80

Asp Gln Arg Thr Leu Tyr Gln Leu Leu Gln Pro Glu Ile Met Lys Arg
                85                  90                  95

Pro Ala Gln Asn Gln Ser Thr Leu Ala Met Leu Thr Ala Leu Glu Met
            100                 105                 110

Gly Gln Val Val Glu Gly Asn Gly Glu Leu Lys Lys Gln Gln Asp Ala
        115                 120                 125

Met Tyr Gln Leu Val Leu Lys Arg Trp Met Phe Leu Cys Leu Ala Gly
    130                 135                 140

Gln Tyr Arg Glu Ile Val Gln Phe Ala Thr Lys His Pro Arg Leu Phe
145                 150                 155                 160

Glu

<210> SEQ ID NO 71
<211> LENGTH: 178
<212> TYPE: PRT
<213> ORGANISM: Anopheles gambiae
```

<400> SEQUENCE: 71

```
Met Ala Ile Trp Ile Val Cys Ala Thr Leu Leu Leu Ala Val Leu Ser
1               5                   10                  15

Val Val Ser Val Gly Gly Gln Tyr Cys Ser Ser Asp Leu Cys Pro Arg
            20                  25                  30

Gly Gly Pro His Val Gly Cys Asn Pro Pro Ser Ser Ser Gly Gly Pro
            35                  40                  45

Thr Cys Gln Gly Lys Gln Lys Ala Arg Lys Val Leu Leu Thr Pro Ala
50                  55                  60

Leu Gln Ala Tyr Ile Met Asp Glu His Asn Leu Asn Arg Ser Asn Ile
65                  70                  75                  80

Ala Leu Gly Arg Ile Arg Pro Tyr Pro Ser Ala Val Lys Met Pro Thr
                85                  90                  95

Leu Thr Trp Asp Pro Glu Leu Ala Ser Leu Ala Asp Ala Asn Ala Arg
            100                 105                 110

Ser Cys Asn Tyr Gly His Asp Arg Cys Arg Ala Thr Lys Lys Phe Pro
        115                 120                 125

Tyr Ala Gly Gln Asn Ile Ala Ile Thr Gln Phe Phe Gly Tyr Arg Phe
130                 135                 140

Thr Glu Lys Asp Leu Ile His Lys Phe Val Ser Ser Trp Trp Ser Glu
145                 150                 155                 160

Tyr Leu Asp Ala Arg Pro Glu His Val Arg Lys Tyr Pro Ser Ser Tyr
                165                 170                 175

Ser Gly
```

<210> SEQ ID NO 72
<211> LENGTH: 238
<212> TYPE: PRT
<213> ORGANISM: Artificial Sequence
<220> FEATURE:
<223> OTHER INFORMATION: Synthetic construct

<400> SEQUENCE: 72

```
Met Lys Leu Ala Ser Ser Glu Asn Val Ile Thr Glu Phe Met Arg Phe
1               5                   10                  15

Lys Val Arg Met Glu Gly Thr Val Asn Gly His Glu Phe Glu Ile Glu
            20                  25                  30

Gly Glu Gly Glu Gly Arg Pro Tyr Glu Gly His Asn Thr Val Lys Leu
        35                  40                  45

Lys Val Thr Lys Gly Gly Pro Leu Pro Phe Ala Trp Asp Ile Leu Ser
50                  55                  60

Pro Gln Phe Gln Tyr Gly Ser Lys Val Tyr Val Lys His Pro Ala Asp
65                  70                  75                  80

Ile Pro Asp Tyr Lys Lys Leu Ser Phe Pro Glu Gly Phe Lys Trp Glu
                85                  90                  95

Arg Val Met Asn Phe Glu Asp Gly Gly Val Ala Thr Val Thr Gln Asp
            100                 105                 110

Ser Ser Leu Gln Asp Gly Cys Phe Ile Tyr Lys Val Lys Phe Ile Gly
        115                 120                 125

Val Asn Phe Pro Ser Asp Gly Pro Val Met Gln Lys Lys Thr Met Gly
130                 135                 140

Trp Glu Ala Ser Thr Glu Arg Leu Tyr Pro Arg Asp Gly Val Leu Lys
145                 150                 155                 160

Gly Glu Thr His Lys Ala Leu Lys Leu Lys Asp Gly Gly His Tyr Leu
```

```
                165                 170                 175
Val Glu Phe Lys Ser Ile Tyr Met Ala Lys Lys Pro Val Gln Leu Pro
            180                 185                 190

Gly Tyr Tyr Tyr Val Asp Ala Lys Leu Asp Ile Thr Ser His Asn Glu
            195                 200                 205

Asp Tyr Thr Ile Val Glu Gln Tyr Glu Arg Thr Gly Arg His His
            210                 215                 220

Leu Phe Leu Arg Ser Arg Ala Pro Pro Pro Pro Leu Thr
225                 230                 235

<210> SEQ ID NO 73
<211> LENGTH: 269
<212> TYPE: PRT
<213> ORGANISM: Anopheles gambiae

<400> SEQUENCE: 73

Met Ala Gly Gln Arg His Leu Ile Glu Gln Ala Trp Gln Tyr Gly Ala
1               5                   10                  15

Gln Leu Gln His Glu Leu Met Leu Thr Ser Met Glu Ser Asp Arg Val
            20                  25                  30

Gln Arg Ala Leu Val Leu His Ser Met Leu Val Asn Ala Ser Leu Ala
        35                  40                  45

Glu Met Val Lys Glu Ser Tyr Gln Thr His Gly Ala Asp Gly Arg Met
50                  55                  60

Val Val Arg Met Leu Lys Phe Val Arg Leu Leu Pro Gly Ala Asp Glu
65                  70                  75                  80

Arg Val Ala Val Tyr Lys Gln Leu Ala Glu Leu Leu Lys Ser Asn Gly
                85                  90                  95

Gln Asp Gly Arg Phe Pro Ala Val Ile Phe Ser Thr Ala Val Arg Gln
            100                 105                 110

Leu Glu Asp Arg Tyr Lys Pro Asp His Ala Gln Tyr Glu Gly Lys Val
        115                 120                 125

Val Glu Arg Trp Leu Ala Glu Leu Gln Ala Gly Thr Phe His Glu Val
130                 135                 140

Val Glu Phe Ala Arg Asp Tyr Pro Glu Tyr Phe Ala Arg Val Glu Glu
145                 150                 155                 160

Pro Leu Tyr Glu Thr Leu Lys Gln Gln Trp Ser Ala Glu Gly Leu Asp
                165                 170                 175

Arg Met Val Ser Phe Pro Asn Ala Leu Pro Val Gly Val Gln Arg Val
            180                 185                 190

Arg Ala Leu Arg Ala Leu Leu Glu Thr Leu Leu Gln His Gln Gly Glu
        195                 200                 205

Gln Asn Asn Asp Val Tyr Leu Ile Arg Leu Ala His Glu Thr Gly Arg
    210                 215                 220

Val Glu Ala Thr Val Gly Gln Ala Asp Ala Ala Val Arg Gln Ala Leu
225                 230                 235                 240

Asp Asp Val Lys Lys Leu Phe Glu Gln Phe Lys Tyr Gln Arg Gly Phe
                245                 250                 255

Pro Asp Tyr Glu Ala Leu Tyr Lys Leu Phe Lys Gly Leu
            260                 265

<210> SEQ ID NO 74
<211> LENGTH: 311
<212> TYPE: PRT
<213> ORGANISM: Anopheles gambiae
```

<400> SEQUENCE: 74

Met Ile Val Pro Arg Val Leu Leu Phe Ile Leu Leu Glu Leu Phe Val
1               5                   10                  15

Gln Ala Thr Gln Ala Phe Lys Ala Leu Asp Pro Glu Glu Ala Trp Tyr
            20                  25                  30

Val Tyr Glu Arg Cys His Glu His Leu Pro Ser Gly Pro Asn Arg
        35                  40                  45

Glu Thr Tyr Leu Lys Thr Trp Lys Phe Trp Lys Leu Glu Pro Asn Asp
    50                  55                  60

Ala Val Thr His Cys Tyr Val Lys Cys Thr Leu Ala Gly Leu Gln Met
65                  70                  75                  80

Tyr Asp Glu Lys Thr Asn Thr Phe Lys Pro Glu Thr Val Pro Val Gln
                85                  90                  95

His Glu Ala Tyr Lys Ser Phe Thr Glu Val Ser Ser Lys Val Asn
            100                 105                 110

Glu Leu Gln Gln Ala Leu Ser Ser Leu Asn Ala Gly Ser Gly Ser Cys
        115                 120                 125

Ala Glu Val Phe Asn Ala Tyr Leu Pro Val His Asn Lys Tyr Ile Gly
130                 135                 140

Val Ser Arg Lys Ile Tyr His Gly Thr Val Asp Ser Val Ala Lys Ile
145                 150                 155                 160

Tyr Glu Ala Lys Pro Glu Ile Lys Lys Gln Glu Glu Ser Phe Phe Ala
                165                 170                 175

Tyr Cys Ala Lys Lys Ala Leu Gly Ala Asn Gly Lys Glu Gly Tyr Lys
            180                 185                 190

Lys Ile Arg Asp Tyr Glu Leu Ala Asp Ser Ala Glu Phe Arg Asn Ala
        195                 200                 205

Met Asp Cys Val Phe Arg Gly Phe Arg Tyr Met Asp Asp Ser Gly Leu
210                 215                 220

Lys Val Asp Glu Val Val Arg Asp Phe Asn Leu Ile Asn Lys Ser Asp
225                 230                 235                 240

Leu Glu Pro Glu Val Arg Ser Val Leu Ala Ser Cys Thr Gly Thr His
                245                 250                 255

Ala Tyr Asp Tyr Tyr Ser Cys Leu Leu Asn Ser Ser Val Lys Glu Asp
            260                 265                 270

Phe Arg Asn Ala Phe Tyr Phe His Glu Leu Arg Ser Ala Asn Tyr Gly
        275                 280                 285

Tyr Leu Ala Met Gly Lys Val Tyr Gly Gly Pro Glu Lys Val Lys Glu
290                 295                 300

Glu Leu Lys Lys Leu Asn Tyr
305                 310

<210> SEQ ID NO 75
<211> LENGTH: 76
<212> TYPE: PRT
<213> ORGANISM: Anopheles gambiae

<400> SEQUENCE: 75

Met Cys Lys Phe Tyr Arg Leu Ile Ser Thr Leu Leu Val Val Val
1               5                   10                  15

Ile Ala Pro Arg His Gln Cys Ser Pro Phe Phe Gln Tyr Asn Arg
            20                  25                  30

Pro Tyr Leu Ser Gln Pro Ser Gln Leu Ala Ser Thr Ala Ala Asn
        35                  40                  45

Val Val Gln Arg Ser Asn Val Thr Val Ala Leu Gly Asn Arg Ile Asn
50                  55                  60

Thr Asp Thr Ala Leu Asp Asp Tyr Gly Thr Arg Val
65                  70                  75

<210> SEQ ID NO 76
<211> LENGTH: 131
<212> TYPE: PRT
<213> ORGANISM: Anopheles gambiae

<400> SEQUENCE: 76

Met Gly Arg Val Arg Thr Lys Thr Ile Lys Lys Ala Ser Lys Val Ile
1               5                   10                  15

Ile Glu Lys Tyr Tyr Thr Arg Leu Thr Met Asp Phe Asp Thr Asn Lys
                20                  25                  30

Arg Ile Val Glu Glu Val Ala Ile Ile Pro Thr Lys Pro Leu Arg Asn
            35                  40                  45

Lys Ile Ala Gly Phe Val Thr His Leu Met Lys Arg Leu Arg His Ser
    50                  55                  60

Gln Val Arg Gly Ile Ser Ile Lys Leu Gln Glu Glu Arg Glu Arg
65                  70                  75                  80

Arg Asp Asn Tyr Val Pro Asp Val Ser Ala Leu Glu Gln Asp Ile Ile
                85                  90                  95

Glu Val Asp Pro Glu Thr Lys Glu Met Leu Lys His Leu Asp Phe Asn
            100                 105                 110

Asn Ile Val Val Gln Leu Thr Asn Pro Thr Ala Pro Gly Tyr Ser Asn
    115                 120                 125

Arg Arg Asn
    130

<210> SEQ ID NO 77
<211> LENGTH: 145
<212> TYPE: PRT
<213> ORGANISM: Anopheles gambiae

<400> SEQUENCE: 77

Met His Ala Lys Pro Ala Phe Val Leu Ile Ala Leu Gly Val Ile Cys
1               5                   10                  15

Leu Leu Gln Thr Thr Pro Thr Ser Ala Ser Thr Asn His Val Gln Gln
                20                  25                  30

Leu Met Lys Val Phe Arg Ser Met Thr Gln Asn Phe Asp Tyr Thr Lys
            35                  40                  45

Lys Pro Ser Tyr Leu Gln Arg Ala Lys Tyr Gly Val Gln Asn Gln Leu
    50                  55                  60

Arg Asn Pro Leu Val Gln Lys Ala Gly Asn Leu Pro Lys Ser Ala Lys
65                  70                  75                  80

Leu Ser Asp Gly Cys Leu Lys Gln Met Val Ala Arg Val Thr Asp Leu
                85                  90                  95

Glu Ala Ser Phe Tyr Ala Ser Phe Ser Tyr Asn Cys His Asp His Asp
            100                 105                 110

Gln Tyr Ser Met Glu Cys Leu Glu Ala Ala Glu Pro Lys Tyr Leu Asp
    115                 120                 125

Gly Leu Lys Thr Leu Ala Asp Glu Thr Ala Gln Cys Met Arg Asp Gln
    130                 135                 140

Gln
145

<210> SEQ ID NO 78
<211> LENGTH: 148
<212> TYPE: PRT
<213> ORGANISM: Anopheles gambiae

<400> SEQUENCE: 78

```
Met Pro Lys Asn Lys Gly Lys Gly Gly Lys Asn Arg Arg Gly Lys
1               5                   10                  15

Asn Glu Asn Glu Ser Glu Lys Arg Glu Leu Ile Phe Lys Glu Asp Glu
            20                  25                  30

Gln Glu Tyr Ala Gln Val Thr Lys Met Leu Gly Asn Gly Arg Leu Glu
        35                  40                  45

Ala Met Cys Phe Asp Gly Val Lys Arg Leu Cys His Ile Arg Gly Lys
    50                  55                  60

Leu Arg Lys Lys Val Trp Ile Asn Gln Gly Asp Ile Ile Leu Ile Gly
65                  70                  75                  80

Leu Arg Asp Tyr Gln Asp Ser Lys Ala Asp Val Ile Leu Lys Tyr Thr
                85                  90                  95

Pro Asp Glu Ala Arg Asn Leu Lys Thr Tyr Gly Glu Phe Pro Glu Ser
            100                 105                 110

Val Arg Ile Asn Glu Thr Val Thr Phe Val Glu Asn Asp Met Asp Asp
        115                 120                 125

Asp Ile Glu Phe Gly Asp Asp Tyr Ser Ser Glu Glu Gly Asp Ala
    130                 135                 140

Ile Asp Ala Ile
145
```

<210> SEQ ID NO 79
<211> LENGTH: 168
<212> TYPE: PRT
<213> ORGANISM: Anopheles gambiae

<400> SEQUENCE: 79

```
Met Lys Leu Phe Leu Thr Leu Leu Ser Thr Leu Ser Val Ala Met Val
1               5                   10                  15

Phe Ala Leu Pro Ala His His His Ser Arg Gly Gly Asp Gly Ser Ser
            20                  25                  30

Ala Asn Ser Thr Gly Asn Ser Asp Asn Asn Ser Ala Gly Val Pro Asp
        35                  40                  45

Phe Gly Phe Asn Ser Gln Ser Asn Val Pro Gly Phe Gly Asn Gly Gln
    50                  55                  60

Gln Pro Gly Gln Gln Gln Gln Gly Gln Gln Gly Gln Gly Phe Pro Phe
65                  70                  75                  80

Phe Gly Gln Gly Gln Ser Gly Phe Pro Ser Phe Gly Asn Arg Leu Gln
                85                  90                  95

Pro Phe Phe Gly Gln Asn Gln Gln Gly Gln Asp Gly Asp Ala Gln Gln
            100                 105                 110

Gly Arg Gly Val Pro Phe Phe Gly Gln Gly Gly Gln Gly Gly Ile
        115                 120                 125

Pro Ser Phe Gly Ser Gly Gln Gln Asn Gly Gly Val Pro Phe Leu Gly
    130                 135                 140

Asn Gly Gln Gly Gln Ser Gly Phe Pro Ser Phe Gly Asn Gly Gln Gln
145                 150                 155                 160

Gly Gly Asn Phe Pro Phe Phe Gly
                165
```

<210> SEQ ID NO 80
<211> LENGTH: 166
<212> TYPE: PRT
<213> ORGANISM: Anopheles gambiae

<400> SEQUENCE: 80

Met Lys Leu Tyr Ala Phe Ala Leu Val Leu Cys Val Gly Leu Ala Val
1               5                   10                  15

Gly Ala Glu Val Asp Ser Val Pro Glu Val Pro Ser Asp Leu Gln Gln
            20                  25                  30

Gln Leu Asp Glu Leu Gln Leu Ala Asp Lys Pro Glu Ala Pro Val Asp
        35                  40                  45

Asp Ala Glu Gln Pro Leu Pro Pro Asn Gly Asp Glu Leu Pro Glu Asp
    50                  55                  60

Ala Pro Glu Pro Val Pro Glu Asp Gly Ser Pro Asp Glu Glu His Leu
65                  70                  75                  80

Glu Glu Glu Gln Glu Glu Glu Ala Glu Ala Asp Glu Glu Glu Ala Asp
                85                  90                  95

Glu Ser Glu Ser Glu Glu Ser Glu Ser Asp Glu Leu Glu Glu Ala
            100                 105                 110

Arg Leu Val Ala Glu Glu Leu Glu Glu Arg Gln Gln Glu Leu Asp Tyr
        115                 120                 125

Leu Lys Arg Tyr Leu Val Gly Arg Leu Gln Ala Val Ala Ile Leu Asp
    130                 135                 140

Arg Arg Val Arg Pro Ala Val Ile Arg Arg Pro Trp Ile Arg Arg Pro
145                 150                 155                 160

Trp Ile Arg Arg Pro Gly
                165

<210> SEQ ID NO 81
<211> LENGTH: 165
<212> TYPE: PRT
<213> ORGANISM: Anopheles gambiae

<400> SEQUENCE: 81

Met Ile Arg Gln Val Ile Ile Ser Tyr Phe Leu Thr Val Cys Leu Leu
1               5                   10                  15

Ala Leu Val Gln Ser Glu Thr Val Gln Asp Cys Glu Asn Lys Leu Pro
            20                  25                  30

Pro Ser Leu Lys Ser Arg Leu Cys Glu Ile Arg Arg Tyr Glu Ile Ile
        35                  40                  45

Glu Gly Pro Glu Met Asp Lys His Ile His Cys Val Met Arg Ala Leu
    50                  55                  60

Asp Phe Val Tyr Glu Asp Gly Arg Gly Asp Tyr His Lys Leu Tyr Asp
65                  70                  75                  80

Pro Leu Asn Ile Ile Glu Leu Asp Lys Arg His Asp Val Asn Leu Glu
                85                  90                  95

Lys Cys Ile Gly Glu Cys Val Gln Val Pro Thr Ser Glu Arg Ala His
            100                 105                 110

Val Phe Tyr Lys Cys Leu Leu Lys Ser Thr Thr Gly Arg Thr Phe Lys
        115                 120                 125

Lys Val Phe Asp Leu Met Glu Leu Lys Lys Ala Gly Lys Val Pro Gln
    130                 135                 140

His Gln Arg Tyr Thr Ala Glu Phe Val Gln Ile Met Lys Asp Tyr Asp
145                 150                 155                 160

```
Lys Ala Leu Asn Cys
            165
```

<210> SEQ ID NO 82
<211> LENGTH: 224
<212> TYPE: PRT
<213> ORGANISM: Anopheles gambiae

<400> SEQUENCE: 82

```
Met Glu Ala Ile Ser Glu Ala Leu Gln Pro Tyr Lys Glu Gln Val Gly
1               5                   10                  15

Met Ala Ala Gly Ile Leu Thr Val Gly Gln Met Phe Ser Gly Cys Phe
            20                  25                  30

Val Cys Asn Asp Ile Arg Lys Lys Gly Thr Thr Asp Gly Phe Ser Ala
        35                  40                  45

Met Pro Phe Val Gly Gly Cys Gly Leu Thr Val Leu Phe Leu Gln His
    50                  55                  60

Gly Met Leu Met Asn Asp Ser Ala Met Thr Asn Ala Asn Leu Val Gly
65                  70                  75                  80

Leu Thr Ile Ser Leu Ala Tyr Ala Ile Phe Phe Leu Leu Tyr Thr Pro
                85                  90                  95

Pro Thr Gly Arg Ser Ser Tyr Trp Arg Gln Val Gly Gly Thr Ala Leu
            100                 105                 110

Phe Thr Ile Thr Leu Leu Gly Tyr Val Lys Val Glu Asn Pro Ser Val
        115                 120                 125

Val Glu Asp Arg Phe Gly Met Ile Ile Thr Val Leu Met Leu Ala Leu
    130                 135                 140

Ile Gly Gln Pro Leu Phe Gly Leu Pro Asp Ile Ile Arg Arg Lys Ser
145                 150                 155                 160

Thr Glu Gly Leu Pro Phe Ala Met Ile Leu Ser Gly Thr Ile Val Gly
                165                 170                 175

Leu Ser Trp Leu Leu Tyr Gly Val Ile Leu Asn Asn Val Phe Val Val
            180                 185                 190

Cys Gln Asn Leu Ala Ala Val Thr Leu Ser Gly Ile Gln Leu Ala Leu
        195                 200                 205

Phe Ala Ile Tyr Pro Ser Lys Ala Ala Pro Pro Ser Lys Lys Arg Glu
    210                 215                 220
```

<210> SEQ ID NO 83
<211> LENGTH: 228
<212> TYPE: PRT
<213> ORGANISM: Anopheles gambiae

<400> SEQUENCE: 83

```
Met Glu Ser Ile Ala Val Ala Leu Gln Pro Tyr Lys Asp Thr Val Gly
1               5                   10                  15

Leu Thr Ala Ala Ile Val Thr Val Val Gln Phe Phe Ser Gly Val Leu
            20                  25                  30

Ala Leu Asn Ala Ile Arg Arg Gln Gly Asn Thr Arg Gly Phe Ser Ala
        35                  40                  45

Leu Pro Phe Leu Gly Gly Thr Val Phe Cys Leu Leu Asn Ile Gln Phe
    50                  55                  60

Gly Gln Met Leu Arg Asp Asp Gly Met Ile Arg Val Asn Phe Ile Gly
65                  70                  75                  80

Leu Ala Leu Asn Leu Leu Tyr Val Cys Gly Phe Tyr Leu Tyr Thr Glu
                85                  90                  95
```

```
Gly Pro Ala Lys Thr Ala Val Trp Gly Gln Ile Gly Leu Ala Gly Ala
            100                 105                 110

Leu Thr Ala Gly Val Leu Ser Tyr Val Gln Tyr Glu Asp Pro Gln Leu
        115                 120                 125

Val Glu Phe Arg Phe Gly Leu Ile Leu Thr Gly Leu Leu Trp Thr Leu
130                 135                 140

Val Gly Met Pro Leu Leu Gly Leu Gly Asp Ile Leu Lys Lys Lys Ser
145                 150                 155                 160

Thr Glu Gly Leu Pro Phe Pro Ile Ile Phe Leu Gly Ala Val Val Ser
                165                 170                 175

Phe Ala Trp Leu Leu Tyr Gly Ile Ile Leu Arg Ser Asn Phe Leu Val
                180                 185                 190

Val Gln Asn Leu Met Ala Leu Ala Leu Ser Ala Val Gln Leu Ser Leu
        195                 200                 205

Phe Ile Ile Phe Pro Ser Gly Ala Ala Lys Pro Pro Pro Thr Pro Ala
210                 215                 220

Lys Lys Arg Asn
225

<210> SEQ ID NO 84
<211> LENGTH: 229
<212> TYPE: PRT
<213> ORGANISM: Anopheles gambiae

<400> SEQUENCE: 84

Met Asp Gly Ile Met Ser Lys Gly Ser Leu Ala Ser Leu Ala Thr Val
1               5                   10                  15

Ala Thr Val Leu Gln Phe Leu Thr Gly Thr Val Ile Cys Asn Arg Tyr
            20                  25                  30

Ile Arg Lys Lys Ser Thr Gly Asp Thr Ser Ala Phe Pro Phe Ile Ser
        35                  40                  45

Gly Phe Leu Ser Cys Phe Met Trp Leu Lys Tyr Gly Val Leu Thr Glu
    50                  55                  60

Glu Ser Thr Leu Ile Leu Val Asn Phe Ile Gly Ser Ala Leu Phe Phe
65                  70                  75                  80

Ser Tyr Thr Val Val Phe Phe Ile Phe Cys Val Asn Lys Arg Glu Val
                85                  90                  95

Ile Arg Gln Met Met Val Ile Ser Cys Ile Ile Leu Ser Ala Thr Leu
            100                 105                 110

Tyr Thr Leu Phe Glu Thr Asp Asp Glu Lys Ser Ile Arg Val Ile Gly
        115                 120                 125

Leu Leu Cys Cys Cys Leu Ala Val Leu Phe Phe Ala Ser Pro Leu Thr
130                 135                 140

Met Leu Ala His Val Ile Arg Thr Gln Asn Thr Asp Ser Leu Pro Phe
145                 150                 155                 160

Pro Ile Ile Met Ala Ser Phe Phe Val Cys Leu Leu Trp Thr Ala Tyr
                165                 170                 175

Gly Val Leu Ile Gly Asp Arg Phe Ile Gln Ile Pro Asn Leu Leu Gly
                180                 185                 190

Gly Ile Leu Ala Gly Ile Gln Leu Thr Leu Tyr Val Ile Tyr Pro Lys
        195                 200                 205

Lys Lys Ala Ser Phe Ser Gly Gly Pro Arg Tyr Ser Pro Leu Val Ser
210                 215                 220

Glu Asn Pro Ile Leu
225
```

<210> SEQ ID NO 85
<211> LENGTH: 115
<212> TYPE: PRT
<213> ORGANISM: Anopheles gambiae

<400> SEQUENCE: 85

Met Ala Ile Arg Val Glu Leu Leu Ala Met Val Leu Leu Pro Leu
1               5                   10                  15

Leu Leu Leu Glu Ser Val Val Pro Tyr Ala Ala Ala Glu Lys Val Trp
            20                  25                  30

Val Asp Arg Asp Lys Val Tyr Cys Gly His Leu Asp Cys Thr Arg Val
        35                  40                  45

Ala Thr Phe Lys Gly Glu Arg Phe Cys Thr Leu Cys Asp Thr Arg His
    50                  55                  60

Phe Cys Glu Cys Lys Glu Thr Arg Glu Pro Leu Pro Tyr Met Tyr Ala
65                  70                  75                  80

Cys Pro Gly Thr Glu Pro Cys Gln Ser Ser Asp Arg Leu Gly Ser Cys
                85                  90                  95

Ser Lys Ser Met His Asp Val Leu Cys Asp Arg Ile Asp Gln Ala Phe
            100                 105                 110

Leu Glu Gln
        115

<210> SEQ ID NO 86
<211> LENGTH: 35
<212> TYPE: PRT
<213> ORGANISM: Artificial Sequence
<220> FEATURE:
<223> OTHER INFORMATION: Immunogenic polypeptide

<400> SEQUENCE: 86

Met His Leu Thr Leu Phe Thr Val Ala Val Leu Leu Ala Ala Ala
1               5                   10                  15

Ala Leu Leu Leu Leu Pro Pro Ala Tyr Ser Thr Thr Leu Thr Pro
            20                  25                  30

Pro Ala Pro
        35

<210> SEQ ID NO 87
<211> LENGTH: 28
<212> TYPE: PRT
<213> ORGANISM: Artificial Sequence
<220> FEATURE:
<223> OTHER INFORMATION: Immunogenic polypeptide

<400> SEQUENCE: 87

Met Pro Leu Ser Tyr Cys His Leu Phe Leu Thr His Thr Leu Ala Arg
1               5                   10                  15

Ala Leu Ser Phe Ser Arg Ser Asp Cys Leu Lys Phe
            20                  25

<210> SEQ ID NO 88
<211> LENGTH: 27
<212> TYPE: PRT
<213> ORGANISM: Artificial Sequence
<220> FEATURE:
<223> OTHER INFORMATION: Immunogenic polypeptide

<400> SEQUENCE: 88

Met Lys Asn Val Phe Phe Ala Leu Leu Leu Val Val Leu Val Cys Cys

```
1               5                   10                  15
Leu Val Ser Val Gln Gly Asn Glu Ile Ile Gln
            20                  25
```

<210> SEQ ID NO 89
<211> LENGTH: 31
<212> TYPE: PRT
<213> ORGANISM: Artificial Sequence
<220> FEATURE:
<223> OTHER INFORMATION: Immunogenic polypeptide

<400> SEQUENCE: 89

```
Gly Ile Lys Leu Leu Val Leu Leu Ile Cys Leu Phe Phe Tyr His Thr
1               5                   10                  15

His Cys Thr Thr Ala Tyr Leu Trp Leu Ala Met Gly Val Glu Ala
            20                  25                  30
```

<210> SEQ ID NO 90
<211> LENGTH: 28
<212> TYPE: PRT
<213> ORGANISM: Artificial Sequence
<220> FEATURE:
<223> OTHER INFORMATION: Immunogenic polypeptide

<400> SEQUENCE: 90

```
Met Phe Leu Lys Gly Ser Phe Pro Arg Phe Gln Met Cys Val Met Leu
1               5                   10                  15

Ile Gly Phe Phe Ser Ser Ala Lys Cys Leu Met Cys
            20                  25
```

<210> SEQ ID NO 91
<211> LENGTH: 33
<212> TYPE: PRT
<213> ORGANISM: Artificial Sequence
<220> FEATURE:
<223> OTHER INFORMATION: Immunogenic polypeptide

<400> SEQUENCE: 91

```
Lys Gln Asn Asp Tyr Gln Ala Leu Leu Gly Leu Cys Cys Pro Trp Ile
1               5                   10                  15

Asp Leu Ala Ala Ala Asp Leu Pro Met Arg Arg His Ala Lys Ala Arg
            20                  25                  30

Glu
```

<210> SEQ ID NO 92
<211> LENGTH: 35
<212> TYPE: PRT
<213> ORGANISM: Artificial Sequence
<220> FEATURE:
<223> OTHER INFORMATION: Immunogenic polypeptide

<400> SEQUENCE: 92

```
Met Lys Phe Tyr Ser Val Gly Lys Leu Val Lys Val Leu Val Met
1               5                   10                  15

Ala Val Cys Cys Leu Leu Leu Cys Thr Ala Pro Thr Gly Ala Asp Pro
            20                  25                  30

Leu Pro Gly
        35
```

<210> SEQ ID NO 93
<211> LENGTH: 32
<212> TYPE: PRT
<213> ORGANISM: Artificial Sequence

```
<220> FEATURE:
<223> OTHER INFORMATION: Immunogenic polypeptide

<400> SEQUENCE: 93

Met Lys Phe Ala Phe Ala Phe Val Leu Ile Ala Leu Phe Ala Val Phe
1               5                   10                  15

Ala Val Ser Gln Ala Leu Pro Gln Pro Glu Gln Ala Ala Ala Ser Ser
            20                  25                  30

<210> SEQ ID NO 94
<211> LENGTH: 25
<212> TYPE: PRT
<213> ORGANISM: Artificial Sequence
<220> FEATURE:
<223> OTHER INFORMATION: Immunogenic polypeptide

<400> SEQUENCE: 94

Ser Asn Asp Gly Ala Ser Ala Ile Thr Lys Ile Val Leu Glu Leu Thr
1               5                   10                  15

Pro Glu Gln Ala Ala Ala Val Gln Lys
            20                  25

<210> SEQ ID NO 95
<211> LENGTH: 37
<212> TYPE: PRT
<213> ORGANISM: Artificial Sequence
<220> FEATURE:
<223> OTHER INFORMATION: Immunogenic polypeptide

<400> SEQUENCE: 95

Ala Ile Thr Leu Phe Ile Phe Leu Val Cys Cys Gln Ile Pro Leu Phe
1               5                   10                  15

Gly Ile Met Ser Ser Asp Ser Ala Asp Pro Phe Tyr Trp Ile Arg Val
            20                  25                  30

Ile Leu Ala Ser Asn
        35

<210> SEQ ID NO 96
<211> LENGTH: 25
<212> TYPE: PRT
<213> ORGANISM: Artificial Sequence
<220> FEATURE:
<223> OTHER INFORMATION: Immunogenic polypeptide

<400> SEQUENCE: 96

Met Gly Arg Val Met Cys Leu Leu Arg Leu Met Ser Thr Leu Leu Val
1               5                   10                  15

Val Leu Ser Ile Val Gly Lys Lys Thr
            20                  25

<210> SEQ ID NO 97
<211> LENGTH: 42
<212> TYPE: PRT
<213> ORGANISM: Artificial Sequence
<220> FEATURE:
<223> OTHER INFORMATION: Immunogenic polypeptide

<400> SEQUENCE: 97

Met Lys Leu Tyr Ser Gly Tyr Arg Leu Leu Val Leu Leu Val Met Thr
1               5                   10                  15

Val Cys Cys Leu Leu Leu Phe Ile Ala Pro Thr Gly Ala Asp Pro Leu
            20                  25                  30

Pro Gly Gln Thr Gln Arg Thr Leu Gly Tyr
```

<210> SEQ ID NO 98
<211> LENGTH: 39
<212> TYPE: PRT
<213> ORGANISM: Artificial Sequence
<220> FEATURE:
<223> OTHER INFORMATION: Immunogenic polypeptide

<400> SEQUENCE: 98

```
Cys Lys Met Tyr Cys Val Ile Lys Gly Lys Thr Gly Gly Tyr Cys Asn
1               5                   10                  15

Ser Glu Gly Leu Cys Thr Cys Arg Ala Glu Asp Leu His Phe Leu Leu
            20                  25                  30

Lys Pro Ile Ile Asn Lys Asp
        35
```

<210> SEQ ID NO 99
<211> LENGTH: 40
<212> TYPE: PRT
<213> ORGANISM: Artificial Sequence
<220> FEATURE:
<223> OTHER INFORMATION: Immunogenic polypeptide

<400> SEQUENCE: 99

```
Thr Val Asn Ala Glu Asp Pro Arg Thr Glu Leu Ile Gly Cys Gly Ser
1               5                   10                  15

Val Leu Phe His Leu Ala Ala Asn Arg Leu Ser Leu Gln Leu Glu Glu
            20                  25                  30

Phe Ala Val Cys Lys Arg Ser Asn
        35                  40
```

<210> SEQ ID NO 100
<211> LENGTH: 41
<212> TYPE: PRT
<213> ORGANISM: Artificial Sequence
<220> FEATURE:
<223> OTHER INFORMATION: Immunogenic polypeptide

<400> SEQUENCE: 100

```
Cys Val Ala Leu Ile Gly Leu Leu Leu Cys Ser Val Gln Ser Val Thr
1               5                   10                  15

Ala Asn Asp Pro Val Asp Ala Leu Gly Ala Cys Ser Gly Asn Leu Phe
            20                  25                  30

Gly Leu Leu Met Thr Arg Leu Gln Gln
        35                  40
```

<210> SEQ ID NO 101
<211> LENGTH: 34
<212> TYPE: PRT
<213> ORGANISM: Artificial Sequence
<220> FEATURE:
<223> OTHER INFORMATION: Immunogenic polypeptide

<400> SEQUENCE: 101

```
Met Ala Ser Lys Leu Phe Val Leu Ala Phe Leu Cys Leu Ala Leu Val
1               5                   10                  15

Val Val Val Gln Ser Ala Pro Gln Tyr Ala Arg Gly Asp Val Pro Thr
            20                  25                  30

Tyr Asp
```

<210> SEQ ID NO 102

```
<211> LENGTH: 42
<212> TYPE: PRT
<213> ORGANISM: Artificial Sequence
<220> FEATURE:
<223> OTHER INFORMATION: Immunogenic polypeptide

<400> SEQUENCE: 102

Met Lys Ser Met Leu Val Ala Phe Ala Thr Leu Ser Val Ala Leu Val
1               5                   10                  15

Val Val Val Ala Ile Pro Ala Asn Phe Asn Tyr Gly Gly Gly Gly Gly
                20                  25                  30

Tyr Phe Ile Asn Gly Thr Gly Gln Ser Phe
        35                  40

<210> SEQ ID NO 103
<211> LENGTH: 34
<212> TYPE: PRT
<213> ORGANISM: Artificial Sequence
<220> FEATURE:
<223> OTHER INFORMATION: Immunogenic polypeptide

<400> SEQUENCE: 103

Asn Ala Ile Tyr Glu Lys Leu Pro Ala Tyr Leu Ser Glu Val Ser Ala
1               5                   10                  15

Arg Val Asn Val Leu Gln Val Ser Leu Gln His Asp Leu Pro Asn Leu
                20                  25                  30

Gln Glu

<210> SEQ ID NO 104
<211> LENGTH: 34
<212> TYPE: PRT
<213> ORGANISM: Artificial Sequence
<220> FEATURE:
<223> OTHER INFORMATION: Immunogenic polypeptide

<400> SEQUENCE: 104

Ser Thr Glu Met Lys Leu Ala Lys Val Ala Leu Val Thr Ile Ser Leu
1               5                   10                  15

Trp Phe Met Ala Trp Thr Pro Tyr Leu Val Ile Asn Phe Thr Gly Ile
                20                  25                  30

Phe Lys

<210> SEQ ID NO 105
<211> LENGTH: 35
<212> TYPE: PRT
<213> ORGANISM: Artificial Sequence
<220> FEATURE:
<223> OTHER INFORMATION: Immunogenic polypeptide

<400> SEQUENCE: 105

Gly Asp Leu Leu Pro Ala Lys Val Ile Pro Asp Lys Thr Ala Ala Tyr
1               5                   10                  15

Val Ala Tyr Gly Gly Gln Glu Thr Leu Val Glu His Val Glu Val Leu
                20                  25                  30

Val His Lys
        35

<210> SEQ ID NO 106
<211> LENGTH: 31
<212> TYPE: PRT
<213> ORGANISM: Artificial Sequence
<220> FEATURE:
<223> OTHER INFORMATION: Immunogenic polypeptide
```

-continued

<400> SEQUENCE: 106

Asn Thr Phe Tyr Thr Cys Phe Leu Gly Thr Ser Ser Leu Ala Gly Phe
1               5                   10                  15
Lys Asn Ala Val Asp Tyr Asp Glu Leu Leu Lys Ala Gly Lys Met
            20                  25                  30

<210> SEQ ID NO 107
<211> LENGTH: 35
<212> TYPE: PRT
<213> ORGANISM: Artificial Sequence
<220> FEATURE:
<223> OTHER INFORMATION: Immunogenic polypeptide

<400> SEQUENCE: 107

Gln Cys Val Leu Glu Val Leu Gly Phe Val Glu Asp Asn Gly Glu Leu
1               5                   10                  15
Val Phe Gln Glu Leu Leu Gly Val Leu Lys Met Val Asp Pro Asp Gly
            20                  25                  30
Asp His Ala
        35

<210> SEQ ID NO 108
<211> LENGTH: 49
<212> TYPE: PRT
<213> ORGANISM: Artificial Sequence
<220> FEATURE:
<223> OTHER INFORMATION: Immunogenic polypeptide

<400> SEQUENCE: 108

Arg Arg Lys Leu Thr Pro Thr Val Val Val Leu Leu Cys Leu Thr
1               5                   10                  15
Phe Val Ala Asp Ala Leu Thr Ile Gln Glu Leu Arg Ala Gln Ile Ala
            20                  25                  30
Gln Gln Arg Ile Gln Gln Arg Tyr Gly Val Thr Val Ala Thr Thr Ser
        35                  40                  45
Ala

<210> SEQ ID NO 109
<211> LENGTH: 42
<212> TYPE: PRT
<213> ORGANISM: Artificial Sequence
<220> FEATURE:
<223> OTHER INFORMATION: Immunogenic polypeptide

<400> SEQUENCE: 109

Cys Ser Ser Leu Ser Asp Tyr Gly Leu Ile Glu Leu Lys Glu His Cys
1               5                   10                  15
Leu Glu Cys Cys Gln Lys Asp Thr Glu Ala Asp Ser Lys Leu Lys Val
            20                  25                  30
Tyr Pro Ala Ala Val Leu Glu Val Cys Thr
        35                  40

<210> SEQ ID NO 110
<211> LENGTH: 41
<212> TYPE: PRT
<213> ORGANISM: Artificial Sequence
<220> FEATURE:
<223> OTHER INFORMATION: Immunogenic polypeptide

<400> SEQUENCE: 110

Ala Ile Thr Tyr Ile Cys Phe Ile Leu His Gly Val Ser Glu Ile Ile

```
                1               5                  10                  15
         Pro Gln Gln Gln Lys Lys Thr Met Lys Phe Leu Leu Leu Val Ala Ser
                        20                  25                  30

Val Leu Cys Leu Val Leu Ile Val Ser
                        35                  40

<210> SEQ ID NO 111
<211> LENGTH: 24
<212> TYPE: PRT
<213> ORGANISM: Artificial Sequence
<220> FEATURE:
<223> OTHER INFORMATION: Immunogenic polypeptide

<400> SEQUENCE: 111

Glu Trp Arg Tyr Phe Val Val Ile Ala Leu Ile Cys Pro Leu Ile Ile
1               5                   10                  15

Val Glu Thr Leu Ala Val Ser Asp
            20

<210> SEQ ID NO 112
<211> LENGTH: 40
<212> TYPE: PRT
<213> ORGANISM: Artificial Sequence
<220> FEATURE:
<223> OTHER INFORMATION: Immunogenic polypeptide

<400> SEQUENCE: 112

Gln Leu Leu Leu Tyr Leu Asp Ala Ala Asp Leu Arg Arg Ala Leu
1               5                   10                  15

His Gln Tyr Gln Leu Leu Ala Ala Gln Gly Asp Arg His Leu Pro Gln
            20                  25                  30

Gln Ile Val Lys Phe Val Tyr Ala
            35                  40

<210> SEQ ID NO 113
<211> LENGTH: 41
<212> TYPE: PRT
<213> ORGANISM: Artificial Sequence
<220> FEATURE:
<223> OTHER INFORMATION: Immunogenic polypeptide

<400> SEQUENCE: 113

Arg Lys Val Leu Leu Thr Pro Ala Leu Gln Ala Tyr Ile Met Asp Glu
1               5                   10                  15

His Asn Leu Asn Arg Ser Asn Ile Ala Leu Gly Arg Ile Arg Pro Tyr
            20                  25                  30

Pro Ser Ala Val Lys Met Pro Thr Leu
            35                  40

<210> SEQ ID NO 114
<211> LENGTH: 31
<212> TYPE: PRT
<213> ORGANISM: Artificial Sequence
<220> FEATURE:
<223> OTHER INFORMATION: Immunogenic polypeptide

<400> SEQUENCE: 114

Asp Gly Val Leu Lys Gly Glu Thr His Lys Ala Leu Lys Leu Lys Asp
1               5                   10                  15

Gly Gly His Tyr Leu Val Glu Phe Lys Ser Ile Tyr Met Ala Lys
            20                  25                  30
```

```
<210> SEQ ID NO 115
<211> LENGTH: 44
<212> TYPE: PRT
<213> ORGANISM: Artificial Sequence
<220> FEATURE:
<223> OTHER INFORMATION: Immunogenic polypeptide

<400> SEQUENCE: 115

Ala Leu Val Leu His Ser Met Leu Val Asn Ala Ser Leu Ala Glu Met
1               5                   10                  15

Val Lys Glu Ser Tyr Gln Thr His Gly Ala Asp Gly Arg Met Val Val
            20                  25                  30

Arg Met Leu Lys Phe Val Arg Leu Leu Pro Gly Ala
        35                  40

<210> SEQ ID NO 116
<211> LENGTH: 36
<212> TYPE: PRT
<213> ORGANISM: Artificial Sequence
<220> FEATURE:
<223> OTHER INFORMATION: Immunogenic polypeptide

<400> SEQUENCE: 116

Val Gln Arg Val Arg Ala Leu Arg Ala Leu Leu Glu Thr Leu Leu Gln
1               5                   10                  15

His Gln Gly Glu Gln Asn Asn Asp Val Tyr Leu Ile Arg Leu Ala His
            20                  25                  30

Glu Thr Gly Arg
        35

<210> SEQ ID NO 117
<211> LENGTH: 41
<212> TYPE: PRT
<213> ORGANISM: Artificial Sequence
<220> FEATURE:
<223> OTHER INFORMATION: Immunogenic polypeptide

<400> SEQUENCE: 117

Val Asn Glu Leu Gln Gln Ala Leu Ser Ser Leu Asn Ala Gly Ser Gly
1               5                   10                  15

Ser Cys Ala Glu Val Phe Asn Ala Tyr Leu Pro Val His Asn Lys Tyr
            20                  25                  30

Ile Gly Val Ser Arg Lys Ile Tyr His
        35                  40

<210> SEQ ID NO 118
<211> LENGTH: 37
<212> TYPE: PRT
<213> ORGANISM: Artificial Sequence
<220> FEATURE:
<223> OTHER INFORMATION: Immunogenic polypeptide

<400> SEQUENCE: 118

Met Cys Lys Phe Tyr Arg Leu Ile Ser Thr Leu Leu Val Val Val
1               5                   10                  15

Ile Ala Pro Arg His Gln Cys Ser Pro Phe Phe Phe Gln Tyr Asn Arg
            20                  25                  30

Pro Tyr Leu Ser Gln
        35

<210> SEQ ID NO 119
<211> LENGTH: 40
<212> TYPE: PRT
```

```
<213> ORGANISM: Artificial Sequence
<220> FEATURE:
<223> OTHER INFORMATION: Immunogenic polypeptide

<400> SEQUENCE: 119

Arg Asp Asn Tyr Val Pro Asp Val Ser Ala Leu Glu Gln Asp Ile Ile
1               5                   10                  15

Glu Val Asp Pro Glu Thr Lys Glu Met Leu Lys His Leu Asp Phe Asn
                20                  25                  30

Asn Ile Val Val Gln Leu Thr Asn
            35                  40

<210> SEQ ID NO 120
<211> LENGTH: 32
<212> TYPE: PRT
<213> ORGANISM: Artificial Sequence
<220> FEATURE:
<223> OTHER INFORMATION: Immunogenic polypeptide

<400> SEQUENCE: 120

His Asp Gln Tyr Ser Met Glu Cys Leu Glu Ala Ala Glu Pro Lys Tyr
1               5                   10                  15

Leu Asp Gly Leu Lys Thr Leu Ala Asp Glu Thr Ala Gln Cys Met Arg
                20                  25                  30

<210> SEQ ID NO 121
<211> LENGTH: 36
<212> TYPE: PRT
<213> ORGANISM: Artificial Sequence
<220> FEATURE:
<223> OTHER INFORMATION: Immunogenic polypeptide

<400> SEQUENCE: 121

Glu Gln Glu Tyr Ala Gln Val Thr Lys Met Leu Gly Asn Gly Arg Leu
1               5                   10                  15

Glu Ala Met Cys Phe Asp Gly Val Lys Arg Leu Cys His Ile Arg Gly
                20                  25                  30

Lys Leu Arg Lys
        35

<210> SEQ ID NO 122
<211> LENGTH: 29
<212> TYPE: PRT
<213> ORGANISM: Artificial Sequence
<220> FEATURE:
<223> OTHER INFORMATION: Immunogenic polypeptide

<400> SEQUENCE: 122

Met Lys Leu Phe Leu Thr Leu Leu Ser Thr Leu Ser Val Ala Met Val
1               5                   10                  15

Phe Ala Leu Pro Ala His His His Ser Arg Gly Gly Asp
                20                  25

<210> SEQ ID NO 123
<211> LENGTH: 37
<212> TYPE: PRT
<213> ORGANISM: Artificial Sequence
<220> FEATURE:
<223> OTHER INFORMATION: Immunogenic polypeptide

<400> SEQUENCE: 123

Ser Asp Glu Leu Glu Glu Ala Arg Leu Val Ala Glu Glu Leu Glu Glu
1               5                   10                  15
```

```
Arg Gln Gln Glu Leu Asp Tyr Leu Lys Arg Tyr Leu Val Gly Arg Leu
            20                  25                  30

Gln Ala Val Ala Ile
        35

<210> SEQ ID NO 124
<211> LENGTH: 23
<212> TYPE: PRT
<213> ORGANISM: Artificial Sequence
<220> FEATURE:
<223> OTHER INFORMATION: Immunogenic polypeptide

<400> SEQUENCE: 124

Ile Ile Ser Tyr Phe Leu Thr Val Cys Leu Leu Ala Leu Val Gln Ser
1               5                   10                  15

Glu Thr Val Gln Asp Cys Glu
            20

<210> SEQ ID NO 125
<211> LENGTH: 35
<212> TYPE: PRT
<213> ORGANISM: Artificial Sequence
<220> FEATURE:
<223> OTHER INFORMATION: Immunogenic polypeptide

<400> SEQUENCE: 125

Asp Ser Ala Met Thr Asn Ala Asn Leu Val Gly Leu Thr Ile Ser Leu
1               5                   10                  15

Ala Tyr Ala Ile Phe Phe Leu Leu Tyr Thr Pro Pro Thr Gly Arg Ser
            20                  25                  30

Ser Tyr Trp
        35

<210> SEQ ID NO 126
<211> LENGTH: 40
<212> TYPE: PRT
<213> ORGANISM: Artificial Sequence
<220> FEATURE:
<223> OTHER INFORMATION: Immunogenic polypeptide

<400> SEQUENCE: 126

Val Val Ser Phe Ala Trp Leu Leu Tyr Gly Ile Ile Leu Arg Ser Asn
1               5                   10                  15

Phe Leu Val Val Gln Asn Leu Met Ala Leu Ala Leu Ser Ala Val Gln
            20                  25                  30

Leu Ser Leu Phe Ile Ile Phe Pro
        35                  40

<210> SEQ ID NO 127
<211> LENGTH: 40
<212> TYPE: PRT
<213> ORGANISM: Artificial Sequence
<220> FEATURE:
<223> OTHER INFORMATION: Immunogenic polypeptide

<400> SEQUENCE: 127

Thr Ser Ala Phe Pro Phe Ile Ser Gly Phe Leu Ser Cys Phe Met Trp
1               5                   10                  15

Leu Lys Tyr Gly Val Leu Thr Glu Glu Ser Thr Leu Ile Leu Val Asn
            20                  25                  30

Phe Ile Gly Ser Ala Leu Phe Phe
        35                  40
```

<210> SEQ ID NO 128
<211> LENGTH: 28
<212> TYPE: PRT
<213> ORGANISM: Artificial Sequence
<220> FEATURE:
<223> OTHER INFORMATION: Immunogenic polypeptide

<400> SEQUENCE: 128

Val Ile Gly Leu Leu Cys Cys Cys Leu Ala Val Leu Phe Phe Ala Ser
1               5                   10                  15

Pro Leu Thr Met Leu Ala His Val Ile Arg Thr Gln
            20                  25

<210> SEQ ID NO 129
<211> LENGTH: 30
<212> TYPE: PRT
<213> ORGANISM: Artificial Sequence
<220> FEATURE:
<223> OTHER INFORMATION: Immunogenic polypeptide

<400> SEQUENCE: 129

Val Glu Leu Leu Leu Ala Met Val Leu Leu Pro Leu Leu Leu Leu Glu
1               5                   10                  15

Ser Val Val Pro Tyr Ala Ala Ala Glu Lys Val Trp Val Asp
            20                  25                  30

<210> SEQ ID NO 130
<211> LENGTH: 4
<212> TYPE: PRT
<213> ORGANISM: Artificial Sequence
<220> FEATURE:
<223> OTHER INFORMATION: Placeholder
<220> FEATURE:
<221> NAME/KEY: MISC_FEATURE
<222> LOCATION: (1)..(4)
<223> OTHER INFORMATION: Xaa is any amino acid

<400> SEQUENCE: 130

Xaa Xaa Xaa Xaa
1

<210> SEQ ID NO 131
<211> LENGTH: 510
<212> TYPE: PRT
<213> ORGANISM: Artificial Sequence
<220> FEATURE:
<223> OTHER INFORMATION: Immunogenic polypeptide

<400> SEQUENCE: 131

Phe Leu Lys Gly Ser Phe Pro Arg Phe Gln Met Cys Val Met Leu Ile
1               5                   10                  15

Gly Phe Phe Ser Ser Ala Lys Cys Leu Phe Tyr Ser Val Gly Lys Leu
            20                  25                  30

Val Lys Val Leu Leu Val Met Ala Val Cys Cys Leu Leu Cys Thr
        35                  40                  45

Ala Pro Thr Gly Ala Asp Pro Leu Met Lys Phe Ala Phe Ala Phe Val
    50                  55                  60

Leu Ile Ala Leu Phe Ala Val Phe Ala Val Ser Gln Ala Leu Pro Gln
65                  70                  75                  80

Pro Glu Gln Ala Ala Ala Gly Arg Val Met Cys Leu Leu Arg Leu Met
                85                  90                  95

Ser Thr Leu Leu Val Val Leu Ser Ile Val Gly Lys Leu Tyr Ser Gly
            100                 105                 110

Tyr Arg Leu Leu Val Leu Val Met Thr Val Cys Cys Leu Leu Leu
            115                 120                 125

Phe Ile Ala Pro Thr Gly Ala Asp Pro Leu Pro Gly Gln Thr Gln Arg
    130                 135                 140

Thr Leu Ala Leu Ile Gly Leu Leu Leu Cys Ser Val Gln Ser Val Thr
145                 150                 155                 160

Ala Asn Asp Pro Val Asp Ala Leu Gly Ala Cys Ser Gly Asn Leu Phe
                165                 170                 175

Gly Leu Leu Met Thr Arg Leu Ser Lys Leu Phe Val Leu Ala Phe Leu
            180                 185                 190

Cys Leu Ala Leu Val Val Val Gln Ser Ala Pro Gln Tyr Ala Arg
            195                 200                 205

Gly Asp Val Pro Thr Leu Leu Pro Ala Lys Val Ile Pro Asp Lys Thr
    210                 215                 220

Ala Ala Tyr Val Ala Tyr Gly Gly Gln Glu Thr Leu Val Glu His Val
225                 230                 235                 240

Glu Val Leu Val Arg Tyr Phe Val Val Ile Ala Leu Ile Cys Pro Leu
                245                 250                 255

Ile Ile Val Glu Thr Leu Ala Val Val Leu Leu Thr Pro Ala Leu Gln
            260                 265                 270

Ala Tyr Ile Met Asp Glu His Asn Leu Asn Arg Ser Asn Ile Ala Leu
    275                 280                 285

Gly Arg Ile Arg Pro Tyr Pro Ser Ala Val Lys Met Pro Val Leu His
    290                 295                 300

Ser Met Leu Val Asn Ala Ser Leu Ala Glu Met Val Lys Glu Ser Tyr
305                 310                 315                 320

Gln Thr His Gly Ala Asp Gly Arg Met Val Val Arg Met Leu Lys Phe
                325                 330                 335

Val Arg Leu Leu Pro Arg Val Arg Ala Leu Arg Ala Leu Leu Glu Thr
            340                 345                 350

Leu Leu Gln His Gln Gly Glu Gln Asn Asn Asp Val Tyr Leu Ile Arg
    355                 360                 365

Leu Ala His Glu Thr Glu Leu Gln Gln Ala Leu Ser Ser Leu Asn Ala
    370                 375                 380

Gly Ser Gly Ser Cys Ala Glu Val Phe Asn Ala Tyr Leu Pro Val His
385                 390                 395                 400

Asn Lys Tyr Ile Gly Val Ser Arg Lys Ile Gln Tyr Ser Met Glu Cys
                405                 410                 415

Leu Glu Ala Ala Glu Pro Lys Tyr Leu Asp Gly Leu Lys Thr Leu Ala
            420                 425                 430

Asp Glu Thr Ala Gln Cys Ser Phe Ala Trp Leu Leu Tyr Gly Ile Ile
    435                 440                 445

Leu Arg Ser Asn Phe Leu Val Val Gln Asn Leu Met Ala Leu Ala Leu
    450                 455                 460

Ser Ala Val Gln Leu Ser Leu Phe Ile Ile Ala Phe Pro Phe Ile Ser
465                 470                 475                 480

Gly Phe Leu Ser Cys Phe Met Trp Leu Lys Tyr Gly Val Leu Thr Glu
                485                 490                 495

Glu Ser Thr Leu Ile Leu Val Asn Phe Ile Gly Ser Ala Leu
            500                 505                 510

<210> SEQ ID NO 132
<211> LENGTH: 864

```
<212> TYPE: PRT
<213> ORGANISM: Artificial Sequence
<220> FEATURE:
<223> OTHER INFORMATION: Immunogenic polypeptide

<400> SEQUENCE: 132

His Leu Thr Leu Phe Thr Val Ala Val Leu Leu Ala Ala Ala
1               5                   10                  15

Leu Leu Leu Leu Leu Pro Pro Ala Tyr Ser Thr Thr Leu Thr Pro Pro
            20                  25                  30

Pro Leu Ser Tyr Cys His Leu Phe Leu Thr His Thr Leu Ala Arg Ala
            35                  40                  45

Leu Ser Phe Ser Arg Ser Asp Cys Leu Lys Asn Val Phe Phe Ala Leu
    50                  55                  60

Leu Leu Val Val Leu Val Cys Cys Leu Val Ser Val Gln Gly Asn Glu
65                  70                  75                  80

Ile Lys Leu Leu Val Leu Leu Ile Cys Leu Phe Phe Tyr His Thr His
                    85                  90                  95

Cys Thr Thr Ala Tyr Leu Trp Leu Ala Met Gly Val Asn Asp Tyr Gln
                100                 105                 110

Ala Leu Leu Gly Leu Cys Cys Pro Trp Ile Asp Leu Ala Ala Ala Asp
                115                 120                 125

Leu Pro Met Arg Arg His Ala Lys Ala Asp Gly Ala Ser Ala Ile Thr
        130                 135                 140

Lys Ile Val Leu Glu Leu Thr Pro Glu Gln Ala Ala Val Thr Leu
145                 150                 155                 160

Phe Ile Phe Leu Val Cys Cys Gln Ile Pro Leu Phe Gly Ile Met Ser
                    165                 170                 175

Ser Asp Ser Ala Asp Pro Phe Tyr Trp Ile Arg Val Ile Leu Ala Met
                180                 185                 190

Tyr Cys Val Ile Lys Gly Lys Thr Gly Gly Tyr Cys Asn Ser Glu Gly
                195                 200                 205

Leu Cys Thr Cys Arg Ala Glu Asp Leu His Phe Leu Leu Lys Pro Ile
    210                 215                 220

Ile Asn Lys Asp Asn Ala Glu Asp Pro Arg Thr Glu Leu Ile Gly Cys
225                 230                 235                 240

Gly Ser Val Leu Phe His Leu Ala Ala Asn Arg Leu Ser Leu Gln Leu
                245                 250                 255

Glu Glu Phe Ala Val Cys Lys Arg Ser Met Leu Val Ala Phe Ala Thr
                260                 265                 270

Leu Ser Val Ala Leu Val Val Val Ala Ile Pro Ala Asn Phe Asn
    275                 280                 285

Tyr Gly Gly Gly Gly Tyr Phe Ile Asn Gly Thr Gly Gln Ile Tyr
    290                 295                 300

Glu Lys Leu Pro Ala Tyr Leu Ser Glu Val Ser Ala Arg Val Asn Val
305                 310                 315                 320

Leu Gln Val Ser Leu Gln His Asp Leu Pro Asn Leu Gln Glu Met Lys
                325                 330                 335

Leu Ala Lys Val Ala Leu Val Thr Ile Ser Leu Trp Phe Met Ala Trp
                340                 345                 350

Thr Pro Tyr Leu Val Ile Asn Phe Thr Gly Ile Phe Tyr Thr Cys Phe
                355                 360                 365

Leu Gly Thr Ser Ser Leu Ala Gly Phe Lys Asn Ala Val Asp Tyr Asp
        370                 375                 380
```

```
Glu Leu Leu Lys Ala Gly Val Leu Glu Val Leu Gly Phe Val Glu Asp
385                 390                 395                 400

Asn Gly Glu Leu Val Phe Gln Glu Leu Leu Gly Val Leu Lys Met Val
            405                 410                 415

Asp Pro Asp Gly Asp Lys Leu Thr Pro Thr Val Val Val Leu Leu
        420                 425                 430

Cys Leu Thr Phe Val Ala Asp Ala Leu Thr Ile Gln Glu Leu Arg Ala
        435                 440                 445

Gln Ile Ala Gln Gln Arg Ile Gln Gln Arg Tyr Gly Val Thr Val Ala
        450                 455                 460

Thr Thr Ser Leu Ser Asp Tyr Gly Leu Ile Glu Leu Lys Glu His Cys
465                 470                 475                 480

Leu Glu Cys Cys Gln Lys Asp Thr Glu Ala Asp Ser Lys Leu Lys Val
                485                 490                 495

Tyr Pro Ala Ala Val Leu Glu Val Thr Tyr Ile Cys Phe Ile Leu His
            500                 505                 510

Gly Val Ser Glu Ile Ile Pro Gln Gln Lys Lys Thr Met Lys Phe
            515                 520                 525

Leu Leu Leu Val Ala Ser Val Leu Cys Leu Val Leu Ile Leu Leu Leu
530                 535                 540

Tyr Leu Asp Ala Ala Asp Leu Arg Arg Ala Leu His Gln Tyr Gln Leu
545                 550                 555                 560

Leu Ala Ala Gln Gly Asp Arg His Leu Pro Gln Gln Ile Val Lys Phe
                565                 570                 575

Val Val Leu Lys Gly Glu Thr His Lys Ala Leu Lys Leu Lys Asp Gly
            580                 585                 590

Gly His Tyr Leu Val Glu Phe Lys Ser Ile Tyr Met Lys Phe Tyr Arg
        595                 600                 605

Leu Ile Ser Thr Leu Leu Val Val Val Ile Ala Pro Arg His Gln
610                 615                 620

Cys Ser Pro Phe Phe Gln Tyr Asn Arg Pro Tyr Leu Asn Tyr Val
625                 630                 635                 640

Pro Asp Val Ser Ala Leu Glu Gln Asp Ile Ile Glu Val Asp Pro Glu
            645                 650                 655

Thr Lys Glu Met Leu Lys His Leu Asp Phe Asn Asn Ile Val Val Gln
                660                 665                 670

Leu Glu Tyr Ala Gln Val Thr Lys Met Leu Gly Asn Gly Arg Leu Glu
            675                 680                 685

Ala Met Cys Phe Asp Gly Val Lys Arg Leu Cys His Ile Arg Gly Lys
        690                 695                 700

Leu Lys Leu Phe Leu Thr Leu Ser Thr Leu Ser Val Ala Met Val
705                 710                 715                 720

Phe Ala Leu Pro Ala His His His Ser Arg Gly Glu Leu Glu Glu Ala
                725                 730                 735

Arg Leu Val Ala Glu Glu Leu Glu Glu Arg Gln Gln Glu Leu Asp Tyr
            740                 745                 750

Leu Lys Arg Tyr Leu Val Gly Arg Leu Gln Ala Val Ser Tyr Phe Leu
        755                 760                 765

Thr Val Cys Leu Leu Ala Leu Val Gln Ser Glu Thr Val Gln Asp Ala
            770                 775                 780

Met Thr Asn Ala Asn Leu Val Gly Leu Thr Ile Ser Leu Ala Tyr Ala
785                 790                 795                 800

Ile Phe Phe Leu Leu Tyr Thr Pro Pro Thr Gly Arg Ser Ser Gly Leu
```

```
                    805                 810                 815
Leu Cys Cys Cys Leu Ala Val Leu Phe Phe Ala Ser Pro Leu Thr Met
                820                 825                 830

Leu Ala His Val Ile Arg Leu Leu Leu Ala Met Val Leu Leu Pro Leu
                835                 840                 845

Leu Leu Leu Glu Ser Val Val Pro Tyr Ala Ala Glu Lys Val Trp
    850                 855                 860
```

```
<210> SEQ ID NO 133
<211> LENGTH: 162
<212> TYPE: PRT
<213> ORGANISM: Artificial Sequence
<220> FEATURE:
<223> OTHER INFORMATION: Immunogenic polypeptide

<400> SEQUENCE: 133

His Leu Thr Leu Phe Thr Val Ala Val Leu Leu Ala Ala Ala Ala
1               5                   10                  15

Leu Leu Leu Leu Leu Pro Pro Ala Tyr Ser Thr Thr Leu Thr Pro Pro
                20                  25                  30

Pro Leu Ser Tyr Cys His Leu Phe Leu Thr His Thr Leu Ala Arg Ala
            35                  40                  45

Leu Ser Phe Ser Arg Ser Asp Cys Leu Lys Asn Val Phe Phe Ala Leu
    50                  55                  60

Leu Leu Val Val Leu Val Cys Cys Leu Val Ser Val Gln Gly Asn Glu
65                  70                  75                  80

Ile Lys Leu Leu Val Leu Leu Ile Cys Leu Phe Phe Tyr His Thr His
                85                  90                  95

Cys Thr Thr Ala Tyr Leu Trp Leu Ala Met Gly Val Phe Leu Lys Gly
            100                 105                 110

Ser Phe Pro Arg Phe Gln Met Cys Val Met Leu Ile Gly Phe Phe Ser
        115                 120                 125

Ser Ala Lys Cys Leu Asn Asp Tyr Gln Ala Leu Leu Gly Leu Cys Cys
    130                 135                 140

Pro Trp Ile Asp Leu Ala Ala Ala Asp Leu Pro Met Arg Arg His Ala
145                 150                 155                 160

Lys Ala
```

```
<210> SEQ ID NO 134
<211> LENGTH: 205
<212> TYPE: PRT
<213> ORGANISM: Artificial Sequence
<220> FEATURE:
<223> OTHER INFORMATION: Immunogenic polypeptide

<400> SEQUENCE: 134

Leu Leu Pro Ala Lys Val Ile Pro Asp Lys Thr Ala Ala Tyr Val Ala
1               5                   10                  15

Tyr Gly Gly Gln Glu Thr Leu Val Glu His Val Glu Val Leu Val Val
                20                  25                  30

Leu Leu Thr Pro Ala Leu Gln Ala Tyr Ile Met Asp Glu His Asn Leu
            35                  40                  45

Asn Arg Ser Asn Ile Ala Leu Gly Arg Ile Arg Pro Tyr Pro Ser Ala
    50                  55                  60

Val Lys Met Pro Val Leu His Ser Met Leu Val Asn Ala Ser Leu Ala
65                  70                  75                  80

Glu Met Val Lys Glu Ser Tyr Gln Thr His Gly Ala Asp Gly Arg Met
```

-continued

```
                85                  90                  95
Val Val Arg Met Leu Lys Phe Val Arg Leu Leu Pro Arg Val Arg Ala
            100                 105                 110

Leu Arg Ala Leu Leu Glu Thr Leu Leu Gln His Gln Gly Glu Gln Asn
        115                 120                 125

Asn Asp Val Tyr Leu Ile Arg Leu Ala His Glu Thr Glu Leu Gln Gln
    130                 135                 140

Ala Leu Ser Ser Leu Asn Ala Gly Ser Gly Ser Cys Ala Glu Val Phe
145                 150                 155                 160

Asn Ala Tyr Leu Pro Val His Asn Lys Tyr Ile Gly Val Ser Arg Lys
                165                 170                 175

Ile Gln Tyr Ser Met Glu Cys Leu Glu Ala Ala Glu Pro Lys Tyr Leu
            180                 185                 190

Asp Gly Leu Lys Thr Leu Ala Asp Glu Thr Ala Gln Cys
        195                 200                 205
```

PEPTIDE SEQUENCES AND COMPOSITIONS

The invention concerns peptide sequences, compositions comprising the peptide sequences, in particular vaccines against arthropod borne diseases comprising the sequences and the compositions, and uses of the sequences. The present invention is particularly concerned with vaccines that are protective against any one or more mosquito borne diseases, including one or more strains of malaria.

The defence against disease is critical for the survival of all animals, and the defence mechanism employed for this purpose is the animal immune system. Understanding the immune system is therefore a key to understanding the development of new and more sophisticated treatments for humans and animals alike.

The mechanism of operation of the immune system has been under investigation for many years. The system is composed of a number of cell types and a variety of molecules, making it extremely complex. Even after many years of study, the full extent of the immune system components, and their interaction with each other, is imperfectly understood.

Many years ago it was recognised that a person who recovers from a particular disease may acquire some protection in future against that disease, but not against a disease which that person has not yet contracted. This fundamental aspect of the immune system was interpreted at that time by considering that the immune system acquired a kind of 'memory' against certain pathogens once exposure to such pathogens had taken place, that memory being specific to a certain disease.

Gradually, it became known that exposure to less harmful variants of a pathogen could induce protection against more harmful variants (e.g. exposure to cowpox to protect against smallpox, or exposure to an inactivated anthrax to protect against live anthrax). Thus, the idea of vaccination against a disease arose.

It is now known that the immune system has at least two divisions: innate immunity and adaptive immunity. The innate system is fully functional before a pathogen enters the system, whilst the adaptive system is switched on after the pathogen enters the system. It then develops an attack specific to the pathogen. The innate system comprises a number of components, including phagocytes such as macrophages, which (as the name suggests) 'eat' or engulf foreign bodies such as pathogens.

Typically, but not exclusively, the present invention is concerned with the adaptive immune system, and unless specifically indicated otherwise, 'immune system' in the present context refers to the adaptive immune system.

In order to understand more fully how the immune system functions, the role of its individual components must be carefully considered. In respect of the adaptive immune system, it is well known that immunity against pathogens is provided by the action of lymphocytes, which constitute the most common cell type in the immune system. There are two types of lymphocyte: the B lymphocyte and the T lymphocyte. These are generally termed B cells and T cells respectively.

B cells have the ability to develop into plasma cells, which manufacture antibodies. Antibodies are very important components of the animal immune system. They are produced in response to some signature portion of the invading pathogen (an antigen of the pathogen—antigens here being defined as any foreign substance recognised by the immune system) and are usually specific to that pathogen. However, if two pathogens are very similar, or at least contain the same antigen, then antibodies produced against one can nevertheless be effective against the other (they may 'cross-react'). This explains why inoculation with cowpox may protect against smallpox. It is important to realise that the antibodies 'recognise' only a small portion of the antigenic molecule of the pathogen rather than the pathogen as a whole. These portions are termed epitopes.

T cells do not possess or produce antibodies. Instead, they recognise fragments (i.e. epitopes) of the foreign antigen complexed with major histocompatibility complex (MHC) (or in the case of humans, human leucocyte antigen (HLA)) via a specialised receptor known as TCR (T cell receptor). T cells are themselves divisible into subsets which can have either a regulatory function or an effector function. The effector cells are involved with 'effecting' the removal of foreign substances. For example, cytotoxic T cells (CTL) are effector cells that are able to kill infected cells, as well as other unwanted species such as tumour cells. Regulatory T cells, on the other hand, play a role in helping effector T and B cells to become more effective. Due to this function, these regulatory T cells are often termed 'helper' T cells. Other regulatory T cells, termed 'suppressor' T cells, are thought to inhibit immune responses, but these are less well understood. Regulatory T cells may also interact with components of the innate immune system to boost their activity.

In a normal healthy individual, the lymphocytes in the immune system remain in an inactive 'resting' state until an immune response is triggered. When an immune response is required, the lymphocytes become activated, proliferate and begin to carry out their designated functions. For example, any resting T cell displaying on its surface a TCR that recognises an epitope of the invading pathogen complexed with a MHC molecule is activated, proliferates (this being termed clonal expansion) and the resulting offspring start to actively carry out their predetermined effector functions required to combat the invading organisms.

When the immune response is completed, (i.e. the pathogens and/or infected cells have been eliminated) the lymphocytes revert to a resting state once again. This resting state is not, however, equivalent to the initial inactive resting state. Activated, but resting lymphocytes, can be rapidly recruited and induced to proliferate in response to an infection by the same, or closely related, pathogen at a later time.

This ability of activated resting lymphocytes, to deliver a faster and more powerful response following a second encounter with an invading pathogen, effectively provides the immune system with 'memory'. The exploitation of the immune system's memory is the basis for all long-term immunoprophylactic drugs (e.g. vaccines) and remains the goal of much long-term immunotherapeutic drug development.

In order for cells to perform their functions within the complex systems of an animal, the cells need to have 'receptors' on their surfaces. These receptors are capable of 'recognising' specific substances that control various essential processes such as activation, proliferation and adherence to other cells or substrates. For example, in the case of the immune system, the receptors on T and B cells allow them not only to recognise antigen but also to interact with each other and thus regulate their activities. Without these receptors, the cells would lack an essential means of communication and would be unable to act effectively in the concerted way that is essential for the immune system of a multicellular organism.

In order to be able to specifically recognise and deal with the wide range of pathogens present in the environment, the immune system has developed two types of highly variable antigen receptor on lymphocytes: antibodies in B cells and T cell receptors, or TCRs, in T cells.

There are a great many different possible antigen receptors present in the body, to enable the immune system to recognise a wide variety of invading pathogens. In fact there are approximately 10^12 different B cells and T cell receptors in an individual. Each individual B cell has only one type of receptor, and so to deal with a particular pathogen, a B cell having the 'best fitting' receptor for an antigen of that pathogen must be selected. This process is termed 'clonal selection'. In theory, only a single clone may respond (a monoclonal response) or several (an oligoclonal response) or many (a polyclonal response) depending on the number of antigens/epitopes exhibited by the pathogen, and the specificity of the various selected B cells to these antigen/epitopes.

There is a major difference between the types of antigen that can be recognised by B cells and T cells. As far as it is known, only the receptors on the surface of B lymphocytes (i.e. antibodies) are capable of directly recognising antigens such as proteins on viruses and bacteria, or foreign molecules dissolved in body fluid. Antibodies can also be produced in a soluble form by the B cells when they are activated and develop into plasma cells. The antibodies are also termed immunoglobulins (abbreviated to Ig). T cell receptors, on the other hand, recognise only short peptides, also known as T cell epitopes, on the surface of cells of the body. These T-cell epitopes are produced by degradation of larger proteins that are either self (i.e. naturally occurring body proteins) or non-self (i.e. derived from foreign organisms infecting the body). Only those derived from foreign proteins, i.e. antigens, are normally capable of inducing an immune response in the body. Once produced, these epitopes are bound to a special type of molecule, the MHC (major histocompatibility complex) and the resulting complex is then presented on the cell surface for binding the T cell receptor.

It should be clear that due to the destructive nature of the immune response, the response has to act only against foreign pathogens, not against the body's own cells or proteins. Thus, the immune system needs to distinguish between 'self' and 'non-self'. It has been proposed that although clones of lymphocytes reacting against self are produced, they are deleted before any reaction can occur. This process is termed 'clonal deletion'. It has also been proposed that any self-reacting lymphocytes could be retained but only in a 'switched-off' state. This mechanism is termed 'clonal anergy'. Whatever the process considered, it remains unclear what is the exact underlying mechanism allowing lymphoid tissues, such as the thymus, to identify individual T cell clones reacting against self from the pool of T lymphocytes reacting only against non-self.

It has been known for many years that the major histocompatibility complex (MHC) plays a key role in the immune system of animals. The MHC molecules enable T cells to recognise antigens, as has already been discussed above. There are three general types of MHC molecule, class I, class II and class III. Class I and class II MHC molecules are glycoproteins that are present on the surface of the cell, whilst class III are usually soluble molecules present inside the cell. There are a large number of different types of MHC molecule. For example in humans (where MHC is termed HLA, human leukocyte antigen) there are several hundreds of different alleles of the genes coding for MHC molecules, meaning that in the human population there are many different types of HLA. The MHC of different species is typically named according to different conventions, thus MHC for mouse is termed H-2, for rat RT1 and for rabbit RLA. The different gene regions coding for different MHC molecules in an individual are usually individually named, such as HLA-A, HLA-C etc. in humans.

The MHC molecule is a critical immune system molecule, since it is this molecule that presents the epitopes of the antigens to the immune system. For example, if a T cell is to respond to a particular pathogen, the pathogen must have a least one antigen (such as a protein) that has at least one epitope (such as a peptide portion of the protein) that can bind to an MHC molecule on the surface of a cell and thus interact with a T cell which binds to the MHC-peptide complex. Thus, the immune response is dependent on the ability of the MHC to bind to an epitope. If there is no epitope that the MHC will bind to, or if there is no T cell which will bind to the MHC-peptide complex, then no immune response will occur.

In respect of 'self' proteins, however, one of several epitopes may be able to bind to the MHC molecule and hence potentially induce an immune response. On these occasions a specific "signal" must be provided for the self-reacting lymphocyte clones to be deleted or "switched off".

Despite the growing knowledge of the workings of the vertebrate immune system, vaccines against many diseases remain elusive. Certain pathogens are subject to rapid mutation (e.g. HIV and influenza), such that epitopes that may be useful vaccine targets for one strain, are not useful after mutation has occurred because the epitope has changed in the new strain. Other pathogens such as *plasmodium* (the pathogen responsible for malaria) have been extensively investigated, but targets on the pathogen that can be useful in vaccine development have proven difficult to identify, or have simply failed to deliver an effective vaccine in vivo.

Pathogens for which there is a particular need for progress are those that are borne by arthropods and cause so-called "arthropod borne diseases". Such diseases are a major cause of death worldwide, and include inter alia malaria and dengue some of the greatest killers in the population today, particularly in poorer regions of the world. Examples include, but are not limited to, those listed in Table 1 below.

TABLE 1

Arthropod-borne diseases, with their pathogens and vectors

| Disease | Pathogen (parasite/virus) | Arthropod Vector |
|---|---|---|
| Malaria | *Plasmodium* sp. | *Anopheles* sp. |
| Filariasis | *Wuchereria* sp. | *Anopheles* sp. |
|  | *Brugia* sp. | *Aedes* sp. |
|  | *Loa* sp. | *Culex* sp. |
|  | *Mansonella* sp. | *Mansonia* sp. |
|  |  | *Chrysops* sp. |
| River blindness | *Onchocerca* sp. | *Simulium* sp. |
| Chagas Disease | *Trypanosoma* sp. | *Triatoma* sp. |
| Sleeping Sickness |  | *Rhodnius* sp. |
|  |  | *Panstrongylus* sp. |
|  |  | *Glossina* sp. |
|  |  | *Tabanus* sp. |
| Leishmaniasis | *Leishmania* sp. | *Phlebotomus* sp. |
|  |  | *Lutzomyia* sp. |
| Tularaemia | *Franciscella tulariensis* | *Tabanus* sp. |
| Relapsing fever | *Borrelia* sp. | *Pediculus* sp |
| Lyme disease |  | *Ornithodoros* sp. |
|  |  | *Ixodes* sp. |
| Typhus | *Rickettsia* sp. | *Pediculus* sp. |
|  |  | *Pulex* sp. |
| Plague | *Yersinia* sp. | *Pulex* sp. |
| Dengue fever | DEN-1 to -4 flavivirus | *Aedes* sp. |
| Yellow fever | Yellow fever flavivirus | *Aedes* sp. |
|  |  | *Hemagogous spegazzani.* |
| Rift valley fever | Rift valley virus | *Aedes* sp. |
| Encephalitis | Flavi-, Alpha- and | *Culex* sp. |
| Including | Bunyaviruses | *Ochlerotatus* sp. |
| St. Louis Encephalitis |  | *Aedes* sp. |
| West Nile fever |  | *Coquillettidia* sp. |
| Eastern Equine Encephalitis |  | *Anopheles* sp. |
| La Crosse Encephalitis |  |  |
| Eastern Equine Encephalitis |  |  |

Previously, attempts to provide arthropod borne disease vaccines have involved identifying existing pathogen strains and then producing a vaccine specific to that pathogen. Generally, the vaccines have been based upon a B cell (antibody) response (or occasionally a T cell response) the antibody being reactive with the surface antigens of the specific pathogen strain against which it has been developed. Typically, the surface proteins comprising the antigens are variable from one disease strain to the next, and completely different for different pathogens. The consequence of this is that conventional vaccines generally protect only against one specific pathogen or pathogen strain (if they are effective at all) and will not protect against other strains or a new strain that results from a mutation. Thus, a separate vaccine is required for protection against each disease and often against different and/or new strains of the same disease.

It has been known for some time that immunisation against arthropod saliva, or against antigens expressed in the gut of arthropods can protect an individual from infection. Articles discussing this include those summarised below.

R. G. Titus et al. "The immunomodulatory factors of arthropod saliva and the potential for these factors to serve as vaccine targets to prevent pathogen transmission.", *Parasite Immunology*, 2006, 28, 131-141. The article reviews known immunomodulators in arthropod salivary glands Immunomodulatory factors can enhance pathogen transmission by arthropods. Vector saliva contains a large number of substances whose activities include the ability to inhibit haemostasis, vasoconstriction and the development of inflammation and an immune response. In mosquitoes there are several T-cell inhibitors. If arthropod saliva enhances infection with the pathogens arthropods transmit it should be possible to control pathogen transmission by vaccinating the host against the molecule(s) in saliva that potentiate the infection, thereby blocking the enhancing effects of saliva and thus preventing the pathogen from establishing infection in the host. The gene maxadilan or MAX that encodes the potent vasodilator in sandfly saliva was cloned and the activities of the protein product of the gene were examined. The effects of sandfly MAX manifest through primary effects on phagocytic cells and this leads to downstream immunomodulatory/inhibitory effects on T-cell responses. Mice were vaccinated against MAX by injecting MAX in complete Freund's adjuvant followed by MAX in incomplete Freund's adjuvant and then boosted with soluble MAX until circulating anti-MAX antibody titre of between 1/10000 and 1/20000. The vaccinated mice were markedly protected from infection.

G. A. T. Targett, "Parasites, arthropod vectors, and immune responses.", *Parasite Immunology*, 2006, 28, 117-119. This article shows that blood feeding by mosquitoes induces immune responses to insect's saliva. These include both hypersensitivity reactions and anti-mosquito antibodies. Measurement of these antibody responses can be of value epidemiologically for monitoring vector populations and the application of such responses to assessment of the effectiveness of intervention strategies. The production of vaccines that would impair the feeding, development and/or survival of arthropod vectors or ectoparasites is an attractive if ambitious idea. One important objective is control of the ectoparasitic arthropods themselves, while a second is to use the anti-arthropod vaccine as a way to harm the parasites that the arthropod transmits either within the arthropod itself or when transmission to the vertebrate host occurs.

M. M. A. Whitten et al., "Mosquito midguts and malaria: cell biology, compartmentalization and immunology.", *Parasite Immunology*, 2006, 28, 121-130. The mosquito midgut represents one of the most challenging environments for the survival and development of *Plasmodium*. During their attempts to cross the midgut epithelium en route to the salivary glands, motile ookinetes are swiftly detected and labelled by mosquito recognition factors and targeted for destruction by a variety of immune responses that recruit killing factors both from the midgut and from other tissues in the surrounding body cavity. The exact interplay between these factors and the parasite is highly species and strain specific as are the timing and the route of the parasite invasion. The midgut forms a physical barrier separating and protecting the haemocoel tissues from digestive enzymes and infectious agents. It is composed of a single layer of polarised epithelial cells, with either pole displaying different morphological adaptations for increasing the surface area involved in the exchange of molecules. The distinct microvillous apical surface is exposed to the lumen, and its primary role is the secretion of digestive enzymes and absorption of nutrients. Structural modifications triggered by blood feeding include the formation of a thick non-cellular, chitinous peritrophic matrix (PM) that is secreted by the midgut epithelium and that is polymerized by the ingested blood meal. The PM surrounds the blood bolus and forms a barrier for parasites and bacteria attempting to penetrate the midgut epithelium.

P. F. Billingsley et al. "Immune interactions between mosquitoes and their hosts.", *Parasite Immunology*, 2006, 28, 143-153. Antibodies targeting the mosquito midgut are also important in the development of mosquito vaccines. The secretion of saliva by a mosquito during feeding is important for the successful location of host blood vessels and manipulation of host haemostatic and immune responses Immunoblotting techniques have been used to characterise the recognition by host anti-mosquito antibodies of salivary antigens. When a mosquito feeds, it ingests host immune factors, both soluble and cellular, that remain active in the midgut. In contrast to salivary antigens, the host will not normally have been exposed to antigens from the internal organs of the mosquito, which leads to the idea of these 'concealed' antigens as vaccine targets. The best source of concealed antigens is the midgut, because after feeding it contains the blood meal with its component immune effector molecules and cells. Midguts and whole body preparations of *Ae. Aegypti* induced high antibody titres in mice and the increased mortality of mosquitoes that fed on them was correlated with antibody that bound to midgut microvilli. IgG responses were induced in mice injected with a midgut cDNA library of *An. Gambiae*, and high antibody titres achieved after boosting with midgut proteins. Mosquitoes feeding on these mice showed reproducible reductions in survival and fecundity, but interestingly cellular rather than humoral responses seemed to be responsible for the mosquitocidal effects. These studies have encountered problems. Even within experiments, variability can be high and reproducibility of effect difficult to achieve. Immunization with a complex mixture of either midgut protein extracts or a midgut cDNA library has meant that protective target antigens have not been identified.

However, despite this knowledge, no effective vaccine against arthropod borne diseases has yet been developed that makes use of this mechanism of action. A further significant problem with existing vaccines against arthropod borne pathogens, whether relying on a B-cell or T-cell response, is that each protects only against a single pathogen, or at most a single existing pathogen strain, and does not provide protection against possible future strains or against multiple pathogens. There is a desperate need for a vaccine to protect against a plurality of arthropod borne diseases, including large scale killers such as Malaria and Dengue.

The inventors have been now able to identify specific immunogenic peptide sequences present in arthropod saliva proteins that may provide protection against all arthropod borne pathogens, and have developed vaccines to the diseases they cause, using the identified sequences. Thus, the inventors have developed peptides useful in vaccines eliciting an immune response, and in particular a rapid secondary immune response against arthropod borne diseases.

Accordingly, it is an aim of the present invention to solve the problems associated with the known prior art as set out above. It is a further aim of the present invention to provide a polypeptide composition that is capable of eliciting a immune response (e.g. a cellular response including a T-cell response and/or a B cell response) in vertebrates against a plurality of arthropod borne diseases, i.e. diseases caused by a plurality of pathogens or pathogen strains. It is a further aim of the present invention to provide an arthropod borne disease vaccine using the polypeptide compositions of the invention.

Accordingly, the present invention provides a polypeptide composition comprising one or more polypeptides, which polypeptides are immunogenic in a vertebrate, such that they cause the vertebrate to produce immune system cells (or promote the production of such cells) capable of recognising at least one epitope from an arthropod saliva protein fraction, wherein the arthropod saliva protein fraction has a mass of 40 kDA or less, and wherein the polypeptides are selected independently from:

(a) the polypeptide sequences of SEQ ID 1-44 or sub-sequences from these sequences, the sub-sequences having 7 amino acids or more:

```
SEQ ID 1   HLTLFTVAVLLLAAAALLLLLPPAYSTTLTPP
SEQ ID 2   PLSYCHLFLTHTLARALSFSRSDCL
SEQ ID 3   KNVFFALLLVVLVCCLVSVQGNEI
SEQ ID 4   KLLVLLICLFFYHTHCTTAYLWLAMGV
SEQ ID 5   FLKGSFPRFQMCVMLIGFFSSAKCL
SEQ ID 6   NDYQALLGLCCPWIDLAAADLPMRRHAKA
SEQ ID 7   FYSVGKLVKVLLVMAVCCLLLCTAPTGADPL
SEQ ID 8   MKFAFAFVLIALFAVFAVSQALPQPEQAAA
SEQ ID 9   DGASAITKIVLELTPEQAAAV
SEQ ID 10  TLFIFLVCCQIPLFGIMSSDSADPFYWIRVILA
SEQ ID 11  GRVMCLLRLMSTLLVVLSIVGK
SEQ ID 12  LYSGYRLLVLLVMTVCCLLLFIAPTGADPLPGQTQRTL
SEQ ID 13  MYCVIKGKTGGYCNSEGLCTCRAEDLHFLLKPIINKD
SEQ ID 14  NAEDPRTELIGCGSVLFHLAANRLSLQLEEFAVCKR
SEQ ID 15  ALIGLLLCSVQSVTANDPVDALGACSGNLFGLLMTRL
SEQ ID 16  SKLFVLAFLCLALVVVVQSAPQYARGDVPT
SEQ ID 17  SMLVAFATLSVALVVVVAIPANFNYGGGGGYFINGTGQ
SEQ ID 18  IYEKLPAYLSEVSARVNVLQVSLQHDLPNLQ
SEQ ID 19  EMKLAKVALVTISLWFMAWTPYLVINFTGI
SEQ ID 20  LLPAKVIPDKTAAYVAYGGQETLVEHVEVLV
SEQ ID 21  FYTCFLGTSSLAGFKNAVDYDELLKAG
SEQ ID 22  VLEVLGFVEDNGELVFQELLGVLKMVDPDGD
SEQ ID 23  KLTPTVVVVLLCLTFVADALTIQELRAQIAQQRIQQRYGV
           TVATT
SEQ ID 24  SLSDYGLIELKEHCLECCQKDTEADSKLKVYPAAVLEV
SEQ ID 25  TYICFILHGVSEIIPQQQKKTMKFLLLVASVLCLVLI
SEQ ID 26  RYFVVIALICPLIIVETLAV
SEQ ID 27  LLLYLDAADLRRALHQYQLLAAQGDRHLPQQIVKFV
SEQ ID 28  VLLTPALQAYIMDEHNLNRSNIALGRIRPYPSAVKMP
SEQ ID 29  VLKGETHKALKLKDGGHYLVEFKSIYM
SEQ ID 30  VLHSMLVNASLAEMVKESYQTHGADGRMVVRMLKFVRLLP
SEQ ID 31  RVRALRALLETLLQHQGEQNNDVYLIRLAHET
SEQ ID 32  ELQQALSSLNAGSGSCAEVFNAYLPVHNKYIGVSRKI
SEQ ID 33  KFYRLISTLLVVVVIAPRHQCSPFFFQYNRPYL
SEQ ID 34  NYVPDVSALEQDIIEVDPETKEMLKHLDFNNIVVQL
SEQ ID 35  QYSMECLEAAEPKYLDGLKTLADETAQC
SEQ ID 36  EYAQVTKMLGNGRLEAMCFDGVKRLCHIRGKL
SEQ ID 37  KLFLTLLSTLSVAMVFALPAHHHSRG
SEQ ID 38  ELEEARLVAEELEERQQELDYLKRYLVGRLQAV
SEQ ID 39  SYFLTVCLLALVQSETVQD
SEQ ID 40  AMTNANLVGLTISLAYAIFFLLYTPPTGRSS
SEQ ID 41  SFAWLLYGIILRSNFLVVQNLMALALSAVQLSLFII
SEQ ID 42  AFPFISGFLSCFMWLKYGVLTEESTLILVNFIGSAL
SEQ ID 43  GLLCCCLAVLFFASPLTMLAHVIR
SEQ ID 44  LLLAMVLLPLLLLESVVPYAAAEKVW
```

(b) the sequences defined by the following amino acid residues of an arthropod saliva protein, or sub-sequences from these sequences, the sub-sequences having 7 amino acids or more:

residues 2-33 of >gi|18389913|gbl AAL68793.1|AF457563_1 hypothetical protein 16 [*Anopheles gambiae*]

residues 2-26 of >gi|18389909|gbl AAL68791.1|AF457561_1 hypothetical protein 14 [*Anopheles gambiae*]

residues 2-25 of >gi|18389907|gbIAA L68790.1|AF457560_1 hypothetical protein 13 [*Anopheles gambiae*]

residues 10-36 of >gi|18389903|gbIAAL68788. 1|AF457558_1 hypothetical protein 11 [*Anopheles gambiae*]

residues 2-26 of >gi|62546227|gbIAAX86005.1|hyp3.5 precursor [*Anopheles gambiae*]

residues 14-42 of gi|18389899|gbIAAL68786.1|AF457556_1 salivary gland 7-like protein [*Anopheles gambiae*]

residues 3-33 of >gi|18389911|gbl AAL68792.1|AF457562_1 hypothetical protein 15 [*Anopheles gambiae*]

residues 1-30 of >gi|62546225|gbIAAX86004.1|hyp6.3 precursor [*Anopheles gambiae*]

residues 34-54 of >gi|62546225|gbIAAX86004.1|hyp6.3 precursor [*Anopheles gambiae*]

residues 38-70 of >gi|17026153|embICAD12038.1|Sec61 protein [*Anopheles gambiae*]

residues 2-23 of >gi|62546223|gbIAAX86003.1|hyp6.2 precursor [*Anopheles gambiae*]

residues 17-54 of >gi|18389915|gb|AAL68794.1|AF457564_1 hypothetical protein 17 [*Anopheles gambiae*]

residues 57-93 of >gi|87080391|gb|ABD18596.1| defensin [*Anopheles gambiae*]

residues 22-57 of >gi|18389901|gb|AAL68787.1|AF457557_1 hypothetical protein 10 [*Anopheles gambiae*]

residues 7-43 of >gi|18389905|gb|AAL68789.1|AF457559_1 hypothetical protein 12 [*Anopheles gambiae*]

residues 3-32 of >gi|4127344|emb|CAA76832.1| cE5 protein [*Anopheles gambiae*]

residues 3-40 of >gi|4210617|emb|CAA10259.1| SG2 protein [*Anopheles gambiae*]

residues 91-121 of >gi|4127309|emb|CAA76820.1| hypothetical protein [*Anopheles gambiae*]

residues 65-94 of >gi|4375824|emb|CAA76825.1| opsin [*Anopheles gambiae*]

residues 41-71 of >gi|62546233|gb|AAX86008.1| unknown [*Anopheles gambiae*]

residues 117-143 of >gi|3378531|emb|CAA03872.1| D7r2 protein [*Anopheles gambiae*]

residues 63-93 of >gi|3378529|emb|CAA03871.1| D7r3 protein [*Anopheles gambiae*]

residues 23-67 of >gi|18389893|gb|AAL68783.1|AF457553_1 mucin-like protein [*Anopheles gambiae*]

residues 43-80 of >gi|18389881|gb|AAL68777.1|AF457547_1 selenoprotein [*Anopheles gambiae*]

residues 6-42 of >gi|18389879|gb|AAL68776.1|AF457546_1 30 kDa protein [*Anopheles gambiae*]

residues 4-23 of >gi|18378603|gb|AAL68639.1|AF458073_1 D7-related 5 protein [*Anopheles gambiae*]

residues 20-55 of >gi|18389897|gb|AAL68785.1|AF457555_1 salivary gland 1-like 4 protein [*Anopheles gambiae*]

residues 59-95 of >gi|18389883|gb|AAL68778.1|AF457548_1 antigen 5-related 1 protein [*Anopheles gambiae*]

residues 158-184 of >gi|83016748|dbj|BAE53441.1|DsRed [synthetic construct]

residues 37-76 of >gi|18389895|gb|AAL68784.1|AF457554_1 salivary gland 1-like 3 protein [*Anopheles gambiae*]

residues 191-222 of >gi|8389895|gb|AAL68784.1|AF457554_1 salivary gland 1-like 3 protein [*Anopheles gambiae*]

residues 113-149 of >gi|18389891|gb|AAL68782.1|AF457552_1 D7 protein long form [*Anopheles gambiae*]

residues 1-37 of >emb|CAC35527.1| gSG9 protein [*Anopheles gambiae*]

residues 81-120 of >sp|Q9U9L1|RS17_ANOGA 40S ribosomal protein S17 residues 111 to 142 of >emb|CAC35523.1| gSG7 protein [*Anopheles gambiae*]

residues 32-67 of >gb|AAD47075.1|AF164151_1 translation initiation factor 4C (1A) [*Anopheles gambiae*]

residues 1-29 of >emb|CAC35519.1| gSG2-like protein [*Anopheles gambiae*]

residues 106-142 of >emb|CAC35451.1| hypothetical protein [*Anopheles gambiae*]

residues 6-28 of >emb|CAC35524.1| D7r4 protein [*Anopheles gambiae*]

residues 70-104 of >ref|XP_001230998.1| ENSANGP00000014906 [*Anopheles gambiae* str. PEST]

residues 174-213 of >ref|XP_316361.2| ENSANGP00000012984 [*Anopheles gambiae* str. PEST]

residues 41-80 of >ref|XP_314140.3| ENSANGP00000015780 [*Anopheles gambiae* str. PEST]

residues 126-153 of >ref|XP_314140.3| ENSANGP00000015780 [*Anopheles gambiae* str. PEST]

residues 5-34 of >emb|CAC35522.1| gSG6 protein [*Anopheles gambiae*]

(c) and from polypeptide sequences having 85% homology or more with one or more of the sequences in (a) or (b) and contained in one or more of the following databases: GenBank, Protein Data Bank (PDB), SwissProt, Protein Information Resource (PIR), Protein Research Foundation (PRF), or CDS translations of these.

CDS is short for "CoDing Sequence", i.e. a region of nucleotides that corresponds to the sequence of amino acids in a predicted protein. The CDS includes start and stop codons, therefore coding sequences begin with an "ATG" and end with a stop codon. Unexpressed sequences, including the 5'-UTR, the 3'-UTR, introns, or bases not expressed due to frameshifting, are not included within a CDS. Note that the CDS does not correspond to the actual mRNA sequence. As a result, a CDS translation is the protein that would result if all the codons between the start and stop codons were translated.

PDB stands for Protein Data Bank. This database (http://www.rcsb.org/pdb/home/home/do) is maintained by the Research Collaboratory for Structural Bioinformatics (RCSB), a non-profit consortium dedicated to improving the understanding of the function of biological systems through the study of the 3-D structure of biological macromolecules.

The Protein Information Resource (PIR) (http://pir.georgetown.edu/), is an integrated public bioinformatics resource established in 1984 by the National Biomedical Research Foundation (NBRF) as a resource to assist researchers in the identification and interpretation of protein sequence information (Wu C H, Yeh L S, Huang H, Arminski L, Castro-Alvear J, Chen Y, Hu Z, Kourtesis P, Ledley R S, Suzek B E, Garrett L, Vinayaka C R, Zhang J, Barker W C (2003). "The Protein Information Resource". *Nucleic Acids Res* 31(1):345-7.)

PRF is an online database maintained by the Protein Research Foundation (PRF) (http://www.prf.or.jp/en/index.shtml). The database contains information related to amino acids, peptides and proteins collected from scientific journals, peptide and Protein sequence data, data on synthetic compounds and molecular aspects of proteins.

GenBank is the NIH genetic sequence database (http://www.ncbi.nlm.nih.gov/), an annotated collection of all publicly available DNA sequences. A new release is made every two months. GenBank is part of the International Nucleotide Sequence Database Collaboration, which is comprised of the DNA DataBank of Japan (DDBJ), the European Molecular Biology Laboratory (EMBL), and GenBank at the National Center for Biotechnology Information.

Swissprot (also known as UniProtKB/Swiss-Prot) is a curated protein sequence database (http://expasy.org/sprot/) maintained by the Swiss Institute of Bioinformatics (SIB). The database strives to provide a high level of annotation (such as the description of the function of a protein, its domains structure, post-translational modifications, variants, etc.), a minimal level of redundancy and high level of integration with other databases.

These databases are updated weekly or monthly, and the sequences extend to those in the databases at the time of filing of this application. When finding sequences within the databases that have the desired homology, any method may be employed, depending on the match criteria. However, preferably the BLASTP program may be employed [BLAST and its derived programmes (e.g. BLASTP) are public domain software].

In another embodiment, instead of (or in addition to) the 85% homology referred to above in part (c), polypeptide sequences within the above databases are also included that have at least 85% of their amino acids in common (in terms of both amino acid identity, and position in the sequence) with a part of a sequence in (a) or (b) that 8 amino acids or more in length, and preferably from 8 amino acids in length up to one third of the length of the sequence in (a) or (b). In other words, for a sequence in (a) or (b) that is 30 amino acids long, a sequence in the database is also included if it shares 85% or more of its amino acids with any part of the sequence in (a) or (b) that is 8 amino acids long or greater, preferably from 8-10 amino acids. Similarly, if a sequence in (a) or (b) is 60 amino acids in length, a sequence in the database is also included if it shares 85% or more of its amino acids with any part of the sequence in (a) or (b) that is 8 amino acids long or greater, preferably from 8-20 amino acids. The matching amino acids need not be consecutive. For example, in the case of a 20 amino acid sequence in (a) or (b), where a corresponding database sequence shares 17 or more amino acids in the correct positions, it is included, even if these positions are not all consecutive.

Typically, the polypeptides in the composition are not complete (not full or not entire) arthropod saliva proteins. By complete (or full or entire) it is meant that the polypeptides do not contain all of the amino acid residues present in any of the naturally occurring arthropod saliva proteins.

Thus, the polypeptide is one that may comprise the whole of (or may comprise at least one 7 or more residue parts of) any of the above sequences. The polypeptide must also be immunogenic in a vertebrate. Typically this immunogenicity is such that the polypeptides cause the vertebrate to produce immune system cells capable of recognising at least one epitope from an arthropod saliva protein fraction. Thus, where a polypeptide elicits a T-cell or B-cell response, it is immunogenic in a vertebrate. The polypeptide may alternatively be a T helper lymphocyte (Th) epitope, or may be a B lymphocyte epitope.

One method for determining whether a polypeptide possesses immunogenicity is set out in Experiment 2 below. However, the present invention is not limited to such methods, and the skilled person may select any known method for determining immunogenicity, as desired.

It is particularly preferred that the polypeptides of the polypeptide composition are selected independently from SEQ ID 1-6, 20, 28, 30-32 and 35, or sub-sequences from these sequences, the sub-sequences having 7 amino acids or more, or from polypeptide sequences having 85% homology or more with one of these sequences and contained in one or more of the following databases: GenBank, Protein Data Bank (PDB), SwissProt, Protein Information Resource (PIR), Protein Research Foundation (PRF), or CDS translations of these.

Typically, but not exclusively, the polypeptide composition of the present invention, comprises 2 or more polypeptides, preferably from 2 to 10 polypeptides, or more preferably from 2-6 polypeptides. However, the composition may comprise a single polypeptide and further non-polypeptide components, if desired.

Generally, in the polypeptide composition according to the invention, the arthropod saliva protein fraction has a mass of 40 kDa or less, 30 kDa or less, or more preferably 20 kDa or less. The fraction may also have a mass of from 20-40 kDa, from 20-30 kDa, or from 10-20 kDa.

In another embodiment of the invention, the polypeptide composition of the invention comprises SEQ ID 131, or comprises one or more sub-sequences of SEQ ID 131 having 7 amino acids or more, or comprises polypeptide sequences having 85% homology or more with one of these sequences and contained in one or more of the following databases: GenBank, Protein Data Bank (PDB), SwissProt, Protein Information Resource (PIR), Protein Research Foundation (PRF), or CDS translations of these.

SEQ ID 131
FLKGSFPRFQMCVMLIGFFSSAKCLFYSVGKLVKVLLVMAVCCLLLCTAP

TGADPLMKFAFAFVLIALFAVFAVSQALPQPEQAAAGRVMCLLRLMSTLL

VVLSIVGKLYSGYRLLVLLVMTVCCLLLFIAPTGADPLPGQTQRTLALIG

LLLCSVQSVTANDPVDALGACSGNLFGLLMTRLSKLFVLAFLCLALVVVV

QSAPQYARGDVPTLLPAKVIPDKTAAYVAYGGQETLVEHVEVLVRYFVVI

ALICPLIIVETLAVVLLTPALQAYIMDEHNLNRSNIALGRIRPYPSAVKM

PVLHSMLVNASLAEMVKESYQTHGADGRMVVRMLKFVRLLPRVRALRALL

ETLLQHQGEQNNDVYLIRLAHETELQQALSSLNAGSGSCAEVFNAYLPVH

NKYIGVSRKIQYSMECLEAAEPKYLDGLKTLADETAQCSFAWLLYGIILR

SNFLVVQNLMALALSAVQLSLFIIAFPFISGFLSCFMWLKYGVLTEESTL

ILVNFIGSAL

In another embodiment of the invention the polypeptide composition of the invention comprises one or more sequences selected from SEQ ID 1-4, 6, 9, 10, 13, 14, 17-19, 21-25, 27, 29, 33, 34, 36-40, 43, and 44 or comprises one or more sub-sequences of these sequences having 7 amino acids or more, or comprises polypeptide sequences having 85% homology or more with one of these sequences and contained in one or more of the following databases: GenBank, Protein Data Bank (PDB), SwissProt, Protein Information Resource (PIR), Protein Research Foundation (PRF), or CDS translations of these.

In a further embodiment, the polypeptide composition of the invention comprises SEQ ID 132, or comprises one or more sub-sequences of SEQ ID 132 having 7 amino acids or more, or comprises polypeptide sequences having 85% homology or more with one of these sequences and contained in one or more of the following databases: GenBank, Protein Data Bank (PDB), SwissProt, Protein Information Resource (PIR), Protein Research Foundation (PRF), or CDS translations of these.

SEQ ID 132
HLTLFTVAVLLLAAAALLLLLPPAYSTTLTPPPLSYCHLFLTHTLARALS

FSRSDCLKNVFFALLLVVLVCCLVSVQGNEIKLLVLLICLFFYHTHCTTA

YLWLAMGVNDYQALLGLCCPWIDLAAADLPMRRHAKADGASAITKIVLEL

TPEQAAAVTLFIFLVCCQIPLFGIMSSDSADPFYWIRVILAMYCVIKGKT

-continued

```
GGYCNSEGLCTCRAEDLHFLLKPIINKDNAEDPRTELIGCGSVLFHLAAN

RLSLQLEEFAVCKRSMLVAFATLSVALVVVVAIPANFNYGGGGGYFINGT

GQIYEKLPAYLSEVSARVNVLQVSLQHDLPNLQEMISLWFMAWTPYLVIN

FTGIFYTCFLGTSSLAGFKNAVDYDELLKAGVLEVLGFVEDNKLAKVALV

TGELVFQELLGVLKMVDPDGDKLTPTVVVVLLCLTFVADALTIQELRAQI

AQQRIQQRYGVTVATTSLSDYGLIELKEHCLECCQKDTEADSKLKVYPAA

VLEVTYICFILHGVSEIIPQQQKKTMKFLLLVASVLCLVLILLLYLDAAD

LRRALHQYQLLAAQGDRHLPQQIVKFVVLKGETHKALKLKDGGHYLVEFK

SIYMKFYRLISTLLVVVVIAPRHQCSPFFFQYNRPYLNYVPDVSALEQDI

IEVDPETKEMLKHLDFNNIVVQLEYAQVTKMLGNGRLEAMCFDGVKRLCH

IRGKLKLFLTLLSTLSVAMVFALPAHHHSRGELEEARLVAEELEERQQEL

DYLKRYLVGRLQAVSYFLTVCLLALVQSETVQDAMTNANLVGLTISLAYA

IFFLLYTPPTGRSSGLLCCCLAVLFFASPLTMLAHVIRLLLAMVLLPLLL

LESVVPYAAAEKVW
```

In a still further embodiment, the polypeptide composition of the invention comprises SEQ ID 133, or comprises one or more sub-sequences of SEQ ID 133 having 7 amino acids or more, or comprises polypeptide sequences having 85% homology or more with one of these sequences and contained in one or more of the following databases: GenBank, Protein Data Bank (PDB), SwissProt, Protein Information Resource (PIR), Protein Research Foundation (PRF), or CDS translations of these.

```
                                              SEQ ID 133
HLTLFTVAVLLLAAAALLLLLPPAYSTTLTPPPLSYCHLFLTHTLARALS

FSRSDCLKNVFFALLLVVLVCCLVSVQGNEIKLLVLLICLFFYHTHCTTA

YLWLAMGVFLKGSFPRFQMCVMLIGFFSSAKCLNDYQALLGLCCPWIDLA

AADLPMRRHAKA
```

In a yet further embodiment, the polypeptide composition of the invention comprises SEQ ID 134, or comprises one or more sub-sequences of SEQ ID 134 having 7 amino acids or more, or comprises polypeptide sequences having 85% homology or more with one of these sequences and contained in one or more of the following databases: GenBank, Protein Data Bank (PDB), SwissProt, Protein Information Resource (PIR), Protein Research Foundation (PRF), or CDS translations of these.

```
                                              SEQ ID 134
LLPAKVIPDKTAAYVAYGGQETLVEHVEVLVVLLTPALQAYIMDEHNLNR

SNIALGRIRPYPSAVKMPVLHSMLVNASLAEMVKESYQTHGADGRMVVRM

LKFVRLLPRVRALRALLETLLQHQGEQNNDVYLIRLAHETELQQALSSLN

AGSGSCAEVFNAYLPVHNKYIGVSRKIQYSMECLEAAEPKYLDGLKTLAD

ETAQC
```

Importantly, in all embodiments of the invention, any combination of the listed sequences may be employed, either alone or in combination. Particularly preferred polypeptides are those having sequences of SEQ ID 1-6, and/or those having sequences of SEQ ID 20, 28, 30-32 and 35. It is especially preferred that any one or more of these are present, and particularly preferred that all of SEQ ID 1-6 and/or all of SEQ ID 20, 28, 30-32 and 35 are present.

The present inventors have found that the above sequences comprise an epitope, or a plurality of epitopes, which may afford protection against arthropod borne diseases for a wide variety of vertebrates in a population. Arthropod bites induce in the host an immune responses to the saliva components that is characterised by a Th2 phenotype (i.e. downregulation of IFN-γ production and upregulation of IL-4 production) (Mbow et al, 1998). This immune response, together with the antiheamostatic effect of many of these salivary molecules, has been found to facilitate and enhance parasite transmission in general (Dhar and Kumar, 2003) and to promote *Leishmania* infection in particular (Kamhawi et al., 2000). In contrast, an increase in the cellular immune response characterised by increased production of IFN-γ and IL-12, both Th1 type cytokines, at the site of infection (i.e. the bite site) has been shown to induce protection against *Leishmania major* infection by the bite of infected sandflies (Kamhawi et al., 2000).

Without being bound by theory, it is believed that immunisation with salivary proteins leading to the activation of a Th1 type response will lead to the rapid recognition of salivary antigens at the bite site by cells of the immune system (such as activated cytotoxic T cells (CTLs) and T helper type 1 cells) and the production of IFN-γ. This cytokine (1) stimulates both T and NK cells to produce more IFN-γ, (2) promotes the microbicidal activity of macrophages, (3) induces isotype switching to and increased production of IgG2a by B cells and, (4) the production of multiple cytokines (e.g. TNF-α, interleukin (IL) 12 and IL-18) which combined trigger a cascade of immune reactions that lead to the death of intracellular parasites. References detailing this are set out below.

Mbow M L, Bleyenberg J A, Hall L R & Titus R G. 1998. *Phlebotomus papatasi* sandfly salivary gland lysate downregulates a Th1, but up-regulates a Th2, response in mice infected with *Leishmania* major. J. Immunol; 161: 5571-5577.

Dhar, R., Kumar, N., 2003. Role of mosquito salivary glands. Cur. Sci. 85, 1308-1313. Kamhawi, S., Belkaid, Y., Modi, G., Rowton, E., Sacks, D., 2000. Protection against cutaneous leishmaniasis resulting from bites of uninfected sand flies. Science 290, 1351-1354

Malaguarnera L, Musumeci S. 2002. The immune response to *Plasmodium falciparum* malaria. Lancet Infect Dis. August; 2(8):472-8

As discussed above, the sequences have been identified after analysis of saliva sequences in *Anopheles gambiae*. It will be apparent to the skilled person that the invention extends not only to the sequences and their epitopes, but also to larger sequences in arthropod saliva proteins containing these sequences, and to sequences that are homologous to these sequences and so have immunogenic activity. Thus, sequences with some homology to the consensus sequences are also within the scope of the invention. Such homology allows substitution of, for example, up to 3 amino acids in an 8-mer epitope (62.5% homology) or in a 9-mer, 10-mer, or 11-mer epitope. It is preferred that no more than 10 such substitutions are identifiable in a sequence of the invention corresponding to the full sequences of SEQ ID 1-44 (66.6% homology for a 30-mer). Such substitutions are preferably conservative substitutions in line with known substitution schemes.

The invention also provides a polypeptide comprising one or more sequences defined by the following sequences SEQ ID 1-44, or the following amino acid residues of an arthropod saliva protein, or comprising one or more sub-sequences from these sequences, the sub-sequences having 7 amino acids or more, or comprising polypeptide sequences having 85% homology or more with one of the sequences and contained in one or more of the following databases: GenBank, Protein Data Bank (PDB), SwissProt, Protein Information Resource (PIR), Protein Research Foundation (PRF), or CDS translations of these.

SEQ ID 1    HLTLFTVAVLLLAAAALLLLLPPAYSTTLTPP
SEQ ID 2    PLSYCHLFLTHTLARALSFSRSDCL
SEQ ID 3    KNVFFALLLVVLVCCLVSVQGNEI
SEQ ID 4    KLLVLLICLFFYHTHCTTAYLWLAMGV
SEQ ID 5    FLKGSFPRFQMCVMLIGFFSSAKCL
SEQ ID 6    NDYQALLGLCCPWIDLAAADLPMRRHAKA
SEQ ID 7    FYSVGKLVKVLLVMAVCCLLLCTAPTGADPL
SEQ ID 8    MKFAFAFVLIALFAVFAVSQALPQPEQAAA
SEQ ID 9    DGASAITKIVLELTPEQAAAV
SEQ ID 10   TLFIFLVCCQIPLFGIMSSDSADPFYWIRVILA
SEQ ID 11   GRVMCLLRLMSTLLVVLSIVGK
SEQ ID 12   LYSGYRLLVLLVMTVCCLLLFIAPTGADPLPGQTQRTL
SEQ ID 13   MYCVIKGKTGGYCNSEGLCTCRAEDLHFLLKPIINKD
SEQ ID 14   NAEDPRTELIGCGSVLFHLAANRLSLQLEEFAVCKR
SEQ ID 15   ALIGLLLCSVQSVTANDPVDALGACSGNLFGLLMTRL
SEQ ID 16   SKLFVLAFLCLALVVVVQSAPQYARGDVPT
SEQ ID 17   SMLVAFATLSVALVVVVAIPANFNYGGGGGYFINGTGQ
SEQ ID 18   IYEKLPAYLSEVSARVNVLQVSLQHDLPNLQ
SEQ ID 19   EMKLAKVALVTISLWFMAWTPYLVINFTGI
SEQ ID 20   LLPAKVIPDKTAAYVAYGGQETLVEHVEVLV
SEQ ID 21   FYTCFLGTSSLAGFKNAVDYDELLKAG
SEQ ID 22   VLEVLGFVEDNGELVFQELLGVLKMVDPDGD
SEQ ID 23   KLTPTVVVVLLCLTFVADALTIQELRAQIAQQRIQQRYGV
            TVATT
SEQ ID 24   SLSDYGLIELKEHCLECCQKDTEADSKLKVYPAAVLEV
SEQ ID 25   TYICFILHGVSEIIPQQQKKTMKFLLLVASVLCLVLI
SEQ ID 26   RYFVVIALICPLIIVETLAV
SEQ ID 27   LLLYLDAADLRRALHQYQLLAAQGDRHLPQQIVKFV
SEQ ID 28   VLLTPALQAYIMDEHNLNRSNIALGRIRPYPSAVKMP
SEQ ID 29   VLKGETHKALKLKDGGHYLVEFKSIYM
SEQ ID 30   VLHSMLVNASLAEMVKESYQTHGADGRMVVRMLKFVRLLP
SEQ ID 31   RVRALRALLETLLQHQGEQNNDVYLIRLAHET
SEQ ID 32   ELQQALSSLNAGSGSCAEVFNAYLPVHNKYIGVSRKI
SEQ ID 33   KFYRLISTLLVVVVIAPRHQCSPFFFQYNRPYL
SEQ ID 34   NYVPDVSALEQDIIEVDPETKEMLKHLDFNNIVVQL
SEQ ID 35   QYSMECLEAAEPKYLDGLKTLADETAQC
SEQ ID 36   EYAQVTKMLGNGRLEAMCFDGVKRLCHIRGKL
SEQ ID 37   KLFLTLLSTLSVAMVFALPAHHHSRG
SEQ ID 38   ELEEARLVAEELEERQQELDYLKRYLVGRLQAV
SEQ ID 39   SYFLTVCLLALVQSETVQD
SEQ ID 40   AMTNANLVGLTISLAYAIFFLLYTPPTGRSS
SEQ ID 41   SFAWLLYGIILRSNFLVVQNLMALALSAVQLSLFII
SEQ ID 42   AFPFISGFLSCFMWLKYGVLTEESTLILVNFIGSAL
SEQ ID 43   GLLCCCLAVLFFASPLTMLAHVIR
SEQ ID 44   LLLAMVLLPLLLLESVVPYAAAEKVW residues 2-33 of >gi|18389913|gb|AAL68793.1|AF457563_1 hypothetical protein 16 [Anopheles gambiae]
residues 2-26 of >gi|18389909|gb|AAL68791.1|AF457561_1 hypothetical protein 14 [Anopheles gambiae]
residues 2-25 of >gi|18389907|gb|AAL68790.1|AF457560_1 hypothetical protein 13 [Anopheles gambiae]
residues 10-36 of >gi|18389903|gb|AAL68788.1|AF457558_1 hypothetical protein 11 [Anopheles gambiae]
residues 2-26 of >gi|62546227|gb|AAX86005.1|hyp3.5 precursor [Anopheles gambiae]
residues 14-42 of gi|18389899|gb|AAL68786.1|AF457556_1 salivary gland 7-like protein [Anopheles gambiae]
residues 3-33 of >gi|18389911|gb|AAL68792.1|AF457562_1 hypothetical protein 15 [Anopheles gambiae]
residues 1-30 of >gi|62546225|gb|AAX86004.1|hyp6.3 precursor [Anopheles gambiae]
residues 34-54 of >gi|62546225|gb|AAX86004.1|hyp6.3 precursor [Anopheles gambiae]
residues 38-70 of >gi|17026153|emb|CAD12038.1|Sec61 protein [Anopheles gambiae]
residues 2-23 of >gi|62546223|gb|AAX86003.1|hyp6.2 precursor [Anopheles gambiae]
residues 17-54 of >gi|18389915|gb|AAL68794.1|AF457564_1 hypothetical protein 17 [Anopheles gambiae]
residues 57-93 of >gi|87080391|gb|ABD18596.1|defensin [Anopheles gambiae]
residues 22-57 of >gi|18389901|gb|AAL68787.1|AF457557_1 hypothetical protein 10 [Anopheles gambiae]
residues 7-43 of >gi|18389905|gb|AAL68789.1|AF457559_1 hypothetical protein 12 [Anopheles gambiae]
residues 3-32 of >gi|4127344|emb|CAA76832.1| cE5 protein [Anopheles gambiae]
residues 3-40 of >gi|4210617|emb|CAA10259.1| SG2 protein [Anopheles gambiae]
residues 91-121 of >gi|4127309|emb|CAA76820.1| hypothetical protein [Anopheles gambiae]
residues 65-94 of >gi|4375824|emb|CAA76825.1| opsin [Anopheles gambiae]
residues 41-71 of >gi|62546233|gb|AAX86008.1| unknown [Anopheles gambiae]

residues 117-143 of >gi|3378531|emb|CAA03872.1| D7r2 protein [*Anopheles gambiae*]

residues 63-93 of >gi|3378529|emb|CAA03871.1| D7r3 protein [*Anopheles gambiae*]

residues 23-67 of >gi|18389893|gb|AAL68783. 1|AF457553_1 mucin-like protein [*Anopheles gambiae*]

residues 43-80 of >gi|18389881|gb|AAL68777. 1|AF457547_1 selenoprotein [*Anopheles gambiae*]

residues 6-42 of >gi|18389879|gb|AAL68776. 1|AF457546_1 30 kDa protein [*Anopheles gambiae*]

residues 4-23 of >gi|18378603|gb|AAL68639. 1|AF458073_1 D7-related 5 protein [*Anopheles gambiae*]

residues 20-55 of >gi|18389897|gb|AAL68785. 1|AF457555_1 salivary gland 1-like 4 protein [*Anopheles gambiae*]

residues 59-95 of >gi|18389883|gb|AAL68778. 1|AF457548_1 antigen 5-related 1 protein [*Anopheles gambiae*]

residues 158-184 of >gi|83016748|dbj|BAE53441. 1|DsRed [synthetic construct]

residues 37-76 of >gi|18389895|gb|AAL68784. 1|AF457554_1 salivary gland 1-like 3 protein [*Anopheles gambiae*]

residues 191-222 of >gi|18389895|gb|AAL68784. 1|AF457554_1 salivary gland 1-like 3 protein [*Anopheles gambiae*]

residues 113-149 of >gi|18389891|gb|AAL68782. 1|AF457552_1 D7 protein long form [*Anopheles gambiae*]

residues 3-35 of >gi|13537676|emb|CAC35527.1|gSG9 protein [*Anopheles gambiae*]

residues 83-118 of sp|Q9U9L1|RS17_ANOGA 40S ribosomal protein S17 and gb|AAD47077.1|AF164153_1 ribosomal protein S17 [*Anopheles gambiae*]

residues 113-140 of >emb|CAC35523.1| gSG7 protein [*Anopheles gambiae*]

residues 34-65 of >gb|AAD47075.1|AF164151_1 translation initiation factor 4C (1A) [*Anopheles gambiae*]

residues 2-27 of >emb|CAC35519.1| gSG2-like protein [*Anopheles gambiae*]

residues 108-140 of >emb|CAC35451.1| hypothetical protein [*Anopheles gambiae*] and >gb|EAU75730.1| ENSANGP00000031975 [*Anopheles gambiae* str. PEST]

residues 8-26 of >emb|CAC35524.1| D7r4 protein [*Anopheles gambiae*] and >gb|AAK84945.1| D7-related 4 protein [*Anopheles gambiae*]

residues 72-102 of >ref|XP_001230998.1| ENSANGP00000014906 [*Anopheles gambiae* str. PEST] and gb|EAU76798.1| ENSANGP00000014906 [*Anopheles gambiae* str. PEST]

residues 176-211 of >ref|XP_316361.2| ENSANGP00000012984 [*Anopheles gambiae* str. PEST] and >gb|EAA10852.2| ENSANGP00000012984 [*Anopheles gambiae* str. PEST]

residues 43-78 of >ref|XP_314140.3| ENSANGP00000015780 [*Anopheles gambiae* str. PEST] and gb|EAA09398.3| ENSANGP00000015780 [*Anopheles gambiae* str. PEST]

residues 128-151 of >ref|XP_314140.3| ENSANGP00000015780 [*Anopheles gambiae* str. PEST] and gb|EAA09398.3| ENSANGP00000015780 [*Anopheles gambiae* str. PEST]

residues 7-32 of >emb|CAC35522.1| gSG6 protein [*Anopheles gambiae*]

Preferably, the polypeptide is not a complete arthropod saliva protein.

The sequence numbering referred to in the present invention is defined according to well-recognised principles. Thus, the numbering begins at 1 from the recognised translation initiation codon (ATG). This corresponds to a Methionine (M), for the segment of the genome coding for the protein of interest. In other words, it begins at 1 in respect of the Methionine shown as the first amino acid in the protein sequence of interest as used and defined by the databases in which the sequences have been set forth (i.e. GenBank, SwissProt, etc.).

The present invention will be described in more detail by way of example only with reference to the following Figures, in which.

| | |
|---|---|
| 3A: Percent that fed | 3B: Mean no eggs produced |
| 3C: Mean no eggs laid | 3D: Percent hatch rate |
| 3E: Mean no larvae | 3F: Mean no pupae |
| 3G: Percent pupation | 3H: Percent emergence |
| 3I: Mean no adults | |

Figure 4:
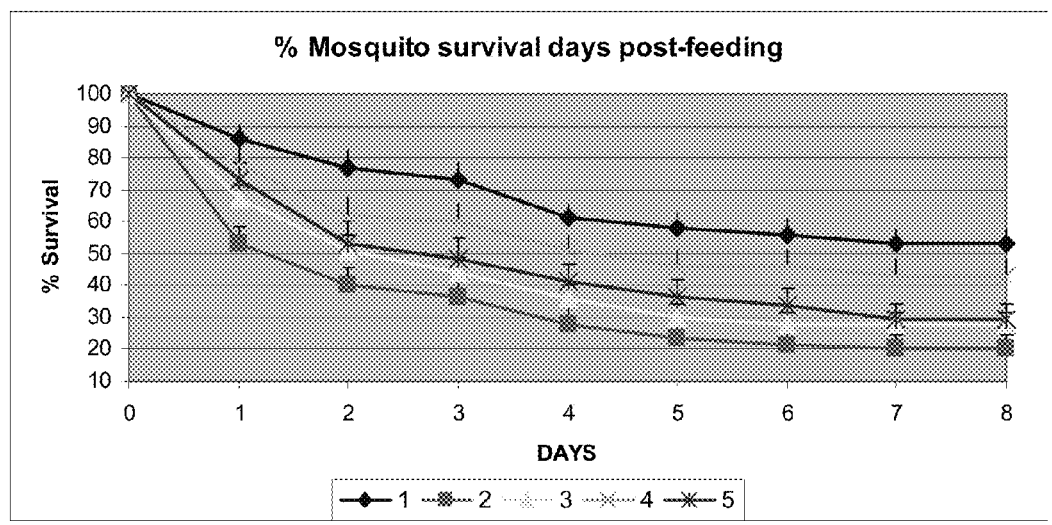

FIG. 4 shows the data on the percent survival of mosquitoes after feeding on immunized mice.

Figure 5:
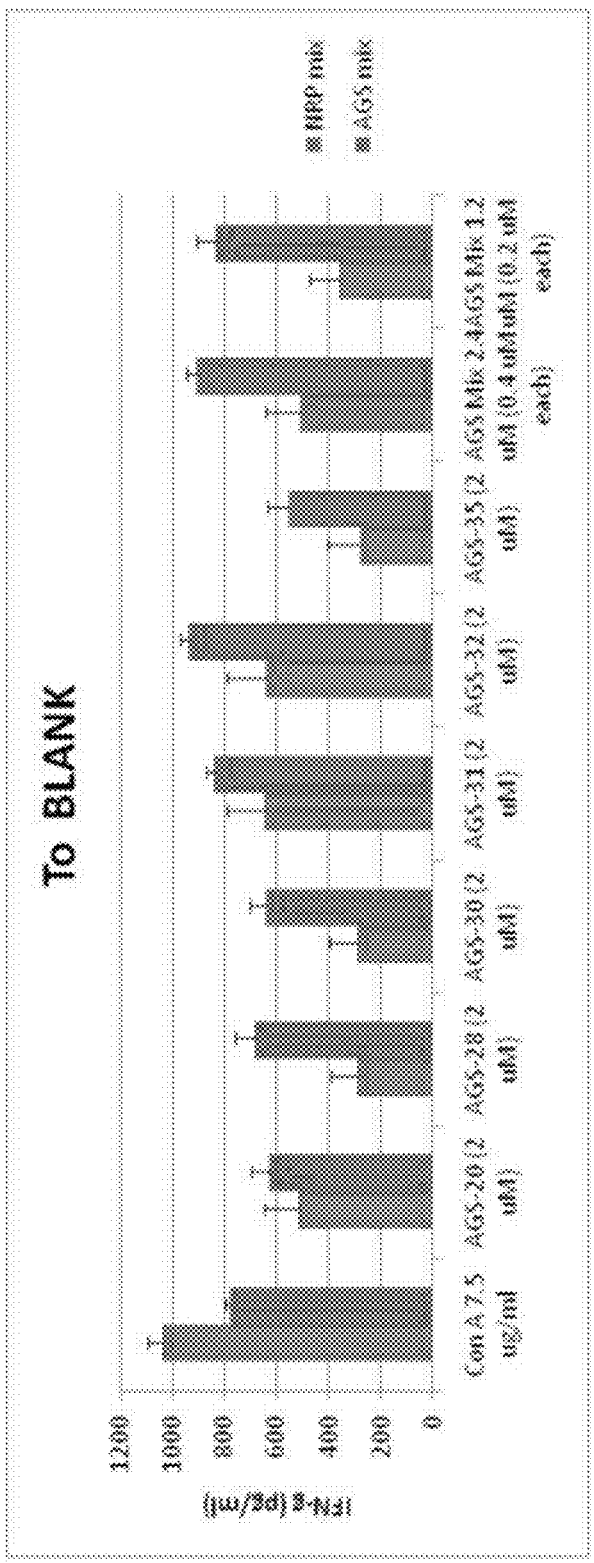

FIG. 5 shows IFN-gamma production following 96 hour stimulation in vitro with the antigens in Experiment 3.

Figure 6:
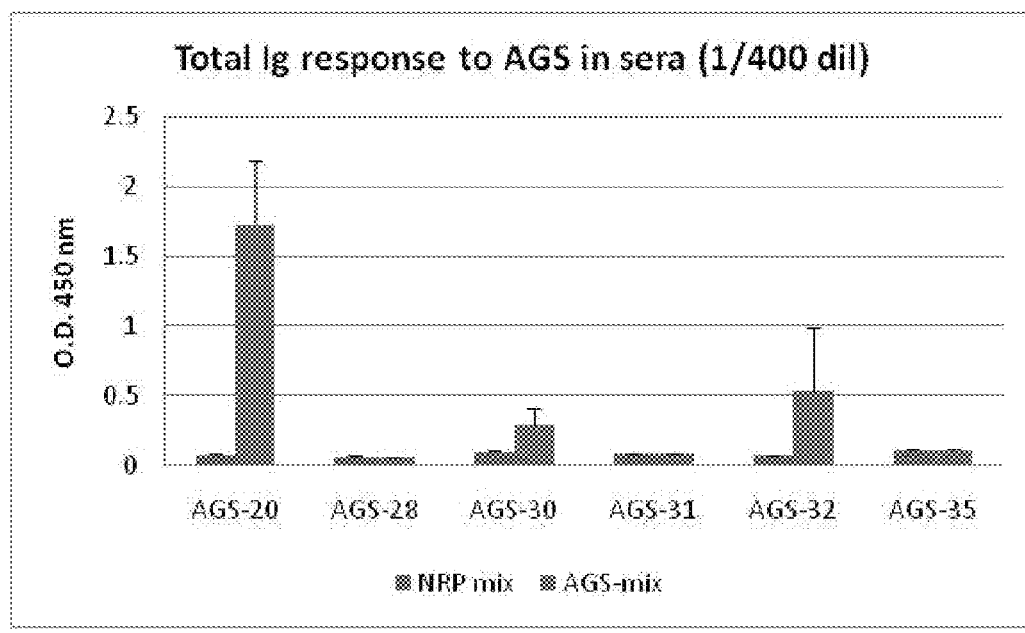

FIG. 6 shows the total Ig response in sera to the antigens according to Experiment 3.

Figure 7:
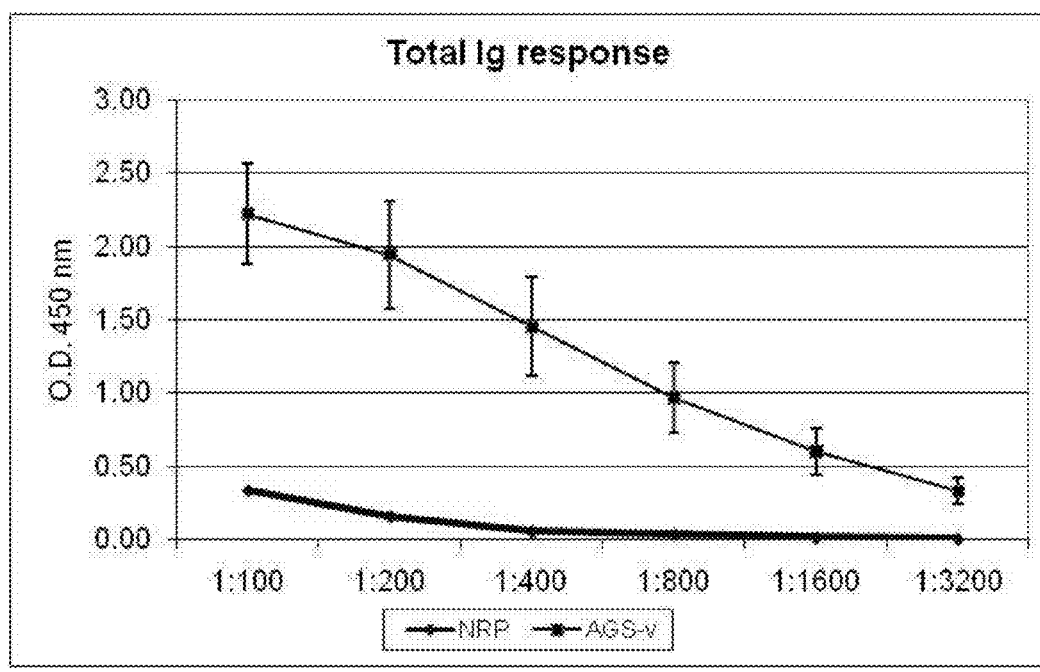

FIG. 7 shows total Ig response in sera to the AGS-mix at day 21 in accordance with Experiment 4.

Figure 8:
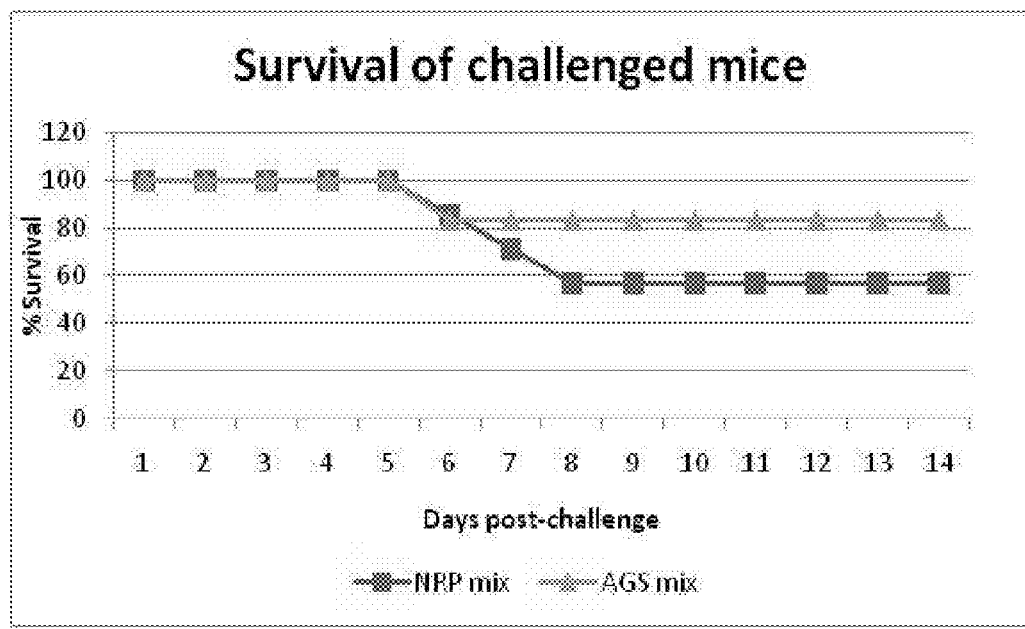

FIG. 8 shows the AGS-mix immunised group of Experiment 4 displaying an increased survival rate as compared with those in the control NRP-mix immunised group.

The polypeptide described above typically comprises one or more (preferably two or more) epitopes. These epitopes are preferably T cell epitopes, such as cytotoxic T lymphocyte (CTL) epitopes, but may also contain B cell epitopes. Generally the polypeptide is immunogenic to an arthropod saliva protein, and preferably to a plurality of such proteins. In the present context, a polypeptide immunogenic to an arthropod saliva protein is understood to mean a polypeptide that is part of an arthropod saliva protein and that elicits an immune system response. One method for determining whether a polypeptide possesses such immunogenicity is set out in Experiment 2 below. However, the present invention is not limited to such methods, and the skilled person may select any known method for determining immunogenicity, as desired.

In the present invention, the polypeptide composition comprises one or more sequences as described above. Typically, two, three, four, five or more such sequences may be present in the polypeptide, if desired. The more such epitopes are present, the greater the breadth of protection afforded within a population of humans and/or animals individuals with differing HLAs or MHCs. This is particularly so if the epitopes included are from the saliva of a plurality of differing arthropods or shared by salivary proteins of different arthropod species, and can thus offer protection against diseases carried by a plurality of different arthropods. Typically the polypeptide composition comprises 10 polypeptides or fewer, preferably 6 polypeptides or fewer, and typically from 2-10 polypeptides, and more preferably from 2-6 polypeptides.

The polypeptide composition according to the present invention may also comprise one or more further sequences that are not epitopes, if desired. Typically the further sequences are from one or more arthropod saliva proteins, preferably selected from the sequences of SEQ ID 45-85 or sub-sequences of these. These sequences may be situated between two or more of the sequences (the epitopes) described above, or may be situated at one or both ends of the polypeptide. The presence of such further sequences should not affect the function of the polypeptide, provided that the polypeptide as a whole does not become too large, interfering with the presentation of the epitopes in the vertebrate's immune system.

In the most preferred embodiments, the further sequences from the above-mentioned proteins are ones that are (or are within) the following sequences:

```
SEQ ID 45 - >gi|18389913|gb|AAL68793.1|AF457563_ 1 hypothetical protein 16 [Anopheles
gambiae]
MHLTLFTVAVLLLAAAALLLLLPPAYSTTLTPPAPPRLSHLGITIGRI SEQ ID 46 - >gi|18389909|gb|AAL68791.1|AF457561_ 1 hypothetical protein 14 [Anopheles
gambiae]
MPLSYCHLFLTHTLARALSFSRSDCLKFSEKRLLFSGSKTFPTTLL SEQ ID 47 - >gi|18389907|gb|AAL68790.1|AF457560_ 1 hypothetical protein 13 [Anopheles
gambiae]
MKNVFFALLLVVLVCCLVSVQGNEIIQNVVKRSIPLRQLILQHNALDDSNSDSGSQ SEQ ID 48 - >gi|18389903|gb|AAL68788.1|AF457558_ 1 hypothetical protein 11 [Anopheles
gambiae]
MCIFFQAGIKLLVLLICLFFYHTHCTTAYLWLAMGVEAKSIKARGTAHSKSRTSTN SEQ ID 49 - >gi|62546227|gb|AAX86005.1|hyp3.5 precursor [Anopheles gambiae]
MFLKGSFPRFQMCVMLIGFFSSAKCLMCFADWEGMLLMTMEVFDFQLIVFTPVLKRS SEQ ID 50 - >gi|18389899|gb|AAL68786.1|AF457556_ 1 salivary gland 7-like protein
[Anopheles gambiae]
MAGESQKNARSKQNDYQALLGLCCPWIDLAAADLPMRRHAKAREAINFLLQAHEA
GPNEEPSLPA SEQ ID 51 - >gi|18389911|gb|AAL68792.1|AF457562_ 1 hypothetical protein 15 [Anopheles
gambiae]
MKFYSVGKLVKVLLVMAVCCLLLCTAPTGADPLPGRDRNTIANKSKDKKASAPKHS
LGTGARMALTGGGVLGGVLTNM SEQ ID 52 - >gi|62546225|gb|AAX86004.1|hyp6.3 precursor [Anopheles gambiae]
MKFAFAFVLIALFAVFAVSQALPQPEQAAASSNDGASAITKIVLELTPEQAAAVQKM
GGRGFWPIMMKSVKKIMAIGCDLIDC SEQ ID 53 - >gi|17026153|emb|CAD12038.1|Sec61 protein [Anopheles gambiae]
MGIKFLEIIKPFCGILPEIAKPERKIQFREKVLWTAITLFIFLVCCQIPLFGIMSSDSADPF
YWIRVILASNRGTLM SEQ ID 54 - >gi|62546223|gb|AAX86003.1|hyp6.2 precursor [Anopheles gambiae]
MGRVMCLLRLMSTLLVVLSIVGKKTNAAPQVTEAPGNVGSTYSPMADIGRLATGAT
KLFGQFWNTGTRFGTELSRRTFDFLRVKK SEQ ID 55 - >gi|18389915|gb|AAL68794.1|AF457564_ 1 hypothetical protein 17 [Anopheles
gambiae]
MAGDIQLFSTRETTMKLYSGYRLLVLLVMTVCCLLLFIAPTGADPLPGQTQRTLGYR
GNDKRATPPMHSLGSGARMAMTGGGILGGIFSAL SEQ ID 56 - >gi|87080391|gb|ABD18596.1|defensin [Anopheles gambiae]
MDQCSVPRLCIIIMKSFIAAAVIALICAIAVSGTTVTLQSTCKLFTADVVSSITCKMYC
VIKGKTGGYCNSEGLCTCRAEDLHFLLKPIINKD SEQ ID 57 - >gi|18389901|gb|AAL68787.1|AF457557_ 1 hypothetical protein 10 [Anopheles
gambiae]
MRFLSVLTVGLLVWVGVFATVNAEDPRTELIGCGSVLFHLAANRLSLQLEEFAVCK
RSNPGYDCSDSIHRAISDLQQGLFDLNHCTKDIR SEQ ID 58 - >gi|18389905|gb|AAL68789.1|AF457559_ 1 hypothetical protein 12 [Anopheles
gambiae]
MRFCCVALIGLLLCSVQSVTANDPVDALGACSGNLFGLLMTRLQQMVEDFTACRQE
ATANDPQHDRSDSIQRAKVDLQQQLVNYSYCTKNIQ SEQ ID 59 - >gi|4127344|emb|CAA76832.1|cE5 protein [Anopheles gambiae]
MASKLFVLAFLCLALVVVVQSAPQYARGDVPTYDEEDFDEESLKPHSSSPSDDGEEE
FDPSLLEEHADAPTARDPGRNPEFLRNSNTDEQASAPAASSSDS
```

-continued

SEQ ID 60 - >gi|4210617|emb|CAA10259.1|SG2 protein [Anopheles gambiae]
MKSMLVAFATLSVALVVVVAIPANFNYGGGGGYFINGTGQSFNFSGESNGTSIPGLP
DFGSFLPNLGNLTQQFGGSSGAFPQFSIPSWTNFTDAFTSILPFFGNGQGGGFPFFG SEQ ID 61 - >gi|4127309|emb|CAA76820.1|hypothetical protein [Anopheles gambiae]
MTPLIATLAACALTLSIVHSRGLPESSDKLEACGQHYGXLLKASTTWNEKECNGSTK
LAACVVSEHEQAYRELKQRCQEAHDERTAKVNAIYEKLPAYLSEVSARVNVLQVSL
QHDLPNLQE SEQ ID 62 - >gi|4375824|emb|CAA76825.1|opsin [Anopheles gambiae]
PDVAEPLVHHHLRHLRVLAAAADHHLLVHLHPEGCVRSREEHARAGQEGNVASLR
TQEAQNTSTEMKLAKVALVTISLWFMAWTPYLVINFTGIFKAAPISPLATIRGSLFAK
ANAVYNPIVYG SEQ ID 63 - >gi|62546233|gb|AAX86008.1|unknown [Anopheles gambiae]
MATTWIPTSVHGPYPPHMVPGGVDSDGAQIFVGRAHHAGDLLPAKVIPDKTAAYVA
YGGQETLVEHVEVLVHKQLIWDTASAGQVPLGAVVGGHTSDGEILYVGRAYHEGS
QTIGKVQCSHNCIYIPYGGAEVSVPTYEVLCER SEQ ID 64 - >gi|3378531|emb|CAA03872.1|D7r2 protein [Anopheles gambiae]
MFKKLLLSVGLVWCLISLGQARKESTVEECEKNIGDSLKDRVCELRQYTPVSSDDM
DKHMQCVLEVVGFVDGNGEVKESVLLELLQRVDSGVNHAANMKKCVTEASTSGSD
KKANTFYTCFLGTSSLAGFKNAVDYDELLKAGKMQTSDP SEQ ID 65 - >gi|3378529|emb|CAA03871.1|D7r3 protein [Anopheles gambiae]
MFGKLLPCAILLWCLFSLGQARQEETVEECERNIPASLKERVCELRQYTPVQGKDMD
SHMQCVLEVLGFVEDNGELVFQELLGVLKMVDPDGDHAGSMKKCNGEAEKVDTSS
KANTFYTCFLGTSSAQAFKYAVDYVXAXRAGKLDMGTTFNAGQV SEQ ID 66 - >gi|18389893|gb|AAL68783.1|AF457553_ 1 mucin-like protein [Anopheles gambiae]
AGGFSLFEALKQTTTRGEMFRRKLTPTVVVVLLCLTFVADALTIQELRAQIAQQRIQQ
RYGVTVATTSAATTTAATTSAATTSEATTTAAASTTQASDSDNTTTTAEATTTTEAQ
TTSSSDNSTTTEAAATTTAASETTADSSTGTTSVEAGLRAQYRDQVRQQAIERALA
RAAAFG SEQ ID 67 - >gi|18389881|gb|AAL68777.1|AF457547_ 1 selenoprotein [Anopheles gambiae]
MRLFAITCLLFSIVTVIGAEFSAEDCRELGLIKSQLFCSACSSLSDYGLIELKEHCLECC
QKDTEADSKLKVYPAAVLEVCTCKFGAYPQIQAFIKSDRPAKFPNLTIKYVRGLDPIV
KLMDEQGTVKETLSINKWNTDTVQEFFETRLAKVEDDDYIKTNRV SEQ ID 68 - >gi|18389879|gb|AAL68776.1|AF457546_ 1 30 kDa protein [Anopheles gambiae]
MAGAITYICFILHGVSEIIPQQQKKTMKFLLLVASVLCLVLIVSARPADDTSDQESSTE
LSDDAGAEEGAEDAGSDAEADAGAADGEEGATDTESGAEGDDSEMDSAMKEGEEG
AGSDDAVSGADDETEESKDDAEEDSEEGGEEGGDSASGGEGGEKESPRNTYRQVHK
LLKKIMKVDTKD SEQ ID 69 - >gi|18378603|gb|AAL68639.1|AF458073_ 1 D7-related 5 protein [Anopheles gambiae]
MEWRYFVVIALICPLIIVETLAVSDCVRHVSESARNTVCDVRQYRVTKGVEADRYVQ
CFMTALGFADESGSIQRSNVLTALDAVETHDGVYTDAVDVCLSKAKKLPGTERSGY
FFSCMLRTESALNFRDAVELQELRVASKWPEGERFDRSKVQQMMRELNSQLRC SEQ ID 70 - >gi|18389897|gb|AAL68785.1|AF457555_ 1 salivary gland 1-like 4 protein [Anopheles gambiae]
GREAIETMRTEQRNHRQQLLLLYLDAADLRRALHQYQLLAAQGDRHLPQQIVKFVY
AAPRHENRRLENLLDLVRQLPARQDQRTLYQLLQPEIMKRPAQNQSTLAMLTALEM
GQVVEGNGELKKQQDAMYQLVLKRWMFLCLAGQYREIVQFATKHPRLFE SEQ ID 71 - >gi|18389883|gb|AAL68778.1|AF457548_ 1 antigen 5-related 1 protein [Anopheles gambiae]
MAIWIVCATLLLAVLSVVSVGGQYCSSDLCPRGGPHVGCNPPSSSGGPTCQGKQKA
RKVLLTPALQAYIMDEHNLNRSNIALGRIRPYPSAVKMPTLTWDPELASLADANARS
CNYGHDRCRATKKFPYAGQNIAITQFFGYRFTEKDLIHKFVSSWWSEYLDARPEHVR
KYPSSYSG SEQ ID 72 - >gi|83016748|dbj|BAE53441.1|DsRed [synthetic construct]
MKLASSENVITEFMRFKVRMEGTVNGHEFEIEGEGEGRPYEGHNTVKLKVTKGGPL
PFAWDILSPQFQYGSKVYVKHPADIPDYKKLSFPEGFKWERVMNFEDGGVATVTQD
SSLQDGCFIYKVKFIGVNFPSDGPVMQKKTMGWEASTERLYPRDGVLKGETHKALK
LKDGGHYLVEFKSIYMAKKPVQLPGYYYVDAKLDITSHNEDYTIVEQYERTEGRHH
LFLRSRAPPPPLT SEQ ID 73 - >gi|18389895|gb|AAL68784.1|AF457554_ 1 salivary gland 1-like 3 protein [Anopheles gambiae]
MAGQRHLIEQAWQYGAQLQHELMLTSMESDRVQRALVLHSMLVNASLAEMVKES
YQTHGADGRMVVRMLKFVRLLPGADERVAVYKQLAELLKSNGQDGRFPPAVIFSTD
VRQLEDRYKPDHAQYEGKVVERWLAELQAGTFHEVVEFARDYPEYFARVEEPLYE -continued
TLKQQWSAEGLDRMVSFPNALPVGVQRVRALRALLETLLQHQGEQNNDVYLIRLA
HETGRVEATVGQADAAVRQALDDVKKLFEQFKYQRGFPDYEALYKLFKGL SEQ ID 74 - >gi|18389891|gb|AAL68782.1|AF457552_ 1 D7 protein long form [Anopheles
gambiae]
MIVPRVLLFILLELFVQATQAFKALDPEEAWYVYERCHEDHLPSGPNRETYLKTWKF
WKLEPNDAVTHCYVKCTLAGLQMYDEKTNTFKPETVPVQHEAYKSFTEVESSKVN
ELQQALSSLNAGSGSCAEVFNAYLPVHNKYIGVSRKIYHGTVDSVAKIYEAKPEIKK
QEESFFAYCAKKALGANGKEGYKKIRDYELADSAEFRNAMDCVFRGFRYMDDSGL
KVDEVVRDFNLINKSDLEPEVRSVLASCTGTHAYDYYSCLLNSSVKEDFRNAFYFHE
LRSANYGYLAMGKVYEGPEKVKEELKKLNY SEQ ID 75 - >emb|CAC35527.1|gSG9 protein [Anopheles gambiae]
MCKFYRLISTLLVVVVIAPRHQCSPFFFQYNRPYLSQPSSQLASTAANVVQRSNVTVA
LGNRINTDTALDDYGTRV SEQ ID 76 - >sp|Q9U9L1|RS17_ ANOGA 40S ribosomal protein S17
MGRVRTKTIKKASKVIIEKYYTRLTMDFDTNKRIVEEVAIIPTKPLRNKIAGFVTHLM
KRLRHSQVRGISIKLQEEERERRDNYVPDVSALEQDIIEVDPETKEMLKHLDFNNIVV
QLTNPTAPGYSNRRN SEQ ID 77 - >emb|CAC35523.1|gSG7 protein [Anopheles gambiae]
MHAKPAFVLIALGVICLLQTTPTSASTNHVQQLMKVFRSMTQNFDYTKKPSYLQRA
KYGVQNQLRNPLVQKAGNLPKSAKLSDGCLKQMVARVTDLEASFYASFSYNCHDH
DQYSMECLEAAEPKYLDGLKTLADETAQCMRDQQ SEQ ID 78 - >gb|AAD47075.1|AF164151_ 1 translation initiation factor 4C (1A) [Anopheles
gambiae]
MPKNKGKGGKNRRRGKNENESEKRELIFKEDEQEYAQVTKMLGNGRLEAMCFDGV
KRLCHIRGKLRKKVWINQGDIILIGLRDYQDSKADVILKYTPDEARNLKTYGEFPESV
RTNETVTFVENDMDDDIEFGDDYSSSEEGDAIDAI SEQ ID 79 - >emb|CAC35519.1|gSG2-like protein [Anopheles gambiae]
MKLFLTLLSTLSVAMVFALPAHHHSRGGDGSSANSTGNSDNNSAGVPDFGFNSQSN
VPGFGNGQQPGQQQGQQGQGFPFFGQGQSGFPSFGNRLQPFFGQNQQGQDGDAQ
QGRGVPFFGQGGGQGGIPSFGSGQQNGGVPFLGNGQGQSGFPSFGNGQQGGNFPFFG SEQ ID 80 - >emb|CAC35451.1|hypothetical protein [Anopheles gambiae]
MKLYAFALVLCVGLAVGAEVDSVPEVPSDLQQQLDELQLADKPEAPVDDAEQPLPP
NGDELPEDAPEPVPEDGSPDEEHLEEEQEEEAEADEEEADESESEESEESDELEEARL
VAEELEERQQELDYLKRYLVGRLQAVAILDRRVRPAVIRRPWIRRPWIRRPG SEQ ID 81 >emb|CAC35524.1|D7r4 protein [Anopheles gambiae]
MIRQVIISYFLTVCLLALVQSETVQDCENKLPPSLKSRLCEIRRYEIIEGPEMDKHIHCV
MRALDFVYEDGRGDYHKLYDPLNIIELDKRHDVNLEKCIGECVQVPTSERAHVFYK
CLLKSTTGRTFKKVFDLMELKKAGKVPQHQRYTAEFVQIMKDYDKALNC SEQ ID 82 - >ref|XP_ 001230998.1|ENSANGP00000014906 [Anopheles gambiae str.
PEST]
MEAISEALQPYKEQVGMAAGILTVGQMFSGCFVCNDIRKKGTTDGFSAMPFVGGCG
LTVLFLQHGMLMNDSAMTNANLVGLTISLAYAIFFLLYTPPTGRSSYWRQVGGTALF
TITLLGYVKVENPSVVEDRFGMIITVLMLALIGQPLFGLPDIIRRKSTEGLPFAMILSGT
IVGLSWLLYGVILNNVFVVCQNLAAVTLSGIQLALFAIYPSKAAPPSKKRE SEQ ID 83 - >ref|XP_ 316361.2|ENSANGP00000012984 [Anopheles gambiae str. PEST]
MESIAVALQPYKDTVGLTAAIVTVVQFFSGVLALNAIRRQGNTRGFSALPFLGGTVF
CLLNIQFGQMLRDDGMIRVNFIGLALNLLYVCGFYLYTEGPAKTAVWGQIGLAGAL
TAGVLSYVQYEDPQLVEFRFGLILTGLLWTLVGMPLLGLGDILKKKSTEGLPFPIIFLG
AVVSFAWLLYGIILRSNFLVVQNLMALALSAVQLSLFIIFPSGAAKPPPTPAKKRN SEQ ID 84 - >ref|XP_ 314140.3|ENSANGP00000015780 [Anopheles gambiae str. PEST]
MDGIMSKGSLASLATVATVLQFLTGTVICNRYIRKKSTGDTSAFPFISGFLSCFMWLK
YGVLTEESTLILVNFIGSALFFSYTVVFFIFCVNKREVIRQMMVISCIILSATLYTLFETD
DEKSIRVIGLLCCCLAVLFFASPLTMLAHVIRTQNTDSLPFPIIMASFFVCLLWTAYGV
LIGDRFIQIPNLLGGILAGIQLTLYVIYPKKKASFSGGPRYSPLVSENPIL SEQ ID 85 - >emb|CAC35522.1|gSG6 protein [Anopheles gambiae]
MAIRVELLLAMVLLPLLLLESVVPYAAAEKVWVDRDKVYCGHLDCTRVATFKGER
FCTLCDTRHFCECKETREPLPYMYACPGTEPCQSSDRLGSCSKSMHDVLCDRIDQAF
LEQ The peptides of the present invention, such as those of SEQ ID 1-44 and those within SEQ ID 131-134 described above preferably comprise one or more further amino acids at one or both of their termini in order to aid in their processing into vaccines. Typically, these further amino acids are the ones adjacent to each of the termini of SEQ ID 1-44, as shown in the larger proteins of SEQ ID 45-85 above (these larger proteins contain the sequences of SEQ ID 1-44). Preferably the number of further amino acids at each terminus is from 1-5, more preferably from 1-3, and most preferably 2 at each terminus. In each of these cases, if there are less than two further amino acids at that terminus of the sequences of SEQ ID 1-44, then the further amino acids include all of the remaining amino acid(s) at that terminus Particularly preferred sequences of this type, corresponding to SEQ ID 1-44, are as follows:

```
SEQ ID 86    MHLTLFTVAVLLLAAAALLLLLPPAYSTTLTPPAP
SEQ ID 87    MPLSYCHLFLTHTLARALSFSRSDCLKF
SEQ ID 88    MKNVFFALLLVVLVCCLVSVQGNEIIQ
SEQ ID 89    GIKLLVLLICLFFYHTHCTTAYLWLAMGVEA
SEQ ID 90    MFLKGSFPRFQMCVMLIGFFSSAKCLMC
SEQ ID 91    KQNDYQALLGLCCPWIDLAAADLPMRRHAKARE
SEQ ID 92    MKFYSVGKLVKVLLVMAVCCLLLCTAPTGADPLPG
SEQ ID 93    MKFAFAFVLIALFAVFAVSQALPQPEQAAASS
SEQ ID 94    SNDGASAITKIVLELTPEQAAAVQK
SEQ ID 95    AITLFIFLVCCQIPLFGIMSSDSADPFYWIRVILASN
SEQ ID 96    MGRVMCLLRLMSTLLVVLSIVGKKT
SEQ ID 97    MKLYSGYRLLVLLVMTVCCLLLFIAPTGADPLPGQTQRTLGY
SEQ ID 98    CKMYCVIKGKTGGYCNSEGLCTCRAEDLHFLLKPIINKD
SEQ ID 99    TVNAEDPRTELIGCGSVLFHLAANRLSLQLEEFAVCKRSN
SEQ ID 100   CVALIGLLLCSVQSVTANDPVDALGACSGNLFGLLMTRLQQ
SEQ ID 101   MASKLFVLAFLCLALVVVVQSAPQYARGDVPTYD
SEQ ID 102   MKSMLVAFATLSVALVVVVAIPANFNYGGGGGYFINGTGQSF
SEQ ID 103   NAIYEKLPAYLSEVSARVNVLQVSLQHDLPNLQE
SEQ ID 104   STEMKLAKVALVTISLWFMAWTPYLVINFTGIFK
SEQ ID 105   GDLLPAKVIPDKTAAYVAYGGQETLVEHVEVLVHK
SEQ ID 106   NTFYTCFLGTSSLAGFKNAVDYDELLKAGKM
SEQ ID 107   QCVLEVLGFVEDNGELVFQELLGVLKMVDPDGDHA
SEQ ID 108   RRKLTPTVVVVLLCLTFVADALTIQELRAQIAQQRIQQRYGVTVATTSA
SEQ ID 109   CSSLSDYGLIELKEHCLECCQKDTEADSKLKVYPAAVLEVCT
SEQ ID 110   AITYICFILHGVSEIIPQQQKKTMKFLLLVASVLCLVLIVS
SEQ ID 111   EWRYFVVIALICPLIIVETLAVSD
SEQ ID 112   QLLLLYLDAADLRRALHQYQLLAAQGDRHLPQQIVKFVYA
SEQ ID 113   RKVLLTPALQAYIMDEHNLRSNIALGRIRPYPSAVKMPTL
SEQ ID 114   DGVLKGETHKALKLKDGGHYLVEFKSIYMAK
SEQ ID 115   ALVLHSMLVNASLAEMVKESYQTHGADGRMVVRMLKFVRLLPGA
SEQ ID 116   VQRVRALRALLETLLQHQGEQNNDVYLIRLAHETGR
SEQ ID 117   VNELQQALSSLNAGSGSCAEVFNAYLPVHNKYIGVSRKIYH
SEQ ID 118   MCKFYRLISTLLVVVVIAPRHQCSPFFFQYNRPYLSQ
SEQ ID 119   RDNYVPDVSALEQDIIEVDPETKEMLKHLDFNNIVVQLTN
SEQ ID 120   HDQYSMECLEAAEPKYLDGLKTLADETAQCMR
SEQ ID 121   EQEYAQVTKMLGNGRLEAMCFDGVKRLCHIRGKLRK
SEQ ID 122   MKLFLTLLSTLSVAMVFALPAHHHSRGGD
SEQ ID 123   SDELEEARLVAEELEERQQELDYLKRYLVGRLQAVAI
SEQ ID 124   IISYFLTVCLLALVQSETVQDCE
SEQ ID 125   DSAMTNANLVGLTISLAYAIFFLLYTPPTGRSSYW
SEQ ID 126   VVSFAWLLYGIILRSNFLVVQNLMALALSAVQLSLFIIFP
```

SEQ ID 127    TSAFPFISGFLSCFMWLKYGVLTEESTLILVNFIGSALFF

SEQ ID 128    VIGLLCCCLAVLFFASPLTMLAHVIRTQ

SEQ ID 129    VELLLAMVLLPLLLLESVVPYAAAEKVWVD

Particularly preferred such peptides also include the following:

residues 1-35 of >gi|18389913|gb|AAL68793.1|AF457563_1 hypothetical protein 16 [*Anopheles gambiae*]

residues 1-28 of >gi|18389909|gb|AAL68791.1|AF457561_1 hypothetical protein 14 [*Anopheles gambiae*]

residues 1-27 of >gi|18389907|gb|AAL68790.1|AF457560_1 hypothetical protein 13 [*Anopheles gambiae*]

residues 8-38 of >gi|18389903|gb|AAL68788.1|AF457558_1 hypothetical protein 11 [*Anopheles gambiae*]

residues 1-28 of >gi|62546227|gb|AAX86005.1|hyp3.5 precursor [*Anopheles gambiae*]

residues 12-44 of gi|18389899|gb|AAL68786.1|AF457556_1 salivary gland 7-like protein [*Anopheles gambiae*]

residues 1-35 of >gi|18389911|gb|AAL68792.1|AF457562_1 hypothetical protein 15 [*Anopheles gambiae*]

residues 1-32 of >gi|62546225|gb|AAX86004.1|hyp6.3 precursor [*Anopheles gambiae*]

residues 32-56 of >gi|62546225|gb|AAX86004.1|hyp6.3 precursor [*Anopheles gambiae*]

residues 36-72 of >gi|17026153|emb|CAD12038.1|Sec61 protein [*Anopheles gambiae*]

residues 1-25 of >gi|62546223|gb|AAX86003.1|hyp6.2 precursor [*Anopheles gambiae*]

residues 15-56 of >gi|18389915|gb|AAL68794.1|AF457564_1 hypothetical protein 17 [*Anopheles gambiae*]

residues 55-93 of >gi|87080391|gb|ABD18596.1|defensin [*Anopheles gambiae*]

residues 20-59 of >gi|18389901|gb|AAL68787.1|AF457557_1 hypothetical protein 10 [*Anopheles gambiae*]

residues 5-45 of >gi|18389905|gb|AAL68789.1|AF457559_1 hypothetical protein 12 [*Anopheles gambiae*]

residues 1-34 of >gi|4127344|emb|CAA76832.1| cE5 protein [*Anopheles gambiae*]

residues 1-42 of >gi|4210617|emb|CAA10259.1| SG2 protein [*Anopheles gambiae*]

residues 89-122 of >gi|4127309|emb|CAA76820.1| hypothetical protein [*Anopheles gambiae*]

residues 63-96 of >gi|4375824|emb|CAA76825.1| opsin [*Anopheles gambiae*]

residues 39-73 of >gi|62546233|gb|AAX86008.1| unknown [*Anopheles gambiae*]

residues 115-145 of >gi|3378531|emb|CAA03872.1|D7r2 protein [*Anopheles gambiae*]

residues 61-95 of >gi|3378529|emb|CAA03871.1|D7r3 protein [*Anopheles gambiae*]

residues 21-69 of >gi|18389893|gb|AAL68783.1|AF457553_1 mucin-like protein [*Anopheles gambiae*]

residues 41-82 of >gi|18389881|gb|AAL68777.1|AF457547_1 selenoprotein [*Anopheles gambiae*]

residues 4-44 of >gi|18389879|gb|AAL68776.1|AF457546_1 30 kDa protein [*Anopheles gambiae*]

residues 2-25 of >gi|18378603|gb|AAL68639.1|AF458073_1 D7-related 5 protein [*Anopheles gambiae*]

residues 18-57 of >gi|18389897|gb|AAL68785.1|AF457555_1 salivary gland 1-like 4 protein [*Anopheles gambiae*]

residues 57-97 of >gi|18389883|gb|AAL68778.1|AF457548_1 antigen 5-related 1 protein [*Anopheles gambiae*]

residues 156-186 of >gi|83016748|dbj|BAE53441.1| DsRed [synthetic construct]

residues 35-78 of >gi|18389895|gb|AAL68784.1|AF457554_1 salivary gland 1-like 3 protein [*Anopheles gambiae*]

residues 189-224 of >gi|18389895|gb|AAL68784.1|AF457554_1 salivary gland 1-like 3 protein [*Anopheles gambiae*]

residues 111-151 of >gi|18389891|gb|AAL68782.1|AF457552_1 D7 protein long form [*Anopheles gambiae*]

residues 1-37 of >emb|CAC35527.1| gSG9 protein [*Anopheles gambiae*]

residues 81-120 of >sp|Q9U9L1|RS17_ANOGA 40S ribosomal protein S17 residues 111 to 142 of >emb|CAC35523.1| gSG7 protein [*Anopheles gambiae*]

residues 32-67 of >gb|AAD47075.1|AF164151_1 translation initiation factor 4C (1A) [*Anopheles gambiae*]

residues 1-29 of >emb|CAC35519.1| gSG2-like protein [*Anopheles gambiae*]

residues 106-142 of >emb|CAC35451.1| hypothetical protein [*Anopheles gambiae*]

residues 6-28 of >emb|CAC35524.1| D7r4 protein [*Anopheles gambiae*]

residues 70-104 of >ref|XP_001230998.1| ENSANGP00000014906 [*Anopheles gambiae* str. PEST]

residues 174-213 of >ref|XP_316361.2| ENSANGP00000012984 [*Anopheles gambiae* str. PEST]

residues 41-80 of >ref|XP_314140.3| ENSANGP00000015780 [*Anopheles gambiae* str. PEST]

residues 126-153 of >ref|XP_314140.3| ENSANGP00000015780 [*Anopheles gambiae* str. PEST]

residues 5-34 of >emb|CAC35522.1| gSG6 protein [*Anopheles gambiae*]

In alternative embodiments of the present invention, the invention is directed to compositions comprising polypeptides which are homologous to those described above, in particular peptides that are homologous to any of SEQ ID 1-134. The homology referred to above in respect of these sequences is preferably 60%, 75%, 80%, 85%, 90%, 95% or substantially 100%.

The percent homology of a first polypeptide sequence to a second polypeptide sequence, as referred to in the context of the present invention, is defined as the number of amino acid residues in the second sequence that match in both position and identity to those in the first sequence, divided by the total number of amino acid residues in the second polypeptide (both first and second polypeptides must have the same number of amino acid residues) and multiplied by 100. In the present invention, it is preferred that the polypeptide homology to the defined sequences is 75% or more, 80% or more, 85% or more, 90% or more, 95% or more or 100% (or substantially 100%).

In the present invention, the arthropod borne disease is not especially limited, and the polypeptides may be immunogenic against, and/or derived from, any known arthropod borne disease. Examples of diseases, pathogens and vectors covered by the present invention, are set out in Table 1 above. Preferably, however, the relevant disease is malaria (including any malaria strain), as caused by any one of the strains of Plasmodium.

The specific sequences homologous to any of SEQ ID 1-134 described above are preferably the ones at the appropriate positions within known arthropod proteins, which can be found at the public NCBI protein database, which may be accessed online at the following URL address http://www.ncbi.nlm.nih.gov/entrez/query/static/help/helpdoc.html#Protein. The list is typically in the form |version number (gi number)|database identification (e.g. gb for GenBank)|NCBI accession number|optional further information (e.g. the accession number of the nucleotide sequence from which the protein sequence is derived). The sequences The protein database contains sequence data from the translated coding regions from DNA sequences in GenBank, EMBL, and DDBJ as well as protein sequences submitted to Protein Information Resource (PIR), SWISS-PROT, Protein Research Foundation (PRF), and Protein Data Bank (PDB) (sequences from solved structures).

The epitopes within the sequences defined above are not especially limited, provided that they contain 7 amino acid residues or more. Preferably the epitopes are at least of a length that is appropriate for the smaller immunogenic epitopes, such as CTL, T helper and B cell epitopes in a particular vertebrate species, such as in a human. Typically the epitopes contain 8, 9, 10, or 11 amino acid residues, but may contain more if desired.

Although it may comprise more amino acids typically, the polypeptide comprises 100 amino acids or less, preferably between 7 and 100 amino acids, and more preferably from 8-75 amino acids. The size should not be so great that useful epitopes suffer from competition with non-protective epitopes in the immune system (for this reason full proteins are not included), nor should the size be so small that only a very narrow range of protection is offered. More preferred ranges are from 15-75 amino acids, 20-55 amino acids and 23-50 amino acids. It is particularly preferred that the polypeptide consists of (or substantially consists of) a sequence selected from the sequences defined above.

In addition to the polypeptides described above, the invention also provides multi-epitope immunogenic polypeptides comprising two or more polypeptides of the present invention either as multi-branched polypeptides or concatenated sequences. These multi-epitope polypeptides are not limited in size and may comprise e.g. up to 1400, or up to 900, or up to 550 amino acids. Thus, they extend not only to the polypeptides outlined above, but also to larger polypeptides, provided that these larger polypeptides comprise two or more units, each unit consisting of a polypeptide of the invention. Thus, a polypeptide having 100 repeating units of a 7-mer according to the present invention is encompassed by the present invention, as is a polypeptide having, say 52 units of one 8-mer epitope, and 23 units of a second 10-mer epitope. Polypeptides of this type will not suffer from the competition problems associated with similar length polypeptides that comprise only one or two epitopes. For the avoidance of doubt, the multi-epitope polypeptide may comprise multiple copies of the same epitope, or single copies of a plurality of different epitopes, or multiple copies of 2 or more epitopes. It is particularly preferred that a multi-epitope polypeptide comprises two or more of the sequences described above in SEQ ID 1-44 (and especially those in SEQ ID 1-6, 7, 8, 11, 12, 15, 16, 20, 26, 28, 30-32, 35, 41, and 42) or in SEQ ID 86-134.

As has been mentioned, the invention provides a polypeptide composition comprising one or more, preferably two or more different polypeptides as defined above. Thus, the polypeptide composition may comprise any number of polypeptides of the present invention together in the same sequence, mixture or formulation. The presence of a plurality of polypeptides together is useful since each may elicit its own immune response, widening the protective effect of the composition. It is particularly preferred that the composition contains two or more of (or all of) the sequences of SEQ ID 1-44 (and especially those in SEQ ID 1-6, 7, 8, 11, 12, 15, 16, 20, 26, 28, 30-32, 35, 41, and 42), and/or two or more of the epitopes within SEQ ID 86-134. In the composition each sequence and/or epitope may be present either as a separate peptide, or as a number of larger peptides comprising several concatenated epitopes and/or sequences (e.g. three sequences concatenated in one larger peptide and another 4 in another larger peptide, etc.).

The invention also provides a polypeptide construct, which construct comprises a polypeptide as defined above and a carrier. The construct may be formed by combining one or more epitopes and/or polypeptides as defined above with the carrier. The carrier may be a molecule, such as an adjuvant and/or an excipient. Combining in this context means either mixing together, or attaching together (e.g. via a covalent linkage).

The present invention further provides a polypeptide as defined above for use in medicine. Also provided is a medicament or vaccine composition against arthropod borne diseases, comprising a polypeptide as defined above, and one or more appropriate excipients and/or adjuvants, or a polypeptide construct as defined above and optionally one or more appropriate excipients and/or adjuvants (if the carrier part of the construct is itself an excipient or adjuvant, then a further excipient or adjuvant may not be needed). The excipient or adjuvant is not especially limited, and any excipients or adjuvants used in medicaments and vaccines may be employed. The medicament or vaccine composition may be produced according to any known method appropriately adapted to the present invention, such as by mixing a polypeptide of the invention with an appropriate excipient.

A method of producing a polypeptide as defined above is also provided by the invention. The method is not especially limited, and typically comprises joining two or more epitopes to form the polypeptide. The polypeptide may, however, be synthesised by direct chemical synthesis (e.g. incorporating one amino acid at a time until the full polypeptide is formed) or by recombinant methods. Such general methods are well known to the skilled person and may be adapted to the present invention as desired. In some instances, the polypeptide of the present invention may comprise additional amino acid sequences at one or both termini to help in synthesis of the polypeptide. These additional sequences are preferably from 1-5 amino acids in length. Typically 2 amino acids are involved. Examples of such sequences are provided as SEQ ID 86-129, as described above.

The invention still further provides use of a polypeptide or composition as defined above, in the manufacture of a medicament or vaccine, effective in the treatment or prevention of an arthropod borne disease. Also provided is a method of treating or preventing an arthropod borne disease, which method comprises administering a polypeptide, a composition, a medicament or a vaccine as defined above to a vertebrate. The method of administration is not especially limited, and may comprise subcutaneous, intramuscular, intravenous, intra-dermal, or intra-nasal administration, or may be administered orally (e.g. in the form of a pill or a liquid preparation), or may be in the form of a suppository, if desired. The form of such administration preparations is not especially limited, and known forms may be employed with appropriate modifications that will be apparent to the skilled person. The dosage is not especially limited and may range from 1 pg to 100 g, preferably 1 ng to 100 g of the polypeptide per individual, depending upon the size, weight and species of the individual involved.

The invention may be applied to any vertebrate, since the immune systems of vertebrates operate in a related manner. Typically, the vertebrate referred to in the present context is a mammal, bird, a reptile or a fish. It is especially preferred that the vertebrate is a human, a domestic animal (such as a dog or a cat), a farm animal (such as a pig or a horse), a bovine animal (such as cattle), or fowl (such as a domestic bird, a farm bird, or a game bird). When the vertebrate is a bird, it is preferably a chicken, a turkey, a duck, or a goose.

Examples of human MHCs (HLAs) that may be associated with a particular T cell epitope in the present invention include the following:

HLA-A

A*010101, A*010102, A*010103, A*0102, A*0103, A*0104N, A*0106, A*0107, A*0108, A*0109, A*0110, A*02010101, A*02010102L, A*020102, A*020103, A*020104, A*020105, A*020106, A*020107, A*020108, A*020109, A*020110, A*020111, A*0202, A*020301, A*020302, A*0204, A*0205, A*020601, A*020602, A*020603, A*0207, A*0208, A*0209, A*0210, A*0211, A*0212, A*0213, A*0214, A*0215N, A*0216, A*021701, A*021702, A*0218, A*0219, A*022001, A*022002, A*0221, A*0222, A*0224, A*0225, A*0226, A*0227, A*0228, A*0229, A*0230, A*0231, A*0232N, A*0233, A*0234, A*023501, A*023502, A*0236, A*0237, A*0238, A*0239, A*0240, A*0241, A*0242, A*0243N, A*0244, A*0245, A*0246, A*0247, A*0248, A*0249, A*0250, A*0251, A*0252, A*0253N, A*0254, A*0255, A*0256, A*0257, A*0258, A*0259, A*0260, A*0261, A*0262, A*0263, A*0264, A*0265, A*0266, A*0267, A*0268, A*0269, A*0270, A*0271, A*0272, A*0273, A*03010101, A*03010102N, A*03010103, A*030102, A*030103, A*0302, A*0303N, A*0304, A*0305, A*0306, A*0307, A*0308, A*0309, A*0310, A*0311N, A*0312, A*0313, A*0314, A*110101, A*110102, A*1102, A*1103, A*1104, A*1105, A*1106, A*1107, A*1108, A*1109, A*1110, A*1111, A*1112, A*1113, A*1114, A*1115, A*1116, A*1117, A*1118, A*1119, A*2301, A*2302, A*2303, A*2304, A*2305, A*2306, A*2307, A*2308N, A*2309, A*2310, A*2311N, A*2312, A*24020101, A*24020102L, A*240202, A*240203, A*240204, A*240205, A*240206, A*240301, A*240302, A*2404, A*2405, A*2406, A*2407, A*2408, A*2409N, A*2410, A*2411N, A*2413, A*2414, A*2415, A*2417, A*2418, A*2419, A*2420, A*2421, A*2422, A*2423, A*2424, A*2425, A*2426, A*2427, A*2428, A*2429, A*2430, A*2431, A*2432, A*2433, A*2434, A*2435, A*2436N, A*2437, A*2438, A*2439, A*2440N, A*2441, A*2442, A*2443, A*2444, A*2445N, A*2446, A*250101, A*250102, A*2502, A*2503, A*2504, A*2601, A*2602, A*2603, A*2604, A*2605, A*2606, A*260701, A*260702, A*2608, A*2609, A*2610, A*2611N, A*2612, A*2613, A*2614, A*2615, A*2616, A*2617, A*2618, A*2619, A*2620, A*2621, A*2622, A*2623, A*29010101, A*29010102N, A*290201, A*290202, A*290203, A*2903, A*2904, A*2905, A*2906, A*2907, A*2908N, A*2909, A*2910, A*2911, A*300101, A*300102, A*300201, A*300202, A*3003, A*3004, A*3006, A*3007, A*3008, A*3009, A*3010, A*3011, A*3012, A*310102, A*3102, A*3103, A*3104, A*3105, A*3106, A*3107, A*3108, A*3109, A*3110, A*3201, A*3202, A*3203, A*3204, A*3205, A*3206, A*3207, A*3208, A*3301, A*330301, A*330302, A*3304, A*3305, A*3306, A*3307, A*3401, A*3402, A*3403, A*3404, A*3405, A*3406, A*3601, A*3602, A*3603, A*3604, A*4301, A*6601, A*6602, A*6603, A*6604, A*680101, A*680102, A*680103, A*6802, A*680301, A*680302, A*6804, A*6805, A*6806, A*6807, A*6808, A*6809, A*6810, A*6811N, A*6812, A*6813, A*6814, A*6815, A*6816, A*6817, A*6818N, A*6819, A*6820, A*6821, A*6822, A*6823, A*6824, A*6825, A*6826, A*6827, A*6901, A*7401, A*7402, A*7403, A*7404, A*7405, A*7406, A*7407, A*7408, A*7409, A*7410, A*8001.

HLA-B

B*070201, B*070202, B*070203, B*070204, B*0703, B*0704, B*0705, B*0706, B*0707, B*0708, B*0709, B*0710, B*0711, B*0712, B*0713, B*0714, B*0715, B*0716, B*0717, B*0718, B*0719, B*0720, B*0721, B*0722, B*0723, B*0724, B*0725, B*0726, B*0727, B*0728, B*0729, B*0730, B*0731, B*0732, B*0733, B*0734, B*0735, B*0736, B*0737, B*0738, B*0801, B*0802, B*0803, B*0804, B*0805, B*0806, B*0807, B*0808N, B*0809, B*0810, B*0811, B*0812, B*0813, B*0814, B*0815, B*0816, B*0817, B*0818, B*0819N, B*0820, B*0821, B*0822, B*1301, B*1302, B*1303, B*1304, B*1306, B*1307N, B*1308, B*1309, B*1310, B*1311, B*1312, B*1313, B*1401, B*1402, B*1403, B*1404, B*1405, B*140601, B*140602, B*15010101, B*15010102N, B*150102, B*150103, B*150104, B*150105, B*1502, B*1503, B*1504, B*1505, B*1506, B*1507, B*1508, B*1509, B*1510, B*151101, B*151102, B*1512, B*1513, B*1514, B*1515, B*1516, B*15170101, B*15170102, B*1518, B*1519, B*1520, B*1521, B*1523, B*1524, B*1525, B*1526N, B*1527, B*1528, B*1529, B*1530, B*1531, B*1532, B*1533, B*1534, B*1535, B*1536, B*1537, B*1538, B*1539, B*1540, B*1542, B*1543, B*1544, B*1545, B*1546, B*1547, B*1548, B*1549, B*1550, B*1551, B*1552, B*1553, B*1554, B*1555, B*1556, B*1557, B*1558, B*1560, B*1561, B*1562, B*1563, B*1564, B*1565, B*1566, B*1567, B*1568, B*1569, B*1570, B*1571, B*1572, B*1573, B*1574, B*1575, B*1576, B*1577, B*1578, B*1579N, B*1580, B*1581, B*1582, B*1583, B*1584, B*1585, B*1586, B*1587, B*1588, B*1589, B*1590, B*1591, B*1592, B*1593, B*1594N, B*180101, B*180102, B*1802, B*1803, B*1804, B*1805, B*1806, B*1807, B*1808, B*1809, B*1810, B*1811, B*1812, B*1813, B*1814, B*1815, B*1817N, B*1818, B*1819, B*1820, B*2701, B*2702, B*2703, B*2704, B*270502, B*270503, B*270504, B*270505, B*270506, B*270507, B*2706,

B*2707, B*2708, B*2709, B*2710, B*2711, B*2712, B*2713, B*2714, B*2715, B*2716, B*2717, B*2718, B*2719, B*2720, B*2721, B*2723, B*2724, B*2725, B*2726, B*350101B*350102, B*3502, B*3503, B*3504, B*3505, B*3506, B*3507, B*3508, B*350901, B*350902, B*3510, B*3511, B*3512, B*3513, B*351401, B*351402, B*3515, B*3516, B*3517, B*3518, B*3519, B*3520, B*3521, B*3522, B*3523, B*3524, B*3525, B*3526, B*3527, B*3528, B*3529, B*3530, B*3531, B*3532, B*3533, B*3534, B*3535, B*3536, B*3537, B*3538, B*3539, B*3540N, B*3541, B*3542, B*3543, B*3544, B*3545, B*3546, B*3547, B*3548, B*3549, B*3550, B*3551, B*3552, B*3553N, B*3701, B*3702, B*3703N, B*3704, B*3705, B*3706, B*3707, B*3801, B*380201, B*380202, B*3803, B*3804, B*3805, B*3806, B*3807, B*3808, B*3809, B*3810, B*390101, B*390103, B*390104, B*390201, B*390202, B*3903, B*3904, B*3905, B*390601, B*390602, B*3907, B*3908, B*3909, B*3910, B*3911, B*3912, B*3913, B*3914, B*3915, B*3916, B*3917, B*3918, B*3919, B*3920, B*3922, B*3923, B*3924, B*3925N, B*3926, B*3927, B*3928, B*3929, B*3930, B*3931, B*3932, B*400101, B*400102, B*400103, B*400104, B*400105, B*400201, B*400202, B*4003, B*4004, B*4005, B*40060101, B*40060102, B*4007, B*4008, B*4009, B*4010, B*4011, B*4012, B*4013, B*401401, B*401402, B*401403, B*4015, B*4016, B*4018, B*4019, B*4020, B*4021, B*4022N, B*4023, B*4024, B*4025, B*4026, B*4027, B*4028, B*4029, B*4030, B*4031, B*4032, B*4033, B*4034, B*4035, B*4036, B*4037, B*4038, B*4039, B*4040, B*4042, B*4043, B*4044, B*4045, B*4046, B*4047, B*4048, B*4049, B*4050, B*4051, B*4052, B*4053, B*4054, B*4055, B*4056, B*4057, B*4101, B*4102, B*4103, B*4104, B*4105, B*4106, B*4201, B*4202, B*4204, B*420501, B*420502, B*4206, B*44020101, B*44020102S, B*440202, B*440203, B*440301, B*440302, B*4404, B*4405, B*4406, B*4407, B*4408, B*4409, B*4410, B*4411, B*4412, B*4413, B*4414, B*4415, B*4416, B*4417, B*4418, B*4419N, B*4420, B*4421, B*4422, B*4423N, B*4424, B*4425, B*4426, B*4427, B*4428, B*4429, B*4430, B*4431, B*4432, B*4433, B*4434, B*4435, B*4436, B*4437, B*4438, B*4439, B*4440, B*4501, B*4502, B*4503, B*4504, B*4505, B*4506, B*4507, B*4601, B*4602, B*4603, B*4604, B*47010101, B*47010102, B*4702, B*4703, B*4704, B*4705, B*4801, B*4802, B*4803, B*4804, B*4805, B*4806, B*4807, B*4808, B*4809, B*4810, B*4901, B*4902, B*4903, B*5001, B*5002, B*5004, B*510101, B*510102, B*510103, B*510104, B*510105, B*510201, B*510202, B*5103, B*5104, B*5105, B*5106, B*5107, B*5108, B*5109, B*5110, B*5111N, B*5112, B*511301, B*511302, B*5114, B*5115, B*5116, B*5117, B*5118, B*5119, B*5120, B*5121, B*5122, B*5123, B*5124, B*5126, B*5127N, B*5128, B*5129, B*5130, B*5131, B*5132, B*5133, B*5134, B*5135, B*5136, B*520101, B*520102, B*520103, B*520104, B*5202, B*5203, B*5204, B*5205, B*5206, B*530101, B*530102, B*5302, B*5303, B*5304, B*5305, B*5306, B*5307, B*5308, B*5309, B*5401, B*5402, B*5501, B*5502, B*5503, B*5504, B*5505, B*5507, B*5508, B*5509, B*5510, B*5511, B*5512, B*5513, B*5514, B*5515, B*5516, B*5601, B*5602, B*5603, B*5604, B*560501, B*560502, B*5606, B*5607, B*5608, B*5609, B*5610, B*5611, B*5612, B*5613, B*5614, B*570101, B*570102, B*5702, B*570301, B*570302, B*5704, B*5705, B*5706, B*5707, B*5708, B*5709, B*5801, B*5802, B*5804, B*5805, B*5806, B*5807, B*5808, B*5809, B*5810N, B*5901, B*670101, B*670102, B*6702, B*7301, B*7801, B*780201, B*780202, B*7803, B*7804, B*7805, B*8101, B*8102, B*8201, B*8202, B*8301.

HLA-C

Cw*010201, Cw*010202, Cw*0103, Cw*0104, Cw*0105, Cw*0106, Cw*0107, Cw*0108, Cw*0109, Cw*0110, Cw*020201, Cw*020202, Cw*020203, Cw*020204, Cw*020205, Cw*0203, Cw*0204, Cw*0205, Cw*0206, Cw*0207, Cw*0208, Cw*0209, Cw*030201, Cw*030202, Cw*030301, Cw*030302, Cw*030303, Cw*030304, Cw*030401, Cw*030402, Cw*030403, Cw*0305, Cw*0306, Cw*0307, Cw*0308, Cw*0309, Cw*0310, Cw*0311, Cw*0312, Cw*0313, Cw*0314, Cw*0315, Cw*0316, Cw*0317, Cw*0318, Cw*04010101, Cw*04010102, Cw*040102, Cw*0403, Cw*040401, Cw*040402, Cw*0405, Cw*0406, Cw*0407, Cw*0408, Cw*0409N, Cw*0410, Cw*0411, Cw*0412, Cw*0413, Cw*0414, Cw*0415, Cw*050101, Cw*050102, Cw*0502, Cw*0503, Cw*0504, Cw*0505, Cw*0506, Cw*0507N, Cw*0508, Cw*0509, Cw*0510, Cw*0602, Cw*0603, Cw*0604, Cw*0605, Cw*0606, Cw*0607, Cw*0608, Cw*0609, Cw*0610, Cw*0611, Cw*070101, Cw*070102, Cw*070103, Cw*07020101, Cw*07020102, Cw*07020103, Cw*0703, Cw*070401, Cw*070402, Cw*0705, Cw*0706, Cw*0707, Cw*0708, Cw*0709, Cw*0710, Cw*0711, Cw*0712, Cw*0713, Cw*0714, Cw*0715, Cw*0716, Cw*0717, Cw*0718, Cw*0719, Cw*0720, Cw*0721, Cw*0722, Cw*0723, Cw*0724, Cw*0725, Cw*0726, Cw*0727, Cw*0728, Cw*0729, Cw*080101, Cw*080102, Cw*0802, Cw*0803, Cw*0804, Cw*0805, Cw*0806, Cw*0807, Cw*0808, Cw*0809, Cw*0810, Cw*0811, Cw*0812, Cw*120201, Cw*120202, Cw*120203, Cw*120301, Cw*120302, Cw*120303, Cw*120401, Cw*120402, Cw*1205, Cw*1206, Cw*1207, Cw*1208, Cw*1209, Cw*1210, Cw*1211, Cw*1212, Cw*1213, Cw*1214, Cw*1215, Cw*140201, Cw*140202, Cw*140203, Cw*1403, Cw*1404, Cw*1405, Cw*150201, Cw*150202, Cw*1503, Cw*1504, Cw*150501, Cw*150502, Cw*150503, Cw*150504, Cw*1506, Cw*1507, Cw*1508, Cw*1509, Cw*1510, Cw*1511, Cw*1512, Cw*1601, Cw*1602, Cw*160401, Cw*1606, Cw*1701, Cw*1702, Cw*1703, Cw*1801, Cw*1802.

HLA-E

E*0101, E*010301, E*010302, E*010303, E*0104.

HLA-F

F*010101, F*010102.

HLA-G

G*010101, G*010102, G*010103, G*010104, G*010105, G*010106, G*010107, G*010108, G*0102, G*0103, G*010401, G*010402, G*010403, G*0105N, G*0106.

HLA-DRA

DRA*0101, DRA*010201, DRA*010202.

HLA-DRB1

DRB1*010101, DRB1*010102, DRB1*010103, DRB1*010201, DRB1*010202, DRB1*010203, DRB1*010204, DRB1*0103, DRB1*0104, DRB1*0105, DRB1*0106, DRB1*0107, DRB1*0108, DRB1*0109, DRB1*0110, DRB1*0111, DRB1*030101, DRB1*030102, DRB1*030201, DRB1*030202, DRB1*0303, DRB1*0304, DRB1*030501, DRB1*030502, DRB1*0306, DRB1*0307, DRB1*0308, DRB1*0309, DRB1*0310, DRB1*0311, DRB1*0312, DRB1*0313, DRB1*0314, DRB1*0315, DRB1*0316, DRB1*0317, DRB1*0318, DRB1*0319, DRB1*0320, DRB1*0321, DRB1*0322, DRB1*0323, DRB1*0324, DRB1*0325, DRB1*0326, DRB1*0327, DRB1*0328, DRB1*040101, DRB1*040102, DRB1*0402, DRB1*040301, DRB1*040302, DRB1*0404,

DRB1*040501, DRB1*040502, DRB1*040503, DRB1*040504, DRB1*0406, DRB1*040701, DRB1*040702, DRB1*040703, DRB1*0408, DRB1*0409, DRB1*0410, DRB1*0411, DRB1*0412, DRB1*0413, DRB1*0414, DRB1*0415, DRB1*0416, DRB1*0417, DRB1*0418, DRB1*0419, DRB1*0420, DRB1*0421, DRB1*0422, DRB1*0423, DRB1*0424, DRB1*0425, DRB1*0426, DRB1*0427, DRB1*0428, DRB1*0429, DRB1*0430, DRB1*0431, DRB1*0432, DRB1*0433, DRB1*0434, DRB1*0435, DRB1*0436, DRB1*0437, DRB1*0438, DRB1*0439, DRB1*0440, DRB1*0441, DRB1*0442, DRB1*0443, DRB1*0444, DRB1*0445, DRB1*0446, DRB1*0447, DRB1*0448, DRB1*0449, DRB1*0450, DRB1*070101, DRB1*070102, DRB1*0703, DRB1*0704, DRB1*0705, DRB1*0706, DRB1*0707, DRB1*0708, DRB1*080101, DRB1*080102, DRB1*080201, DRB1*080202, DRB1*080203, DRB1*080302, DRB1*080401, DRB1*080402, DRB1*080403, DRB1*080404, DRB1*0805, DRB1*0806, DRB1*0807, DRB1*0808, DRB1*0809, DRB1*0810, DRB1*0811, DRB1*0812, DRB1*0813, DRB1*0814, DRB1*0815, DRB1*0816, DRB1*0817, DRB1*0818, DRB1*0819, DRB1*0820, DRB1*0821, DRB1*0822, DRB1*0823, DRB1*0824, DRB1*0825, DRB1*0826, DRB1*0827, DRB1*0828, DRB1*0829, DRB1*090102, DRB1*090103, DRB1*0902, DRB1*0903, DRB1*100101, DRB1*100102, DRB1*110101, DRB1*110102, DRB1*110103, DRB1*110104, DRB1*110105, DRB1*1102, DRB1*1103, DRB1*110401, DRB1*110402, DRB1*1105, DRB1*110601, DRB1*110602, DRB1*1107, DRB1*110801, DRB1*110802, DRB1*1109, DRB1*1110, DRB1*1111, DRB1*111201, DRB1*111202, DRB1*1113, DRB1*1114, DRB1*1115, DRB1*1116, DRB1*1117, DRB1*1118, DRB1*1119, DRB1*1120, DRB1*1121, DRB1*1122, DRB1*1123, DRB1*1124, DRB1*1125, DRB1*1126, DRB1*112701, DRB1*112702, DRB1*1128, DRB1*1129, DRB1*1130, DRB1*1131, DRB1*1132, DRB1*1133, DRB1*1134, DRB1*1135, DRB1*1136, DRB1*1137, DRB1*1138, DRB1*1139, DRB1*1140, DRB1*1141, DRB1*1142, DRB1*1143, DRB1*1144, DRB1*1145, DRB1*1146, DRB1*1147, DRB1*1148, DRB1*1149, DRB1*1150, DRB1*1151, DRB1*1152, DRB1*1153, DRB1*1154, DRB1*120101, DRB1*120102, DRB1*120201, DRB1*120202, DRB1*120302, DRB1*1204, DRB1*1205, DRB1*1206, DRB1*1207, DRB1*1208, DRB1*1209, DRB1*1210, DRB1*130101, DRB1*130102, DRB1*130103, DRB1*130201, DRB1*130202, DRB1*130301, DRB1*130302, DRB1*1304, DRB1*1305, DRB1*1306, DRB1*130701, DRB1*130702, DRB1*1308, DRB1*1309, DRB1*1310, DRB1*1311, DRB1*1312, DRB1*1313, DRB1*131401, DRB1*131402, DRB1*1315, DRB1*1316, DRB1*1317, DRB1*1318, DRB1*1319, DRB1*1320, DRB1*1321, DRB1*1322, DRB1*1323, DRB1*1324, DRB1*1325, DRB1*1326, DRB1*1327, DRB1*1328, DRB1*1329, DRB1*1330, DRB1*1331, DRB1*1332, DRB1*1333, DRB1*1334, DRB1*1335, DRB1*1336, DRB1*1337, DRB1*1338, DRB1*1339, DRB1*1340, DRB1*1341, DRB1*1342, DRB1*1343, DRB1*1344, DRB1*1345, DRB1*1346, DRB1*1347, DRB1*1348, DRB1*1349, DRB1*1350, DRB1*1351, DRB1*1352, DRB1*1353, DRB1*1354, DRB1*1355, DRB1*1356, DRB1*1357, DRB1*1358, DRB1*1359, DRB1*1360, DRB1*1361, DRB1*1362, DRB1*1363, DRB1*1364, DRB1*1365, DRB1*140101, DRB1*140102, DRB1*1402, DRB1*140301, DRB1*140302, DRB1*1404, DRB1*140501, DRB1*140502, DRB1*1406, DRB1*140701, DRB1*140702, DRB1*1408, DRB1*1409, DRB1*1410, DRB1*1411, DRB1*1412, DRB1*1413, DRB1*1414, DRB1*1415, DRB1*1416, DRB1*1417, DRB1*1418, DRB1*1419, DRB1*1420, DRB1*1421, DRB1*1422, DRB1*1423, DRB1*1424, DRB1*1425, DRB1*1426, DRB1*1427, DRB1*1428, DRB1*1429, DRB1*1430, DRB1*1431, DRB1*1432, DRB1*1433, DRB1*1434, DRB1*1435, DRB1*1436, DRB1*1437, DRB1*1438, DRB1*1439, DRB1*1440, DRB1*1441, DRB1*1442, DRB1*1443, DRB1*1444, DRB1*1445, DRB1*1446, DRB1*1447, DRB1*1448, DRB1*150101, DRB1*150102, DRB1*150103, DRB1*150104, DRB1*150105, DRB1*150201, DRB1*150202, DRB1*150203, DRB1*1503, DRB1*1504, DRB1*1505, DRB1*1506, DRB1*1507, DRB1*1508, DRB1*1509, DRB1*1510, DRB1*1511, DRB1*1512, DRB1*1513, DRB1*1514, DRB1*1515, DRB1*1516, DRB1*160101, DRB1*160102, DRB1*160201, DRB1*160202, DRB1*1603, DRB1*1604, DRB1*160501, DRB1*160502, DRB1*1607, DRB1*1608.

HLA-DRB2-9
DRB2*0101, DRB3*010101, DRB3*01010201, DRB3*01010202, DRB3*010103, DRB3*010104, DRB3*0102, DRB3*0103, DRB3*0104, DRB3*0105, DRB3*0106, DRB3*0107, DRB3*0108, DRB3*0109, DRB3*0110, DRB3*0111, DRB3*0201, DRB3*020201, DRB3*020202, DRB3*020203, DRB3*020204, DRB3*0203, DRB3*0204, DRB3*0205, DRB3*0206, DRB3*0207, DRB3*0208, DRB3*0209, DRB3*0210, DRB3*0211, DRB3*0212, DRB3*0213, DRB3*0214, DRB3*0215, DRB3*0216, DRB3*0217, DRB3*0218, DRB3*0219, DRB3*030101, DRB3*030102, DRB3*0302, DRB3*0303, DRB4*01010101, DRB4*0102, DRB4*01030101, DRB4*01030102N, DRB4*010302, DRB4*010303, DRB4*010304, DRB4*0104, DRB4*0105, DRB4*0106, DRB4*0107, DRB4*0201N, DRB4*0301N, DRB5*010101, DRB5*010102, DRB5*0102, DRB5*0103, DRB5*0104, DRB5*0105, DRB5*0106, DRB5*0107, DRB5*0108N, DRB5*0109, DRB5*0110N, DRB5*0111, DRB5*0112, DRB5*0113, DRB5*0202, DRB5*0203, DRB5*0204, DRB5*0205, DRB6*0101, DRB6*0201, DRB6*0202, DRB7*010101, DRB7*010102, DRB8*0101, DRB9*0101.

HLA-DQA1
DQA1*010101, DQA1*010102, DQA1*010201, DQA1*010202, DQA1*0103, DQA1*010401, DQA1*010402, DQA1*0105, DQA1*0106, DQA1*0107, DQA1*0201, DQA1*030101, DQA1*0302, DQA1*0303, DQA1*040101, DQA1*040102, DQA1*0402, DQA1*0403N, DQA1*0404, DQA1*050101, DQA1*050102, DQA1*0502, DQA1*0503, DQA1*0504, DQA1*0505, DQA1*060101, DQA1*060102, DQA1*0602.

HLA-DQB1
DQB1*020101, DQB1*020102, DQB1*0202, DQB1*0203, DQB1*030101, DQB1*030102, DQB1*030201, DQB1*030202, DQB1*030302, DQB1*030303, DQB1*0304, DQB1*030501, DQB1*030502, DQB1*030503, DQB1*0306, DQB1*0307, DQB1*0308, DQB1*0309, DQB1*0310, DQB1*0311, DQB1*0312, DQB1*0313, DQB1*0401, DQB1*0402, DQB1*050101, DQB1*050102, DQB1*050201, DQB1*050202, DQB1*050301, DQB1*050302, DQB1*0504, DQB1*060101, DQB1*060102, DQB1*060103, DQB1*0602, DQB1*0603, DQB1*060401, DQB1*060402, DQB1*060501, DQB1*060502, DQB1*0606, DQB1*0607, DQB1*0608, DQB1*0609,

DQB1*0610, DQB1*061101, DQB1*061102, DQB1*0612, DQB1*0613, DQB1*0614, DQB1*0615, DQB1*0616, DQB1*0617, DQB1*0618, DQB1*0619, DQB1*0620, DQB1*0621, DQB1*0622, DQB1*0623.
HLA-DPA1
DPA1*010301, DPA1*010302, DPA1*010303, DPA1*0104, DPA1*0105, DPA1*0106, DPA1*0107, DPA1*0108, DPA1*020101, DPA1*020102, DPA1*020103, DPA1*020104, DPA1*020105, DPA1*020106, DPA1*020201, DPA1*020202, DPA1*020203, DPA1*0203, DPA1*0301, DPA1*0302, DPA1*0303, DPA1*0401.
HLA-DPB1
DPB1*010101, DPB1*010102, DPB1*010103, DPB1*0102, DPB1*020102, DPB1*020103, DPB1*020104, DPB1*020105, DPB1*020106, DPB1*0202, DPB1*0203, DPB1*030101, DPB1*030102, DPB1*0302, DPB1*040101, DPB1*040102, DPB1*0402, DPB1*0501, DPB1*0601, DPB1*0801, DPB1*0901, DPB1*1001, DPB1*110101, DPB1*110102, DPB1*1301, DPB1*1401, DPB1*1501, DPB1*1601, DPB1*1701, DPB1*1801, DPB1*1901, DPB1*200101, DPB1*200102, DPB1*2101, DPB1*2201, DPB1*2301, DPB1*2401, DPB1*2501, DPB1*260101, DPB1*260102, DPB1*2701, DPB1*2801, DPB1*2901, DPB1*3001, DPB1*3101, DPB1*3201, DPB1*3301, DPB1*3401, DPB1*3501, DPB1*3601, DPB1*3701, DPB1*3801, DPB1*3901, DPB1*4001, DPB1*4101, DPB1*4401, DPB1*4501, DPB1*4601, DPB1*4701, DPB1*4801, DPB1*4901, DPB1*5001, DPB1*5101, DPB1*5201, DPB1*5301, DPB1*5401, DPB1*5501, DPB1*5601, DPB1*5701, DPB1*5801, DPB1*5901, DPB1*6001, DPB1*6101N, DPB1*6201, DPB1*6301, DPB1*6401N, DPB1*6501, DPB1*6601, DPB1*6701, DPB1*6801, DPB1*6901, DPB1*7001, DPB1*7101, DPB1*7201, DPB1*7301, DPB1*7401, DPB1*7501, DPB1*7601, DPB1*7701, DPB1*7801, DPB1*7901, DPB1*8001, DPB1*8101, DPB1*8201, DPB1*8301, DPB1*8401, DPB1*8501, DPB1*8601, DPB1*8701, DPB1*8801, DPB1*8901, DPB1*9001, DPB1*9101, DPB1*9201, DPB1*9301, DPB1*9401, DPB1*9501, DPB1*9601, DPB1*9701, DPB1*9801, DPB1*9901.
HLA-DMA
DMA*0101, DMA*0102, DMA*0103, DMA*0104.
HLA-DMB
DMB*0101, DMB*0102, DMB*0103, DMB*0104, DMB*0105, DMB*0106.
HLA-DOA
DOA*010101, DOA*01010201, DOA*01010202, DOA*01010203, DOA*010103, DOA*01010401, DOA*01010402, DOA*010105.
HLA-DOB
DOB*01010101, DOB*01010102, DOB*010102, DOB*010201, DOB*010202, DOB*0103, DOB*01040101, DOB*01040102.
MHC Class I
H-2Db, H-2Dd, H-2Dk, H-2Dq, H-2Kb, H-2Kd, H-2Kk, H-2Ld, H-2M3, H-2Ad, H-2Ag7, H-2Ak, H2-Ab, H-2Ed, H-2Ek, H-2Bxk, H-2F, H-2I, H-2P, H-2R, H-2S, H-2Sxd, H-2T4, H-2U.
MHC Class II
I-Ab, I-Ad, I-Ag7, I-Ak, I-Ap, I-Aq, I-Ar, I-As, I-Au, I-Av, I-Ea, I-Eb, I-Ed, I-Ek, I-Es, I-Eu, H-2Q, H-2Qa-2, H-2Qa-2a, Qa-1a, Qa-1b.

The invention is not limited to such MHC and HLA molecules, and can be adapted to newly discovered such molecules, if desired, simply by establishing the reactivity of substances such as peptides with the molecules. This can be readily achieved using known techniques that are standard in the field. Particularly preferred HLA alleles for use with the present invention include the following:

| HLA Class I | | |
|---|---|---|
| HLA A | HLA B | HLA Cw |
| A*6802 | B*5801 | Cw*1701 |
| A*6801 | B*5701 | Cw*1601 |
| A*6601 | B*5501 | Cw*1502 |
| A*3303 | B*5201 | Cw*1402 |
| A*3301 | B*5101 | Cw*1203 |
| A*3201 | B*5001 | Cw*0802 |
| A*310102 | B*4901 | Cw*0801 |
| A*3002 | B*4501 | Cw*0704 |
| A*3001 | B*4403 | Cw*0703 |
| A*2902 | B*4402 | Cw*0702 |
| A*2608 | B*4101 | Cw*0701 |
| A*2601 | B*4002 | Cw*0602 |
| A*2501 | B*4001 | Cw*0501 |
| A*2402 | B*3901 | Cw*0401 |
| A*2301 | B*3801 | Cw*0304 |
| A*1101 | B*3701 | Cw*0303 |
| A*0302 | B*3503 | Cw*0202 |
| A*0301 | B*3501 | Cw*0102 |
| A*0205 | B*2705 | |
| A*0201 | B*1801 | |
| A*0101 | B*1501 | |
| | B*1402 | |
| | B*1401 | |
| | B*1302 | |
| | B*0801 | |
| | B*0705 | |
| | B*0702 | |

| HLA Class II | | | |
|---|---|---|---|
| HLA DPB | HLA DQA | HLA DQB | HLA DRB |
| DPB1*1701 | DQA1*0505 | DQB1*0604 | DRB1*1601 |
| DPB1*1301 | DQA1*0501 | DQB1*0603 | DRB1*1501 |
| DPB1*1001 | DQA1*0401 | DQB1*0602 | DRB1*1401 |
| DPB1*0601 | DQA1*0303 | DQB1*0503 | DRB1*1302 |
| DPB1*0501 | DQA1*0302 | DQB1*0502 | DRB1*1301 |
| DPB1*0402 | DQA1*0301 | DQB1*0501 | DRB1*1201 |
| DPB1*0401 | DQA1*0201 | DQB1*0402 | DRB1*1104 |
| DPB1*0301 | DQA1*0104 | DQB1*0303 | DRB1*1101 |
| DPB1*0201 | DQA1*0103 | DQB1*0302 | DRB1*0801 |
| DPB1*0101 | DQA1*0102 | DQB1*0301 | DRB1*0701 |
| | DQA1*0101 | DQB1*0202 | DRB1*0404 |
| | | DQB1*0201 | DRB1*0401 |
| | | | DRB1*0301 |
| | | | DRB1*0103 |
| | | | DRB1*0102 |
| | | | DRB1*0101 |

The most preferred alleles according to the invention are the following:
HLA-A*0201, HLA-A*0206, HLA-A*0301, HLA-A*1101, HLA-A*2402, HLA-A*3401, HLA-B*0702, HLA-B*0801, HLA-B*1301, HLA-B*27, HLA-B*4002, HLA-B*5101, HLA-Cw*03, HLA-cW*07

HLA-DRB1*0301, HLA-DRB1*0401, HLA-DRB1*0701, HLA-DRB1*1501, HLA-DRB1*1104, HLA-DRB1*1101, HLA-DRB4*0101

HLA-DQA1*01, HLA-DQA1*02, HLA-DQA1*05

HLA-DQB1*03, HLA-DQB1*04, HLA-DQB1*05, HLA-DQB1*06

HLA-DPA1*01, HLA-DPA1*02

HLA-DPB1*02, HLA-DPB1*04

The invention will now be described by way of example only, with reference to the following specific embodiments.

EXAMPLES

Preparation of Arthropod Saliva Protein Fractions

In order to determine the effect of specific sequences of the invention, their immunogenicity may be tested against various arthropod saliva protein fractions. Those sequences that cause a vertebrate to produce immune system cells that recognise at least one epitope in specific saliva protein fractions are useful in the vaccines of the present invention.

The saliva protein fractions can easily be isolated using standard laboratory techniques, which are well known to the skilled person. Any arthropod saliva protein fractions may be used, since the inventors have determined that it is the mass of the protein fraction that is important. The fractions of mass 40 kDa or less, 30 kDa or less, preferably from 20-40 kDa, and more preferably 20 kDa or less, are particularly useful.

The following protocol is provided to exemplify the protein fraction against which candidate sequences may be tested. It utilises saliva from *anopheles gambiae* mosquitoes, although any arthropod saliva may be employed.

Figure 9:
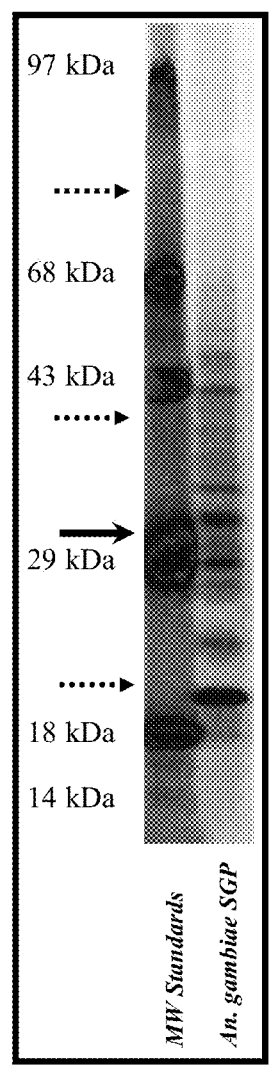

*Anopheles gambiae* salivary gland pairs (SGP) were dissected from female mosquitoes colonies. Fifteen SGPs were collected in 20 μl of PBS and lysed by adding 5 μl of 5× SDS-PAGE sample buffer containing 0.25% 2-β-ME. After vortexing and boiling for 5 min, the protein mixture was loaded on a Novex 4-20% gradient Tris-Glycine gel (INVITROGEN). The gel was then silver stained and photographed (see FIG. 9).

The dashed arrows indicate the position of the cut off points for selection of SGP fractions that may be used for immunisation and study (i.e. <20 kDa, 20-40 kDa, 40-80 kDa and >80 kDa). The solid arrow indicates the position of the cut off point for selection of SGP fractions of <30 kDa and >30 kDa.

Identifying Candidate Protein Samples from Mosquito Saliva

Taking a similar approach to the exemplary protocol outlined above, several saliva protein samples were prepared for study.

Salivary glands (SG) were dissected from female *Anopheles gambiae* mosquitoes and stored in PBS at −70° C. until use.

Figure 1:
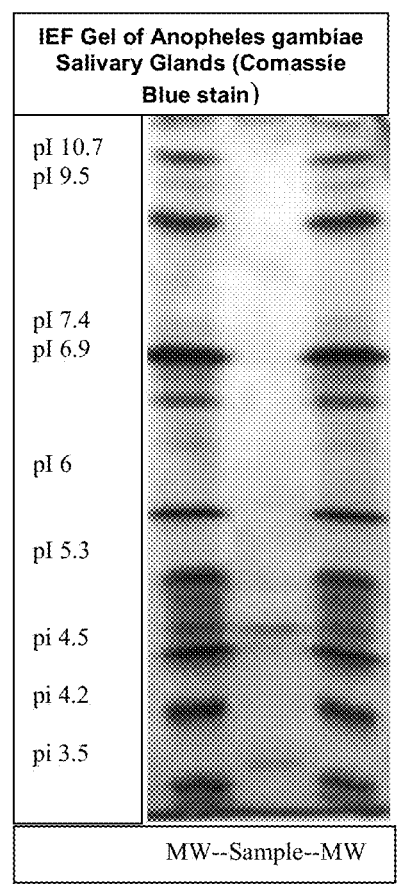
FIGS. 1 and 9 show IEF gels of *anopheles gambiae* salivary glands (Comassie Blue stain), as produced in accordance with the protocols set out in the Examples.

For gel analysis, SGs were lysed by freeze-thawing, Novex® IEF Sample Buffer pH 3-10 (Invitrogen) added and the resulting material analysed in a Novex® IEF Gel (Invitrogen). The gel was then fixed with 12% TCA, washed three times in water and stained with Comassie Blue. The resulting gel is shown in FIG. 1.

Figure 2:
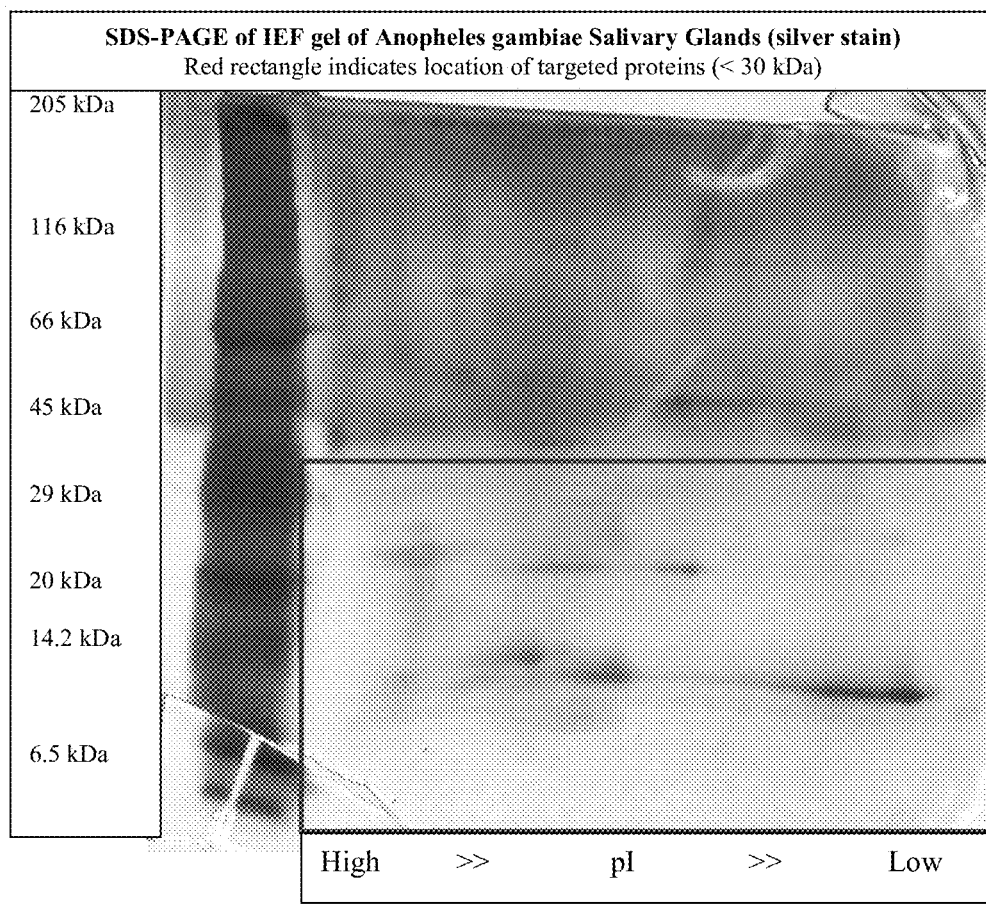
FIG. 2 shows an SDS-PAGE of the IEF gel of FIG. 1 (silver stain)—the red rectangle indicates the location of one of the targeted proteins (<30 kDa)
Figure 3A:
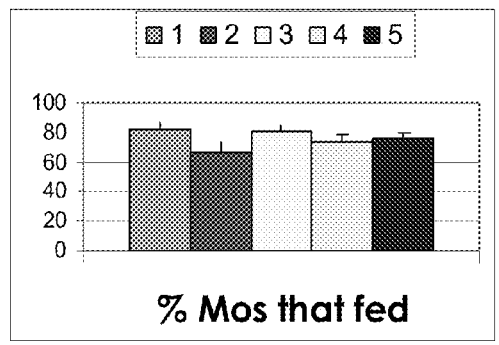
FIGS. 3A-3I show data on the effect of the vaccine on the fecundity of mosquitoes, as follows.
Figure 3B:
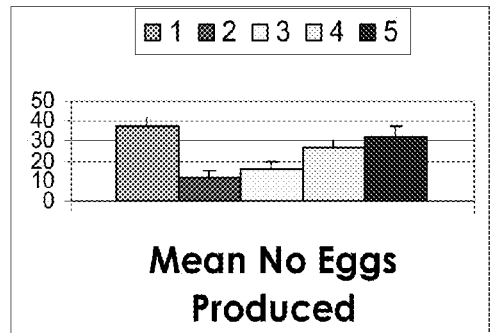
Figure 3C:
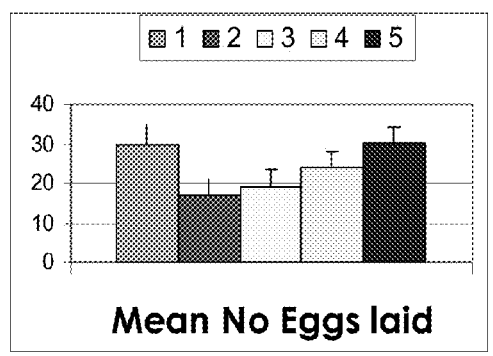
Figure 3D:
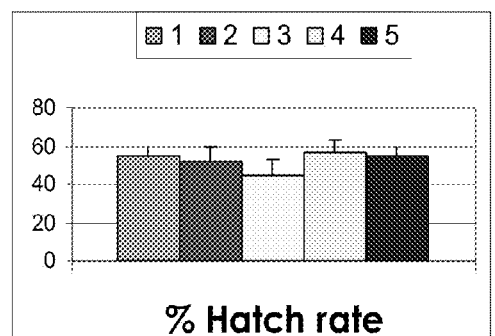
Figure 3E:
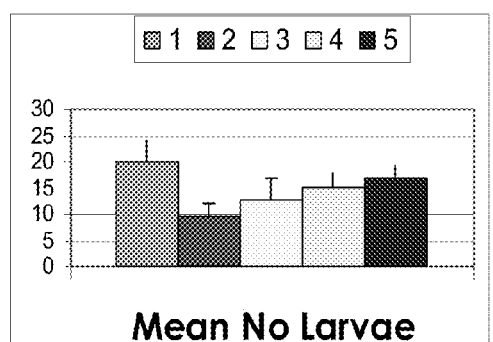
Figure 3F:
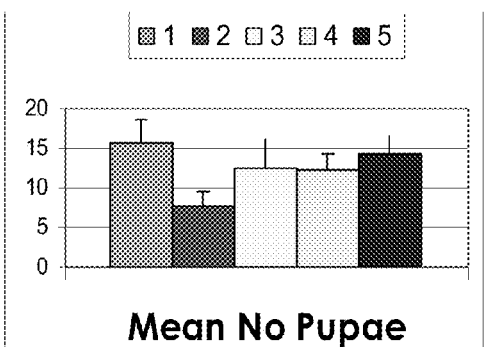
Figure 3G:
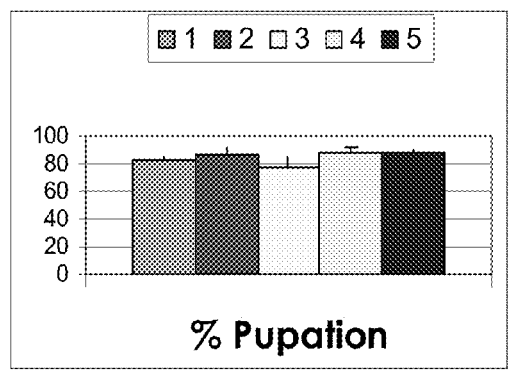
Figure 3H:
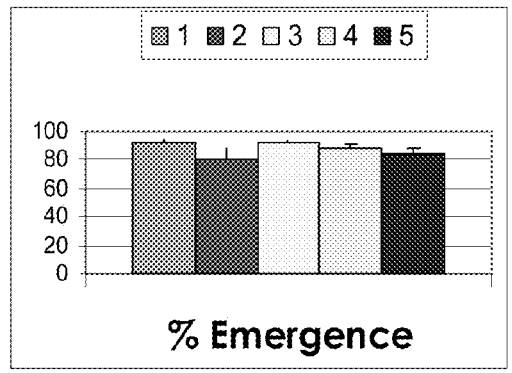
Figure 3I:
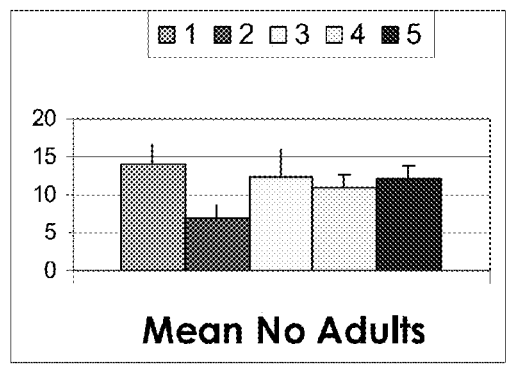

After staining and destaining, the IEF gel was incubated in 20% ethanol for 10 minutes and the gel strip containing the lane with the SG proteins cut out. This gel strip was equilibrated for 5 min in 2×SDS-PAGE sample buffer containing 20% ethanol, rinsed twice in SDS-PAGE sample buffer and loaded in the single well of a Novex® 4-20% Tris-Glycine Gel (Invitrogen). The resulting gel is shown in FIG. 2.

The gel containing the separated SG proteins was finally stained using the Proteosilver stain kit (Sigma) according to the manufacturer's instructions.

From the gel, four groups of proteins (designated compounds 1, 2, 3 and 4) were identified for analysis:
Compound 1 Salivary Gland Protein Fraction <20 kDa
Compound 2 Salivary Gland Protein Fraction 20 kDa<X<40 kDa
Compound 3 Salivary Gland Protein Fraction 40 kDa<X<80 kDa
Compound 4 Salivary Gland Protein Fraction >80 kDa Experiment 1

Aims (A) Establish efficacy of candidates in protecting animals against challenge by bite of infected mosquitoes (i.e. *Plasmodium yoelii* nigeriensis infected *Anopheles gambiae*)

(B) Establish cross-reactivity level of the anti-mosquito response induced by candidates across different species of mosquitoes (e.g. *Anopheles gambiae* and *Anopheles stephensi*).

(C) Establish efficacy of candidates in preventing infection of mosquitoes (*Anopheles gambiae* and *Anopheles stephensi*) by *Plasmodium yoelii* nigeriensis after biting immunised and infected mice.

Candidate Compounds

The compounds selected were those identified above:
Compound 1 Salivary Gland Protein Fraction <20 kDa
Compound 2 Salivary Gland Protein Fraction 20 kDa<X<40 kDa
Compound 3 Salivary Gland Protein Fraction 40 kDa<X<80 kDa
Compound 4 Salivary Gland Protein Fraction >80 kDa Strain and Number of Animals Involved:

CD1 mice are used. There were five experimental groups (1, 2, 3, 4 and 5) with group 1 being the negative control group and groups 2-5 the test groups, each group having nine (9) animals.

Experimental Protocol

Day 1: 4 groups were immunised (groups 2, 3, 4 and 5) of 9 CD1 mice each (N=4×9=36) with subcutaneous doses of candidate vaccine compounds (Group 2 with compound 1, Group 3 with compound 2, and so on).

Day 14: All animals were boosted with the same doses of candidate vaccine candidate vaccine compounds (Group 2 with compound 1, Group 3 with compound 2, and so on).

Day 21: All animals were test bled. Samples were stored frozen (−20° C.) until collection. Each group was split into further subgroups: A—5 animals, B—4 animals.

| Group 1A - 5 animals | Group 1B - 4 animals |
| Group 2A - 5 animals | Group 2B - 4 animals |
| Group 3A - 5 animals | Group 3B - 4 animals |
| Group 4A - 5 animals | Group 4B - 4 animals |
| Group 5A - 5 animals | Group 5B - 4 animals |

Subgroups A

Day 28: All animals in subgroups A were challenged via bite of 5-9 infected mosquitoes (i.e. *Plasmodium yoelii* nigeriensis infected *Anopheles gambiae*) in the belly area. All animals were maintained until parasitemia is first established or for a maximum of 6 weeks after challenge with infected mosquitoes. All animals were killed by exsanguination and the sera samples were stored frozen (−20° C.) until collection.

Subgroups B

Day 28: All animals in subgroups B were used to feed (in the belly area) the following number of fresh (uninfected) mosquitoes:
5-10 *Anopheles gambiae* AND 5-10 *Anopheles stephensi*

All these mosquitoes were tested for:
1. Survival over an 8 day period.
2. Number of eggs laid.
3. Number of eggs produced.
4. Number of adults (F1) produced from the eggs laid.

Day 32: All animals in subgroups B were infected with *Plasmodium yoelii* nigeriensis by direct IV inoculation of parasites.

Day 32: Once active malaria infection had been identified in all (or at least 75%) animals in Group B, all infected animals were used to feed (in the belly area) large numbers (>10 per mice) of both fresh *Anopheles gambiae* AND fresh *Anopheles stephensi*.

All these mosquitoes were tested for:
1. Survival over an 8 day period.
2. Number of mosquitoes with malarial parasites in their salivary glands amongst those who survived the required incubation period (17 days).
3. Number of eggs laid.
4. Number of eggs produced.
5. Number of adults (F1) produced from the eggs laid.

After mosquito feeding, all animals were killed by exsanguination and the sera samples were stored frozen (−20° C.) until collection.

Any volume of the experimental compound remaining at the end of the study was stored frozen (−20° C.) until collection.

Results

Graphical representations of the results of the experiments are shown in FIGS. 3A-3I and 4. The first set of Figures (FIG. 3*x*) show data on the effect of the vaccine on the fecundity of mosquitoes, for each of the Groups 1-5, as follows:

| | |
|---|---|
| 3A: Percent that fed | 3B: Mean no eggs produced |
| 3C: Mean no eggs laid | 3D: Percent hatch rate |
| 3E: Mean no larvae | 3F: Mean no pupae |
| 3G: Percent pupation | 3H: Percent emergence |
| 3I: Mean no adults | |

The numerical data underpinning each of these graphical representations A-I are set down respectively (column A for FIG. 3A, and so on) in Table 2 below:

TABLE 2

Data for FIGS. 3A-3I

| Mean ± Std. Error | A | B | C | D | E |
|---|---|---|---|---|---|
| Group 1 | 82.7 ± 4 | 29.6 ± 5 | 37.5 ± 4.6 | 20.1 ± 3.9 | 54.6 ± 4.7 |
| Group 2 | 66.7 ± 6.5 | 17.1 ± 3.8 | 12 ± 3 | 9.7 ± 2.4 | 51.9 ± 7.4 |
| Group 3 | 81.2 ± 3.4 | 19.1 ± 4.6 | 16 ± 3.7 | 12.9 ± 4 | 44.3 ± 8.7 |
| Group 4 | 73.7 ± 4.9 | 24.1 ± 3.9 | 26.4 ± 3.9 | 15 ± 2.8 | 56.6 ± 6.6 |
| Group 5 | 75.7 ± 4.5 | 30.1 ± 4.1 | 32.4 ± 5 | 16.9 ± 2.5 | 55 ± 4.6 |

| Mean ± Std. Error | F | G | H | I |
|---|---|---|---|---|
| Group 1 | 15.6 ± 3 | 82.9 ± 3 | 14 ± 2.8 | 92.4 ± 2.6 |
| Group 2 | 7.8 ± 1.8 | 86.1 ± 5.7 | 6.9 ± 1.8 | 80 ± 7.8 |
| Group 3 | 12.6 ± 3.7 | 77.7 ± 7.3 | 12.5 ± 3.6 | 92 ± 1.8 |
| Group 4 | 12.3 ± 2.1 | 88.5 ± 3.3 | 10.8 ± 1.9 | 88.8 ± 2.4 |
| Group 5 | 14.4 ± 2.2 | 88.4 ± 2.7 | 12.1 ± 1.8 | 84.8 ± 3.7 |

The data set out in Tables 3A-3I below show the p-values obtained using a Mann-Whitney non-parametric statistical analysis of the above data.

TABLE 3A

P values for percent that fed

| | Compound 1 | Compound 2 | Compound 3 | Compound 4 |
|---|---|---|---|---|
| Group 1 | | | | |
| Group 2 | 0.10504 | | | |
| Group 3 | 0.41727 | 0.14813 | | |
| Group 4 | 0.14813 | 0.26543 | 0.10504 | |
| Group 5 | 0.23235 | 0.23235 | 0.26543 | 0.5 |

TABLE 3B

P values for mean no eggs produced

| | Compound 1 | Compound 2 | Compound 3 | Compound 4 |
|---|---|---|---|---|
| Group 1 | | | | |
| Group 2 | 4.6E−05 | | | |
| Group 3 | 0.00042 | 0.1612 | | |
| Group 4 | 0.04038 | 0.0032 | 0.01602 | |
| Group 5 | 0.17836 | 0.0018 | 0.00551 | 0.22172 |

TABLE 3C

P values for mean no eggs laid

| | Compound 1 | Compound 2 | Compound 3 | Compound 4 |
|---|---|---|---|---|
| Group 1 | | | | |
| Group 2 | 0.09451 | | | |
| Group 3 | 0.07626 | 0.49308 | | |
| Group 4 | 0.27329 | 0.09416 | 0.10891 | |
| Group 5 | 0.30616 | 0.01171 | 0.00879 | 0.15145 |

TABLE 3D

P values for percent hatch rate

| | Compound 1 | Compound 2 | Compound 3 | Compound 4 |
|---|---|---|---|---|
| Group 1 | | | | |
| Group 2 | 0.46767 | | | |
| Group 3 | 0.19155 | 0.29445 | | |
| Group 4 | 0.36699 | 0.33803 | 0.14632 | |
| Group 5 | 0.40058 | 0.47907 | 0.15041 | 0.40187 |

TABLE 3E

P values for mean no larvae

| | Compound 1 | Compound 2 | Compound 3 | Compound 4 |
|---|---|---|---|---|
| Group 1 | | | | |
| Group 2 | 0.04897 | | | |
| Group 3 | 0.07371 | 0.45038 | | |
| Group 4 | 0.29801 | 0.06197 | 0.11695 | |
| Group 5 | 0.4499 | 0.0164 | 0.06524 | 0.23691 |

TABLE 3F

P values for mean no pupae

| | Compound 1 | Compound 2 | Compound 3 | Compound 4 |
|---|---|---|---|---|
| Group 1 | | | | |
| Group 2 | 0.06224 | | | |
| Group 3 | 0.28662 | 0.22088 | | |
| Group 4 | 0.44057 | 0.04081 | 0.35186 | |
| Group 5 | 0.40546 | 0.01118 | 0.17373 | 0.25066 |

TABLE 3G

P values for percent pupation

| | Compound 1 | Compound 2 | Compound 3 | Compound 4 |
|---|---|---|---|---|
| Group 1 | | | | |
| Group 2 | 0.11277 | | | |
| Group 3 | 0.3664 | 0.13511 | | |
| Group 4 | 0.11848 | 0.50798 | 0.07764 | |
| Group 5 | 0.10627 | 0.41971 | 0.08354 | 0.37388 |

TABLE 3H

P values for percent emergence

| | Compound 1 | Compound 2 | Compound 3 | Compound 4 |
|---|---|---|---|---|
| Group 1 | | | | |
| Group 2 | 0.06876 | | | |
| Group 3 | 0.12815 | 0.25697 | | |
| Group 4 | 0.059 | 0.33712 | 0.2767 | |
| Group 5 | 0.02006 | 0.4853 | 0.18532 | 0.2943 |

TABLE 3I

P values for mean no adults

| | Compound 1 | Compound 2 | Compound 3 | Compound 4 |
|---|---|---|---|---|
| Group 1 | | | | |
| Group 2 | 0.04391 | | | |
| Group 3 | 0.47127 | 0.06735 | | |
| Group 4 | 0.3981 | 0.03908 | 0.47468 | |
| Group 5 | 0.46488 | 0.0123 | 0.31328 | 0.24603 |

FIG. 4 shows the percent survival of the mosquitoes in each of the five groups, over a period of 8 days. The number of mosquitoes in each group at day zero was as follows:

| | |
|---|---|
| Group 1 (control): | 100 |
| Group 2: | 89 |
| Group 3: | 100 |
| Group 4: | 99 |
| Group 5: | 98 |

The data relevant to the graphical representation of FIG. 4 is set out in Table 4 below:

TABLE 4

Data for FIG. 4

| Mean ± Std. Error | Day 0 | Day 1 | Day 2 | Day 3 | Day 4 |
|---|---|---|---|---|---|
| Group 1 | 100 ± 0 | 86 ± 4.2 | 77 ± 5 | 73 ± 5.2 | 61 ± 4.6 |
| Group 2 | 100 ± 0 | 53.4 ± 5.5 | 40.4 ± 5.3 | 36.4 ± 4.9 | 28 ± 5.2 |
| Group 3 | 100 ± 0 | 67 ± 4.5 | 51 ± 4.7 | 44 ± 4.9 | 36 ± 4.4 |
| Group 4 | 100 ± 0 | 78 ± 5.1 | 62 ± 5.7 | 60 ± 5.6 | 51 ± 4.9 |
| Group 5 | 100 ± 0 | 73 ± 5.6 | 53.4 ± 6.7 | 48.4 ± 6.3 | 41.4 ± 5.6 |

| Mean ± Std. Error | Day 5 | Day 6 | Day 7 | Day 8 |
|---|---|---|---|---|
| Group 1 | 58 ± 4.8 | 56 ± 4.4 | 53 ± 4.5 | 53 ± 4.5 |
| Group 2 | 23.7 ± 5 | 21.4 ± 4.8 | 20 ± 4.8 | 20 ± 4.8 |
| Group 3 | 30 ± 4.1 | 28 ± 3.7 | 28 ± 3.7 | 28 ± 3.7 |
| Group 4 | 46 ± 5 | 46 ± 5 | 43 ± 5.2 | 43 ± 5.2 |
| Group 5 | 36.7 ± 5 | 33.7 ± 5.3 | 29.4 ± 5 | 29.4 ± 5 |

The data set out in Table 5(i)-5(viii) below show the p-values obtained using a Mann-Whitney non-parametric statistical analysis of the above data.

TABLE 5(i)

P values for day 1

| Day 1 | Compound 1 | Compound 2 | Compound 3 | Compound 4 |
|---|---|---|---|---|
| Group 1 | | | | |
| Group 2 | 2.6E−05 | | | |
| Group 3 | 0.00217 | 0.0326 | | |
| Group 4 | 0.13228 | 0.0007 | 0.0387 | |
| Group 5 | 0.0526 | 0.0071 | 0.1588 | 0.2738 |

TABLE 5(ii)

P values for day 2

| Day 2 | Compound 1 | Compound 2 | Compound 3 | Compound 4 |
|---|---|---|---|---|
| Group 1 | | | | |
| Group 2 | 1.1E−05 | | | |
| Group 3 | 0.0003 | 0.0676 | | |
| Group 4 | 0.0274 | 0.00453 | 0.06759 | |
| Group 5 | 0.0049 | 0.07833 | 0.44598 | 0.166 |

TABLE 5(iii)

P values for day 3

| Day 3 | Compound 1 | Compound 2 | Compound 3 | Compound 4 |
|---|---|---|---|---|
| Group 1 | | | | |
| Group 2 | 1.1E−05 | | | |
| Group 3 | 0.0002 | 0.20756 | | |
| Group 4 | 0.04955 | 0.00253 | 0.0213 | |
| Group 5 | 0.00311 | 0.07692 | 0.26734 | 0.10538 |

TABLE 5(iv)

P values for day 4

| Day 4 | Compound 1 | Compound 2 | Compound 3 | Compound 4 |
|---|---|---|---|---|
| Group 1 | | | | |
| Group 2 | 3.8E−05 | | | |
| Group 3 | 0.00032 | 0.12615 | | |

TABLE 5(iv)-continued

P values for day 4

| Day 4 | Compound 1 | Compound 2 | Compound 3 | Compound 4 |
|---|---|---|---|---|
| Group 4 | 0.09515 | 0.00175 | 0.01525 | |
| Group 5 | 0.0065 | 0.04759 | 0.24854 | 0.09848 |

TABLE 5(v)

P values for day 5

| Day 5 | Compound 1 | Compound 2 | Compound 3 | Compound 4 |
|---|---|---|---|---|
| Group 1 | | | | |
| Group 2 | 2.6E−05 | | | |
| Group 3 | 6.9E−05 | 0.14515 | | |
| Group 4 | 0.07976 | 0.00198 | 0.00944 | |
| Group 5 | 0.00393 | 0.03955 | 0.14962 | 0.09848 |

TABLE 5(vi)

P values for day 6

| Day 6 | Compound 1 | Compound 2 | Compound 3 | Compound 4 |
|---|---|---|---|---|
| Group 1 | | | | |
| Group 2 | 1E−05 | | | |
| Group 3 | 2.3E−05 | 0.12817 | | |
| Group 4 | 0.12022 | 0.00081 | 0.00393 | |
| Group 5 | 0.0034 | 0.05802 | 0.22172 | 0.0558 |

TABLE 5(vii)

P values for day 7

| Day 7 | Compound 1 | Compound 2 | Compound 3 | Compound 4 |
|---|---|---|---|---|
| Group 1 | | | | |
| Group 2 | 2.3E−05 | | | |
| Group 3 | 8.4E−05 | 0.07147 | | |
| Group 4 | 0.13648 | 0.00175 | 0.01315 | |
| Group 5 | 0.00132 | 0.09032 | 0.40795 | 0.03713 |

TABLE 5(viii)

P values for day 8

| Day 8 | Compound 1 | Compound 2 | Compound 3 | Compound 4 |
|---|---|---|---|---|
| Group 1 | | | | |
| Group 2 | 2.3E−05 | | | |
| Group 3 | 8.4E−05 | 0.07147 | | |
| Group 4 | 0.13648 | 0.00175 | 0.01315 | |
| Group 5 | 0.00132 | 0.09032 | 0.40795 | 0.03713 |

Experiment 2

Induction of Cytokine Production by Polypeptide Antigens immunisation

Peptides and Recombinant Proteins

From experiment 1, the most effective fraction was studied further, to identify polypeptides for that may be employed in vaccines. The utility of the peptides of the present invention was determined using the following protocol.

Immunisations

All the polypeptides under study (antigen preparations) are synthesised by Fmoc chemistry.

Six to ten week old C57BL/6 mice are immunised subcutaneously with a 200 µl dose of the antigen preparation per mouse. In the test group, each dose of the antigen preparation contains an equimolar mixture of the peptides (10 nmol each) prepared in adjuvant (Sigma) according to the manufacturer's instructions. In the control group, each dose of the antigen preparation contains an equivalent dose of a non-relevant polypeptide prepared in IFA (Sigma) according to the manufacturer's instructions (NRP preparation).

On day 15 post-immunisation, all animals receive a booster immunisation using the same doses and route of delivery as originally.

Finally, on day 20 all animals are culled and their spleens and sera are collected.

Cytokine ELISA

Mouse spleens belonging to the same experimental group are pooled, gently pressed through cell strainers and red blood cells removed by treatment with red cell lysis buffer (nine parts 0.16 M $NH_4Cl$ and one part of 0.17 M Tris, pH 7.2). Splenocyte suspensions from each experimental group are plated in 96-well plates in quadruplicate at a density of $4 \times 10^6$ cells/well in IMDM medium (Invitrogen) supplemented with 0.02 mM β-mercaptoethanol (Sigma), 50 IU/50 mg/ml of penicillin/streptomycin (Sigma) and 10% FCS (Sigma) and containing each of the polypeptide antigens under study (2 µM). After 3 days incubation at 37° C., the supernatant is collected and analysed for IFN-γ and IL-4 by a sandwich cytokine ELISA according to the manufacturer's protocol (Pharmingen). The lower detection limits for the assay are 9.77 pg/ml for IL-4 and 39.06 µg/ml for IFN-γ.

IgG2a Specific ELISA

Microtiter ELISA 96-well plates (Becton-Dickinson) are coated with 2 µM of each experimental polypeptide in PBS. After overnight at incubation at 4° C., plates are washed twice in PBST (PBS containing 0.05% of Tween 20) and wells blocked with 1% BSA Fraction V in PBST. After 1 h incubation, plates are washed thrice in PBST and a range of dilutions of test and control sera in PBST added to the wells. After 2 h incubation, plates are washed six times in PBST, and primary anti-mouse-Ig2a sera are added to all wells. After 1 h incubation, plates are washed six times in PBST, and anti-primary anti-mouse-Ig2a sera added to all wells. After 1 h incubation, plates are washed seven times with in PBST and TMB substrate to all wells. After 20-30 minutes incubation, the reaction is stopped with HCl and the absorbance at 450 nm is read.

Statistical Analysis

Statistically significant differences in the IFN-γ response to different antigens between the test and control groups are established through non-parametric Mann-Whitney analysis of the samples. Differences are considered statistically significant if the p value is below 0.05.

Experiment 3

Assessment of the Immune Response to Various Polypeptides

The following polypeptides were investigated: SEQ ID 20, SEQ ID 28, SEQ ID 30, SEQ ID 31, SEQ ID 32 and SEQ ID 35. These peptides were mixed together to form a candidate vaccine for testing (called the AGS peptide mix).

The type and level of the immune response induced by vaccination with these peptides was assessed according to the protocol shown below:

Day 1: Immunise 2 groups of 4 CD1 mice each with the following subcutaneous doses of candidate vaccine products:

Non-relevant-peptide (NRP) mix (10 nmol each)+ISA-51

AGS peptide mix (10 nmol each)+ISA-51

Day 15: Boost all animals with the same doses of candidate vaccine products.

Day 21: Terminally bleed all animals. Harvest spleens individually and test for IFN-gamma reactivity to:
Individual AGS peptides (2 µM each)
AGS mix (0.5 µM and 2 µM each)
Con A (7.5 µg/ml)
Blank Post-Day 21: Test all sera for reactivity against AGS peptides.

Results

IFN-gamma production following 96 hour stimulation in vitro with the antigens is indicated in the graph in FIG. 5.

IFN-gamma responses to SEQ ID 28, SEQ ID 30 and SEQ ID 35 as well as to the AGS-mix preparation are statistically significant ($p<0.05$).

SEQ ID 20, SEQ ID 31 and SEQ ID 32 induce a higher response in the AGS-mix immunised animals, but they also appear to be stimulatory, in a non specific fashion, to the splenocytes of NRP-mix immunised mice.

The total Ig response in sera to the antigens indicated in the graph in FIG. 6. Total Ig responses to SEQ ID 20 and SEQ ID 30 are statistically significant ($p<0.05$).

Experiment 4

Challenge Study Following AGS Peptide Mix Immunisation

To test the capacity of the AGS-mix preparation to confer protection against natural malaria infection, CD1 mice were immunised and challenged according to the protocol below:

Day 0: Test bleed all animals. Retain samples for further analysis.

Day 1: Immunise 2 (two) groups of 8 CD1 mice each with the following subcutaneous doses of candidate vaccine products:
Non-relevant-peptide (NRP) mix (10 nmol each)+ISA-51
AGS peptide mix (10 nmol each)+ISA-51

Day 7: Test bleed all animals. Retain samples for further analysis.

Day 14: Boost animals with the same doses of candidate vaccine products.

Day 21: Test bleed all animals. Retain samples for further analysis.

Day 28: All animals are challenged via bite of 8 infected mosquitoes (i.e. *Plasmodium yoelii* nigeriensis infected *Anopheles gambiae*) in the belly area. All animals are maintained until parasitemia is first established or for a maximum of 6 weeks after challenge with infected mosquitoes.

Day 70 (max): Terminally bleed all animals.

Results

Total Ig response in sera to the AGS-mix at day 21 is indicated in the graph in FIG. 7.

One animal in the AGS-mix immunised group showed a significantly lower Total Ig response than the remaining animals in the group (<50% average total Ig response in the AGS-mix group).

On the day of challenge, one animal in the NRP-mix immunised group and two animals in the AGS-mix immunised group could not be challenged due to a shortage of infectious mosquitoes.

Of the animals that were challenged, those in the AGS-mix immunised group showed an increased survival rate than those in the control NRP-mix immunised group (see FIG. 8). The one animal that died in the AGS-mix immunised group was the same one that had failed to develop a strong antibody response to the AGS preparation.

---

The invention claimed is:

1. A polypeptide composition comprising an isolated polypeptide, the isolated polypeptide being SEQ ID NO: 35 or a sequence having 85% homology or more to SEQ ID NO 35, wherein the isolated polypeptide elicits an immune response in vertebrates against at least one epitope of a protein from an arthropod saliva fraction, wherein the arthropod saliva protein fraction has a mass of 40 kDa or less.

2. The polypeptide composition according to claim 1, wherein the composition further comprises one or more further isolated polypeptides, the one or more further isolated polypeptides being SEQ ID NO: 20, SEQ ID NO: 28, SEQ ID NO: 30, SEQ ID NO: 31, or SEQ ID NO: 32, or a polypeptide having 85% homology or more to SEQ ID NO: 20, SEQ ID NO: 28, SEQ ID NO: 30, SEQ ID NO: 31, or SEQ ID NO: 32.

3. The polypeptide composition according to claim 1, which composition comprises 2 or more isolated polypeptides.

4. The polypeptide composition according to claim 1, wherein the protein from the arthropod saliva fraction has a mass from 20 kDa to 40 kDa, or has a mass of 20 kDa or less.

5. The polypeptide composition according to claim 1, wherein the isolated polypeptide includes a cytotoxic T lymphocyte (CTL) epitope, and/or the isolated polypeptide includes a T helper lymphocyte (Th) epitope, and/or the isolated polypeptide includes a B lymphocyte epitope.

6. The polypeptide composition according to claim 1, comprising 2, 3, 4, 5, 6 or more epitopes.

7. The polypeptide composition according to claim 1, which is immunogenic against a plurality of arthropod salivary proteins.

8. The polypeptide composition according to claim 1, wherein the arthropod saliva protein fraction is a mosquito saliva protein fraction from any mosquito species.

9. The polypeptide composition according to claim 1, further comprising one or more further sequences from an arthropod salivary protein.

10. The polypeptide composition according to claim 2, in which the one or more further isolated polypeptides present are SEQ ID NO: 20, SEQ ID NO: 28, SEQ ID NO: 30, SEQ ID NO: 31, or SEQ ID NO: 32.

11. The polypeptide composition of claim 1, further comprising a pharmaceutically acceptable carrier.

12. A method of producing a polypeptide composition of claim 1, which method comprises mixing or combining one or more of the polypeptides with one or more further polypeptides, and/or with one or more further components, such as a carrier, an excipient, an adjuvant, a buffer, or a stabiliser.

13. A polypeptide construct comprising an isolated polypeptide linked to a carrier, the isolated polypeptide being SEQ ID NO: 35 or a sequence having 85% homology or more to SEQ ID NO 35, wherein the isolated polypeptide elicits an immune response in vertebrates against at least one epitope of a protein from an arthropod saliva fraction, wherein the arthropod saliva protein fraction has a mass of 40 kDa or less.

14. A method of producing a polypeptide construct as defined in claim 13, which method comprises attaching, combining or mixing a polypeptide composition with the carrier.

15. The polypeptide construct according to claim 13, wherein the carrier comprises an adjuvant and/or an excipient.

16. The polypeptide composition according to claim 2, wherein the one or more further isolated polypeptides include a polypeptide having 85% homology or more to SEQ ID NO: 20, a polypeptide having 85% homology or more to SEQ ID NO: 28, a polypeptide having 85% homology or more to SEQ ID NO: 30, a polypeptide having 85% homology or more to SEQ ID NO: 31, or a polypeptide having 85% homology or more to SEQ ID NO: 32.

17. The polypeptide composition according to claim 3, which composition comprises from 2 to 12 isolated polypeptides.

18. The polypeptide composition according to claim 3, which composition comprises from 2-6 isolated polypeptides.

19. The polypeptide composition according to claim 8, wherein the mosquito species is *Anopheles gambiae*.

* * * * *